US012643846B2

(12) United States Patent
Slusher et al.

(10) Patent No.: US 12,643,846 B2
(45) **Date of Patent: *Jun. 2, 2026**

(54) PRODRUGS OF ITACONATE AND METHYL ITACONATE

(71) Applicants: The Johns Hopkins University, Baltimore, MD (US); INSTITUTE OF ORGANIC CHEMISTRY AND BIOCHEMISTRY AS CR V.V.I., Prague (CZ)

(72) Inventors: Barbara Slusher, Baltimore, MD (US); Mohameed Islam, Baltimore, MD (US); Rana Rais, Baltimore, MD (US); Luis Garza, Baltimore, MD (US); Benjamin Bell, Baltimore, MD (US); Pavel Majer, Kretin (CZ); Lukas Tenora, Prague (CZ); Ivan Snajdr, Prague (CZ); Marcela Krecmerova, Prague (CZ)

(73) Assignees: The Johns Hopkins University, Baltimore, MD (US); INSTITUTE OF ORGANIC CHEMISTRY AND BIOCHEMISTRY AS CR V.V.I., Prague (CZ)

( * ) Notice: Subject to any disclaimer, the term of this patent is extended or adjusted under 35 U.S.C. 154(b) by 747 days.

This patent is subject to a terminal disclaimer.

(21) Appl. No.: 17/772,879

(22) PCT Filed: Oct. 29, 2020

(86) PCT No.: PCT/US2020/057912
§ 371 (c)(1),
(2) Date: Apr. 28, 2022

(87) PCT Pub. No.: WO2021/087082
PCT Pub. Date: May 6, 2021

(65) Prior Publication Data

US 2023/0028516 A1 Jan. 26, 2023

Related U.S. Application Data

(60) Provisional application No. 62/927,309, filed on Oct. 29, 2019.

(51) Int. Cl.
*C07C 69/593* (2006.01)
*A61K 31/225* (2006.01)
*C07C 229/36* (2006.01)
*C07C 237/12* (2006.01)
*C07C 271/22* (2006.01)

(52) U.S. Cl.
CPC .......... *C07C 69/593* (2013.01); *A61K 31/225* (2013.01); *C07C 229/36* (2013.01); *C07C 237/12* (2013.01); *C07C 271/22* (2013.01)

(58) Field of Classification Search
CPC ............................ C07C 69/593; A61K 31/225
See application file for complete search history.

(56) References Cited

U.S. PATENT DOCUMENTS

| | | | | |
|---|---|---|---|---|
| 2,782,228 | A | 2/1957 | Dazzi et al. | |
| 9,550,803 | B2 | 1/2017 | Mckenna et al. | |
| 2019/0262482 | A1* | 8/2019 | Llop Roig | A61K 51/04 |
| 2023/0025922 | A1* | 1/2023 | Garza | A61K 31/621 |
| 2024/0398739 | A1* | 12/2024 | Garza | A61K 31/225 |
| 2024/0400498 | A1* | 12/2024 | Slusher | C07C 69/593 |

FOREIGN PATENT DOCUMENTS

| | | | |
|---|---|---|---|
| CA | 3135991 | | 11/2020 |
| CN | 109627167 | A | 4/2019 |
| EP | 1331494 | | 7/2003 |
| EP | 4051255 | A1 | 9/2022 |
| FR | 2875403 | A1 | 3/2006 |
| JP | H5-39322 | A | 2/1993 |
| WO | WO 2017/142855 | | 8/2017 |
| WO | WO 2019/036509 | | 2/2019 |
| WO | WO 2020/222010 | A1 | 11/2020 |
| WO | WO2021087082 | | 5/2021 |

OTHER PUBLICATIONS

Katsikas at el. (Journal of Thermal Analysis, vol. 47 (1996) 1093-1104). (Year: 1996).*

Boschert et al., Synthesis and Bioactivity of Polymer-Based Synthetic Mimics of Antimicrobial Peptides (SMAMPs) Made from Asymmetrically Disubstituted Itaconates. Chemistry. Jun. 7, 2018;24(32):8217-8227.

Hidaka et al., Active site-directed plasmin inhibitors: Extension on the P2 residue. Bioorg Med Chem. Feb. 15, 2016;24(4):545-53.

O'Neill et al., Itaconate: the poster child of metabolic reprogramming in macrophage function. Nat Rev Immunol. May 2019;19(5):273-281.

T. W. Greene, P.G.M. Wuts, Protective Groups in Organic Synthesis, 4th ed. John Wiley & Sons, 2007, TOC only. 6 pages.

Israel Office Action for Application No. 292635 dated Sep. 16, 2024, 3 pages.

Japanese Office Action for Application No. 2022-525544 dated Oct. 15, 2024, 11 pages.

Indian Office Action for Application No. 202217030386 dated Sep. 13, 2024, 7 pages.

Extended EP Search Report for EP 20883005.9, mailed on Oct. 31, 2023, 9 pages.

Chollet et al., "Solid-phase Synthesis of alpha-substituted 3-Bisarylthio N-Hydroxy Propionamides as Specific MMP Inhibitors", Bioorganic & Medical Chemistry, vol. 10, No. 3, Jan. 1, 2002, pp. 531-544.

(Continued)

*Primary Examiner* — James H Alstrum-Acevedo
*Assistant Examiner* — Chris E Simmons
(74) *Attorney, Agent, or Firm* — Casimir Jones, S.C.; Robert A. Goetz

(57) ABSTRACT

Prodrugs of itaconic acid and 1- and 4-methyl itaconic acid and their use for treating a disease, disorder, or condition associated with inflammation are disclosed.

4 Claims, 3 Drawing Sheets

(56) References Cited

OTHER PUBLICATIONS

Dominguez et al., “A Series of Mono and Diesters of Itaconic Acid: Synthesis and Structural Determination”, Monatshefte fur Chemie, vol. 120, Jan. 1, 1989, pp. 743-748.
Eri et al., “Stereoselective catalytic hydrogenation and conjugate reduction of 4-methyl itaconate derivatives bearing a chiral auxiliary”, Tetrahedron, vol. 69, No. 16, Mar. 1, 2013, pp. 3486-3494.
Mills et al., “Itaconate is an anti-inflammatory metabolite that activates Nrf2 via alkylation of KEAP1”, Cleo: Applications and Technology 2019, vol. 556, No. 7699, Apr. 1, 2018, pp. 113-117.
Yu et al., “Itaconate an emerging determinant of inflammation in activated macrophages”, Immunology and Cell Biology, vol. 97, No. 2, Dec. 11, 2018, pp. 134-141.
Bis(2-ethoxyethyl) 2-methylideneburanedioate, PubChem CID 8795235, Feb. 12, 2015, 9 pages.
International Search Report and Written Opinion for PCT/US2020/057912, mailed Feb. 1, 2021.
Decision of Rejection for Chinese application No. 202080088327.2 dated Sep. 30, 2024, 5 pages.
Chinese Patent Application No. 202080088327.2 Office Action mailed Jun. 16, 2023, 8 pages.
CAS: 1428636-70-7, STN Registry Database, Apr. 18, 2013, 3 pages.
CAS: 204011-36-9, STN Registry Database, Apr. 12, 1998, 3 pages.
Eurasian Office Action for Application No. 202291263, dated Jun. 20, 2023, 2 pages.
Canadian Office Action for Application No. 3,156,882 dated Jan. 4, 2024, 6 pages.
Indonesian Office Action for Application No. P00202205669, dated Apr. 26, 2024, 4 pages.
Chinese Office Action for Application No. 202080088327.2 dated May 9, 2024, 5 pages.
Vietnamese Office Action for Application No. 1-2022-03129 dated Jun. 20, 2024, 2 pages.
Saudia Arabia Office Action for Application No. 522432494 dated Dec. 28, 2023, 4 pages.
Landry, Christine et al. Blends of Etheric Polyitaconates and Polyacrylates with Acidic Polymers, Macromolecules, Jun. 25, 1993, vol. 26, pp. 5543-5551.

* cited by examiner

IS-100-127

IS-100-128

IS-100-129

IS-100-142

IS-100-143

IS-100-149

MK-933

IS-102-081

IS-101-088 (21)

MK-937

IS-102-081

IS-101-088 (21)

IS-100-142

IS-100-149

PRODRUGS OF ITACONATE AND METHYL ITACONATE

CROSS-REFERENCE TO RELATED APPLICATIONS

This application is a 371 of PCT/US2020/057912 filed Oct. 29, 2020, which claims the benefit of U.S. Prov. Appl. 62/927,309 filed Oct. 29, 2019, the entire contents of which are incorporated herein by reference.

FEDERALLY SPONSORED RESEARCH OR DEVELOPMENT

This invention was made with government support under grants AR068280 and AR064297 awarded by the National Institutes of Health. The government has certain rights in the invention.

BACKGROUND

Inflammatory macrophages show substantial accumulation of itaconate, which has been shown to exert profound anti-inflammatory activity by inhibiting succinate dehydrogenase and inducing electrophilic stress that activates NRF2-dependent antioxidant responses. Given its charged nature, however, itaconate itself does not exhibit good pharmacokinetic or cell permeating properties. Thus, the therapeutic potential of administering exogenous itaconate has yet to be realized.

SUMMARY

The presently disclosed subject matter provides prodrugs of itaconic acid and 1- and 4-methyl itaconic acid and their use for treating a disease, disorder, or condition associated with inflammation.

More particularly, in some aspects, the presently disclosed subject matter provides a compound of formula (I):

(I)

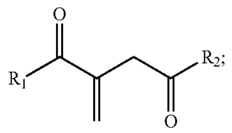

wherein:

$R_1$ and $R_2$ can be the same or different and are each independently selected from one or more of the following and combinations thereof:

(a) —$OR_3$, wherein $R_3$ is H or $C_1$-$C_6$ straight-chain or branched unsubstituted or substituted alkyl;

(b)

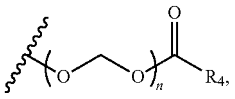

wherein n is an integer selected from 1, 2, 3, and 4; $R_4$ is $C_1$-$C_6$ straight-chain or branched unsubstituted or substituted alkyl or —$OR_5$, wherein $R_5$ is $C_1$-$C_6$ straight-chain or branched unsubstituted or substituted alkyl;

(c)

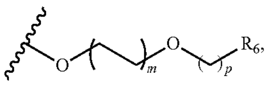

wherein m is an integer selected from 1, 2, 3, and 4; p is an integer selected from 1, 2, 3, 4, 5, 6, 7, 8, 9, 10, 11, 12, 13, 14, 15, 16, 17, 18, 19, and 20; and $R_6$ is $C_1$-$C_6$ straight-chain or branched unsubstituted or substituted alkyl;

(d)

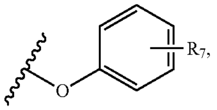

wherein $R_7$ is selected from:

(i) —C(═O)—O—$R_8$, wherein $R_8$ is $C_1$-$C_6$ straight-chain or branched unsubstituted or substituted alkyl;

(ii)

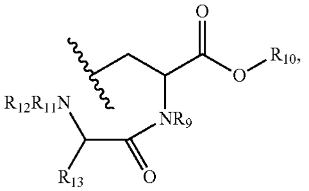

wherein $R_9$ is H or $C_1$-$C_4$ straight-chain or branched unsubstituted or substituted alkyl; $R_{10}$ is $C_1$-$C_6$ straight-chain or branched unsubstituted or substituted alkyl; $R_{11}$ and $R_{12}$ are each independently H or a protecting group; and $R_{13}$ is $C_1$-$C_6$ straight-chain or branched unsubstituted or substituted alkyl;

(iii)

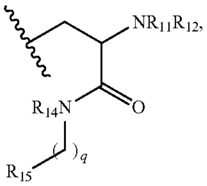

wherein q is an integer selected from 1, 2, 3, 4, 5, 6, 7, 8, 9, and 10; $R_{11}$ and $R_{12}$ are each independently H or a protecting group; $R_{14}$ is H or $C_1$-$C_4$ straightchain or branched unsubstituted or substituted alkyl; and $R_{15}$ is $C_1$-$C_6$ straight-chain or branched unsubstituted or substituted alkyl; and (iv)

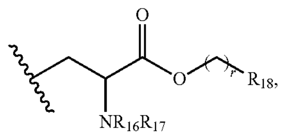

wherein $R_{16}$ and $R_{17}$ are each independently selected from H, $C_1$-$C_4$ straight-chain or branched unsubstituted or substituted alkyl, and a protecting group; $R_{18}$ is aryl;

(e)

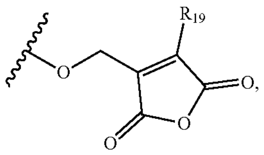

wherein $R_{19}$ is $C_1$-$C_4$ straight-chain or branched unsubstituted or substituted alkyl;

(f)

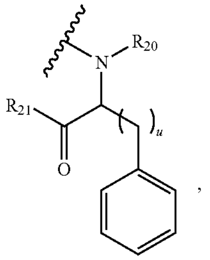

wherein u is an integer selected from 1, 2, 3, and 4; $R_{20}$ is H or $C_1$-$C_4$ straight-chain or branched unsubstituted or substituted alkyl; and $R_{21}$ is —$OR_{22}$, wherein $R_{22}$ is $C_1$-$C_6$ straightchain or branched unsubstituted or substituted alkyl or —$NR_{23}R_{24}$, wherein $R_{23}$ and $R_{24}$ are each independently H or $C_1$-$C_4$ straightchain or branched unsubstituted or substituted alkyl;

provided that $R_1$ and $R_2$ cannot both be —OH or both be —$OR_3$ at the same time;

and pharmaceutically acceptable salts thereof.

In other aspects, the presently disclosed subject matter provides a pharmaceutical composition comprising a compound of formula (I), or a pharmaceutically acceptable salt thereof and a pharmaceutically acceptable excipient.

In yet other aspects, the presently disclosed subject matter provides a method for treating a disease, disorder, or condition associated with inflammation, the method comprising administering to a subject in need of treatment thereof a compound of formula (I) or a pharmaceutical composition thereof.

Certain aspects of the presently disclosed subject matter having been stated hereinabove, which are addressed in whole or in part by the presently disclosed subject matter, other aspects will become evident as the description proceeds when taken in connection with the accompanying Examples and Drawings as best described herein below.

BRIEF DESCRIPTION OF THE DRAWINGS

Figure 1:
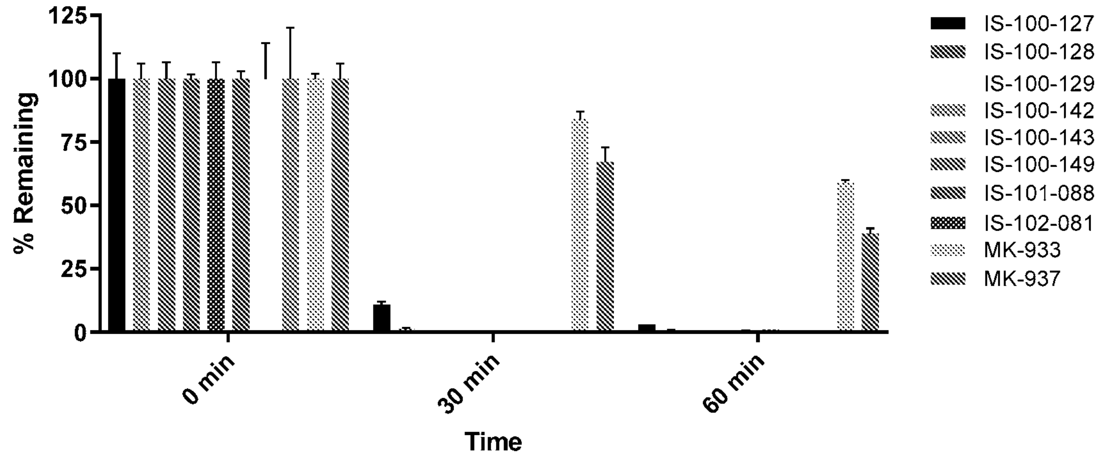
Figure 1:
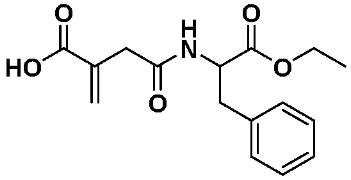
Figure 1:
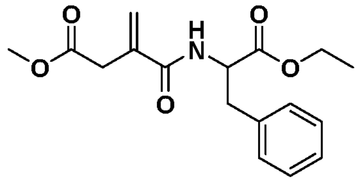
Figure 1:
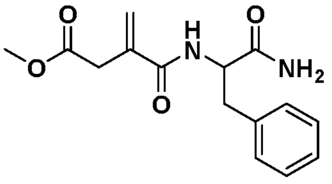
Figure 1:
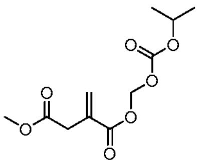
Figure 1:
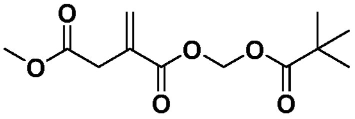
Figure 1:
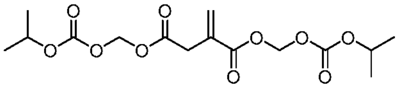
Figure 1:
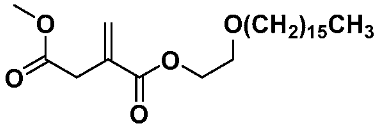
Figure 1:
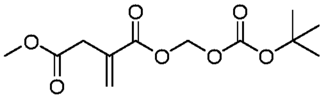
Figure 1:
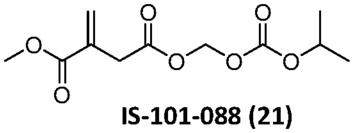
Figure 1:
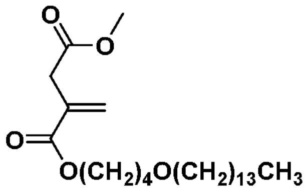
Figure 2:
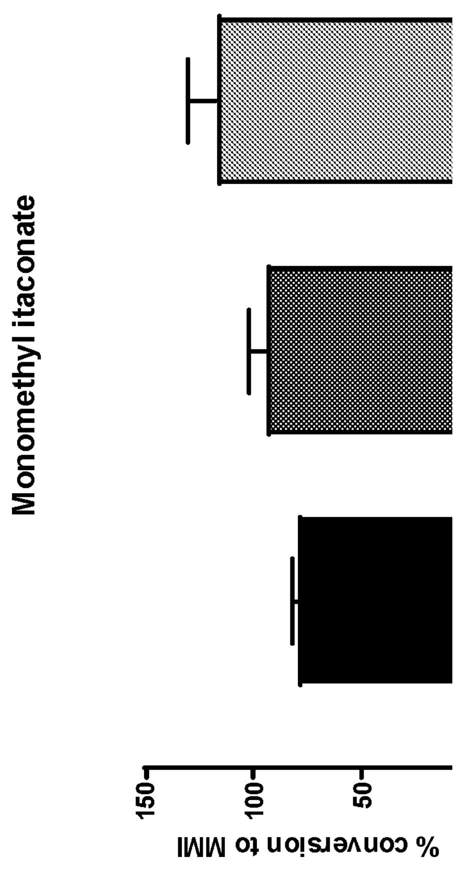
Figure 2:
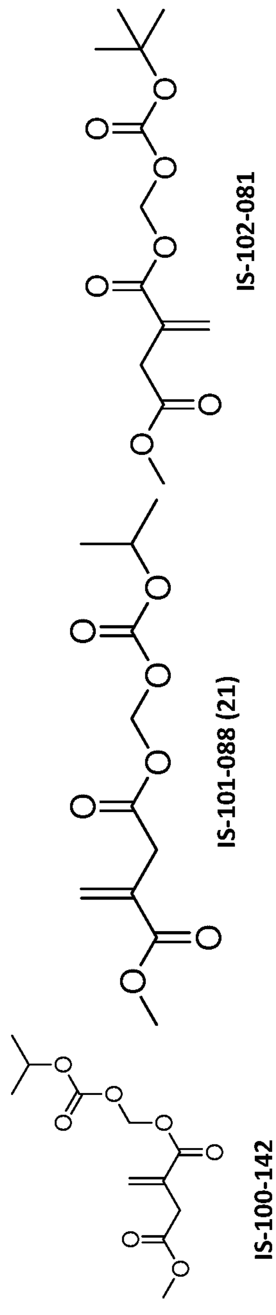
Figure 3:
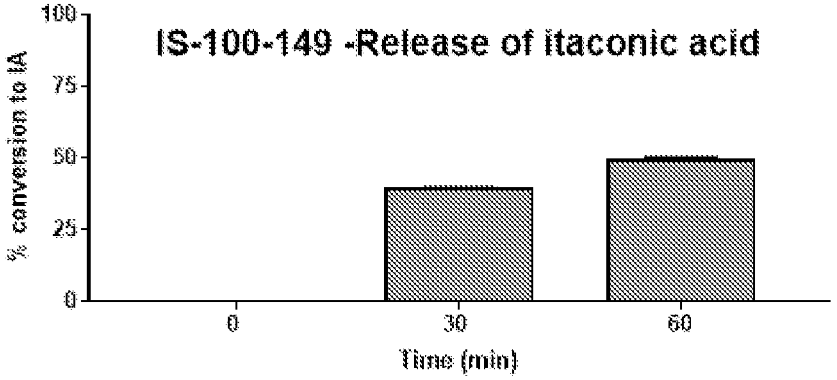
Figure 3:
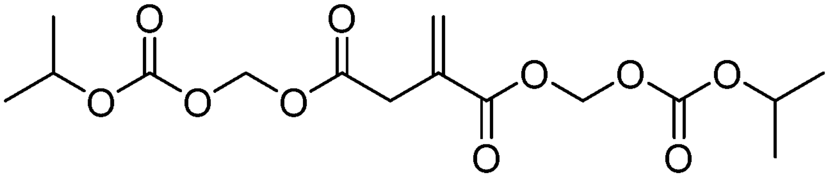

Having thus described the presently disclosed subject matter in general terms, reference will now be made to the accompanying Figures, which are not necessarily drawn to scale, and wherein:

FIG. 1 shows mouse plasma stability for representative prodrugs;

FIG. 2 shows the release of active monomethyl itaconate (in plasma) from representative prodrugs; and FIG. 3 shows the release of active itaconic acid (in plasma) from representative prodrugs.

DETAILED DESCRIPTION

The presently disclosed subject matter now will be described more fully hereinafter with reference to the accompanying Figures, in which some, but not all embodiments of the inventions are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Figures. Therefore, it is to be understood that the presently disclosed subject matter is not to be limited to the specific embodiments disclosed and that modifications and other embodiments are intended to be included within the scope of the appended claims.

I. Novel Prodrugs of Itaconate and Methyl Itaconate

Inflammatory macrophages show substantial accumulation of itaconate, which has been shown to exert profound anti-inflammatory activity by inhibiting succinate dehydrogenase and inducing electrophilic stress that activates NRF2-dependent antioxidant responses. Given its charged nature, however, itaconate itself does not exhibit good pharmacokinetic or cell permeating properties. Given the profound therapeutic potential of administering exogenous itaconate, the presently disclosed subject matter provides prodrugs of both itaconic acid and 1- and 4-methyl itaconic acid, which have the ability to achieve enhanced cell permeation and liberate active itaconic acid and the respective methyl itaconate following oral, systemic or topical/local administration. The presently disclosed prodrugs also exert anti-inflammatory effects on keratinocytes.

A. Representative Compounds of Formula (I)

In some embodiments, the presently disclosed subject matter provides a compound of formula (I):

(I)

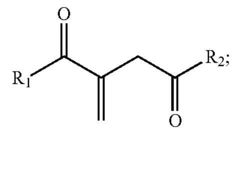

wherein:

$R_1$ and $R_2$ can be the same or different and are each independently selected from one or more of the following and combinations thereof:

(a) —$OR_3$, wherein $R_3$ is H or $C_1$-$C_6$ straight-chain or branched unsubstituted or substituted alkyl;

(b)

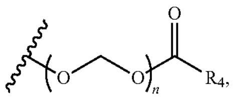

wherein n is an integer selected from 1, 2, 3, and 4; $R_4$ is $C_1$-$C_6$ straight-chain or branched unsubstituted or substituted alkyl or —$OR_5$, wherein $R_5$ is $C_1$-$C_6$ straight-chain or branched unsubstituted or substituted alkyl;

(c)

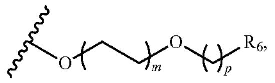

wherein m is an integer selected from 1, 2, 3, and 4; p is an integer selected from 1, 2, 3, 4, 5, 6, 7, 8, 9, 10, 11, 12, 13, 14, 15, 16, 17, 18, 19, and 20; and $R_6$ is $C_1$-$C_6$ straight-chain or branched unsubstituted or substituted alkyl;

(d)

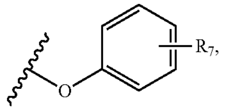

wherein $R_7$ is selected from:

(i) —C(═O)—O—$R_8$, wherein $R_8$ is $C_1$-$C_6$ straight-chain or branched unsubstituted or substituted alkyl;

(ii)

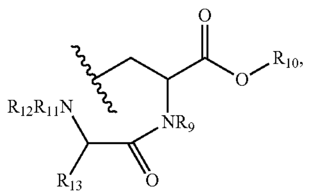

wherein $R_9$ is H or $C_1$-$C_4$ straight-chain or branched unsubstituted or substituted alkyl; $R_{10}$ is $C_1$-$C_6$ straight-chain or branched unsubstituted or substituted alkyl; $R_{11}$ and $R_{12}$ are each independently H or a protecting group; and $R_{13}$ is $C_1$-$C_6$ straight-chain or branched unsubstituted or substituted alkyl;

(iii)

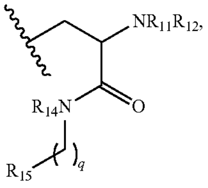

wherein q is an integer selected from 1, 2, 3, 4, 5, 6, 7, 8, 9, and 10; $R_{11}$ and $R_{12}$ are each independently H or a protecting group; $R_{14}$ is H or $C_1$-$C_4$ straightchain or branched unsubstituted or substituted alkyl; and $R_{15}$ is $C_1$-$C_6$ straight-chain or branched unsubstituted or substituted alkyl; and (iv)

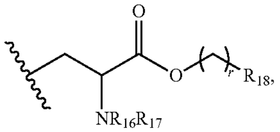

wherein $R_{16}$ and $R_{17}$ are each independently selected from H, $C_1$-$C_4$ straight-chain or branched unsubstituted or substituted alkyl, and a protecting group; $R_{18}$ is aryl;

(e)

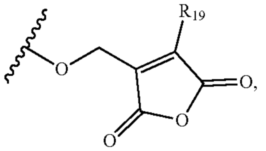

wherein $R_{19}$ is $C_1$-$C_4$ straight-chain or branched unsubstituted or substituted alkyl;

(f)

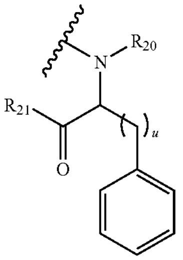
, wherein u is an integer selected from 1, 2, 3, and 4; $R_{20}$ is H or $C_1$-$C_4$ straight-chain or branched unsubstituted or substituted alkyl; and $R_{21}$ is —$OR_{22}$, wherein $R_{22}$ is $C_1$-$C_6$ straightchain or branched unsubstituted or substituted alkyl or —$NR_{23}R_{24}$, wherein $R_{23}$ and $R_{24}$ are each independently H or $C_1$-$C_4$ straightchain or branched unsubstituted or substituted alkyl;

provided that $R_1$ and $R_2$ cannot both be —OH or both be —$OR_3$ at the same time;

and pharmaceutically acceptable salts thereof.

In certain embodiments of the compound of formula (I):
(a) $R_1$ is $—OR_3$ and $R_2$ is selected from $—OR_3$,
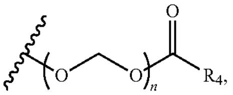
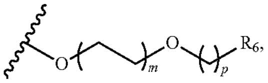
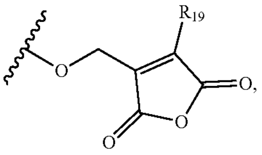
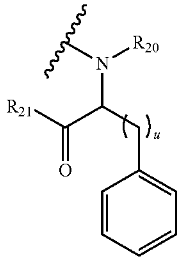
, and
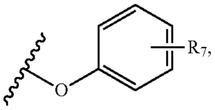
wherein $R_7$ is selected from $—C(═O)—O—R_8$,
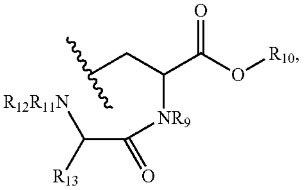
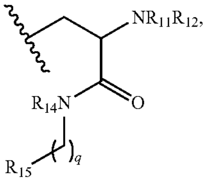
and
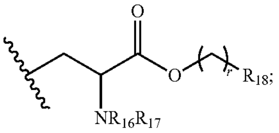
(b) $R_1$ is
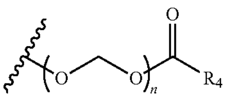
and $R_2$ is selected from $—OR_3$,
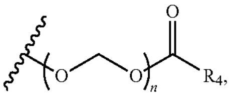
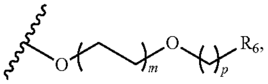
-continued
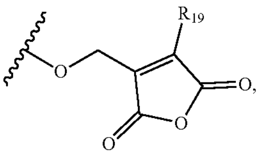
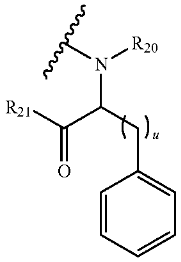
, and
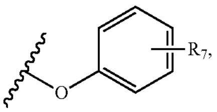
wherein $R_7$ is selected from $—C(═O)—O—R_8$,
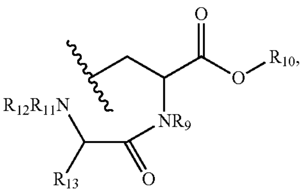
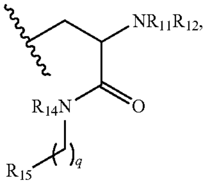
and
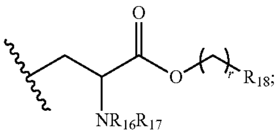
(c) $R_1$ is
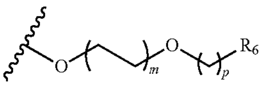
and $R_2$ is selected from $—OR_3$,
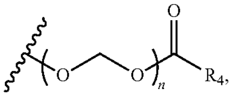
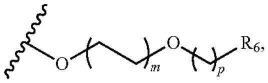

-continued
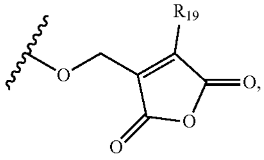
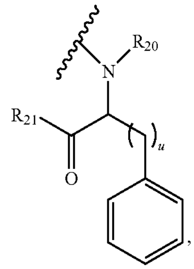
and
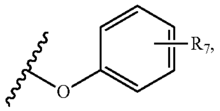
wherein $R_7$ is selected from —C(=O)—O—$R_8$,
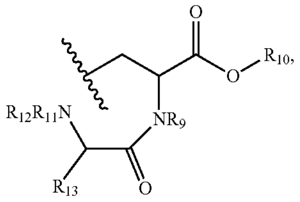
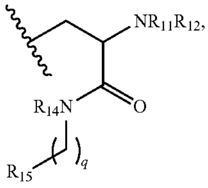
and
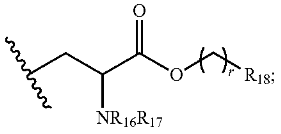
(d) $R_1$ is
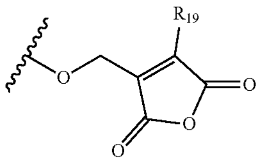
and $R_2$ is selected from —$OR_3$,
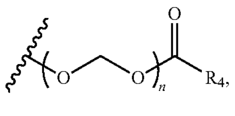
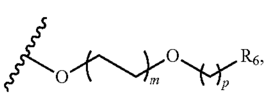
-continued
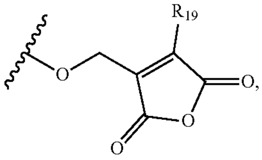
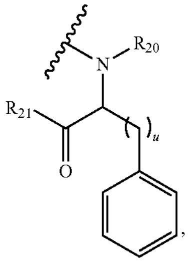
and
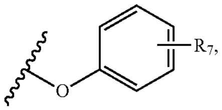
wherein $R_7$ is selected from —C(=O)—O—$R_8$,
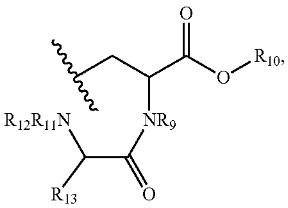
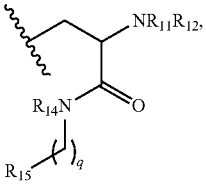
and
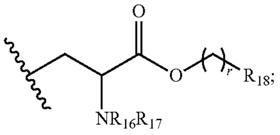
(e) $R_1$ is
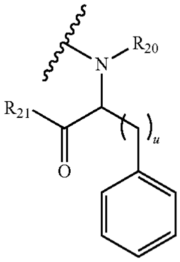
and $R_2$ is selected from —$OR_3$,
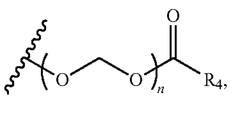
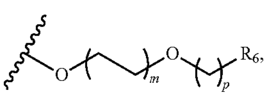

-continued
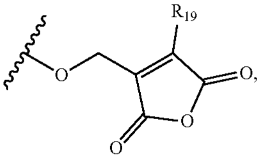
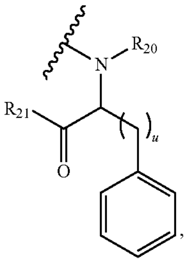
, and
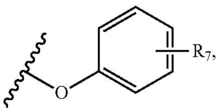
wherein $R_7$ is selected from —C(═O)—O—$R_8$,
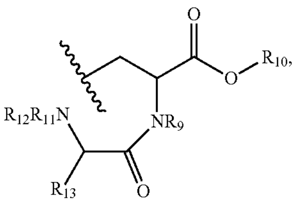
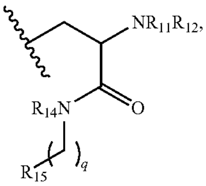
and
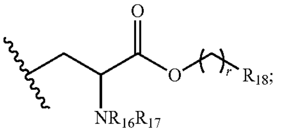
(f) $R_1$ is
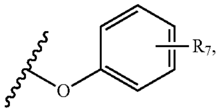
wherein $R_7$ is —C(═O)—O—$R_8$ and $R_2$ is selected from —$OR_3$,
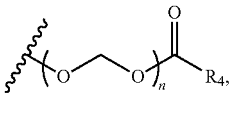
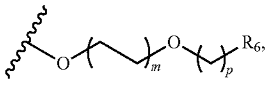
-continued
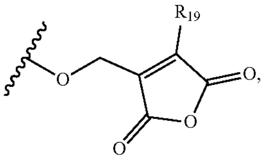
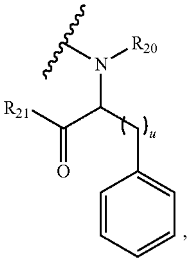
, and
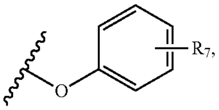
wherein $R_7$ is selected from —C(═O)—O—$R_8$,
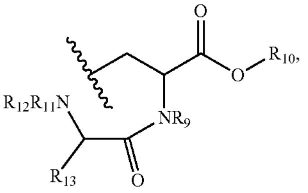
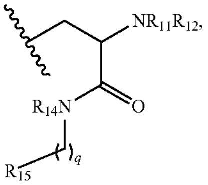
and
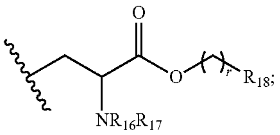
(g) $R_1$ is
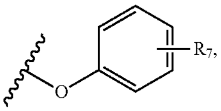
wherein $R_7$ is
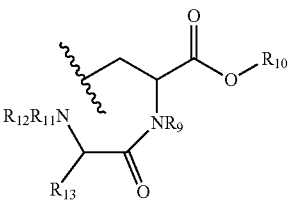

and $R_2$ is selected from $—OR_3$,
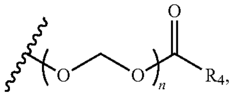 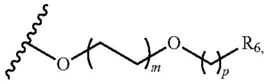
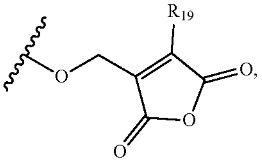 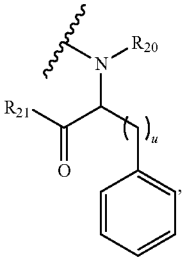 and
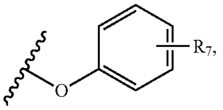
wherein $R_7$ is selected from $—C(=O)—O—R_8$,
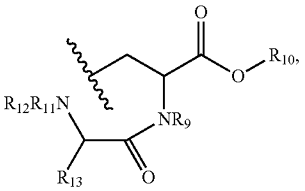
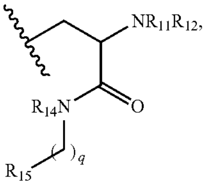 and
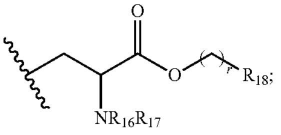
(h) $R_1$ is
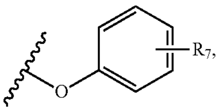
wherein $R_7$ is
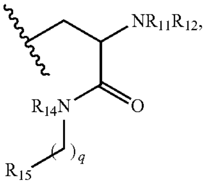
and $R_2$ is selected from $—OR_3$,
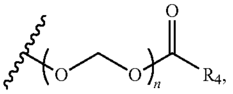 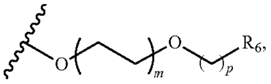
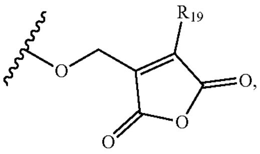 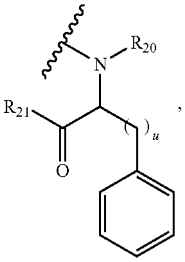 and
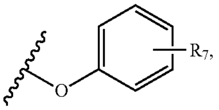
wherein $R_7$ is selected from $—C(=O)—O—R_8$,
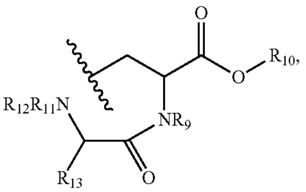
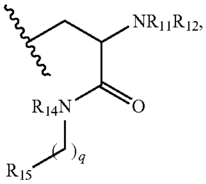 and
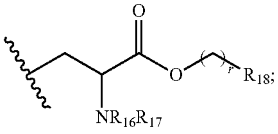
and
(i) $R_1$ is
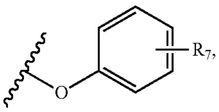
wherein $R_7$ is
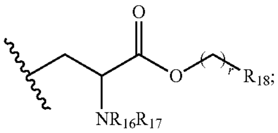

and $R_2$ is selected from $-OR_3$,

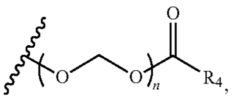, 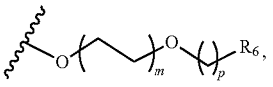,

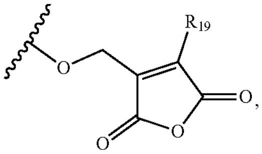, 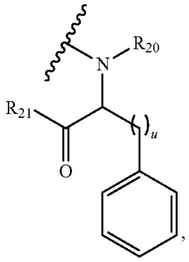, and 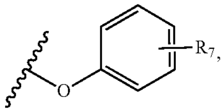, wherein $R_7$ is selected from $-C(=O)-O-R_8$,

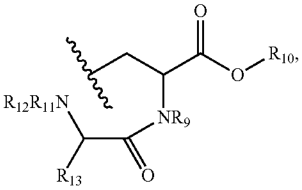,

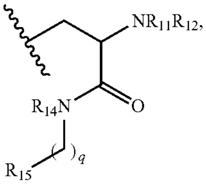, and

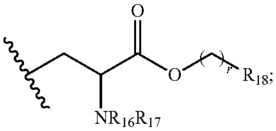;

provided that $R_1$ and $R_2$ cannot both be $-OH$ or both be $-OR_3$ at the same time; and pharmaceutically acceptable salts thereof.

In more certain embodiments of the compound of formula (I):

(a-i) $R_1$ is $-OH$ and $R_2$ is selected from:

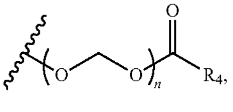, 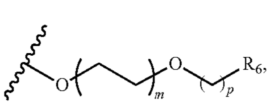,

-continued

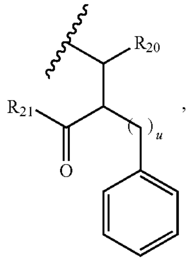, and 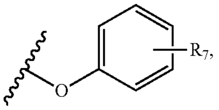, wherein $R_7$ is $-C(=O)-O-R_8$;

(a-ii) $R_1$ is $-OR_3$ and $R_2$ is selected from:

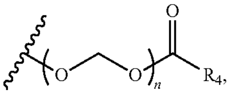, 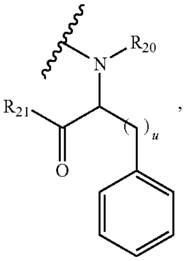, and

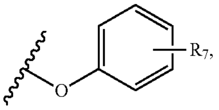, wherein $R_7$ is selected from $-C(=O)-O-R_8$,

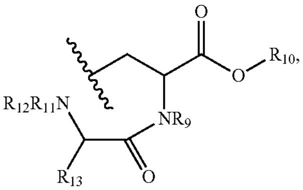,

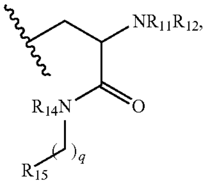, and

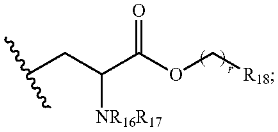;

(b) $R_1$ is

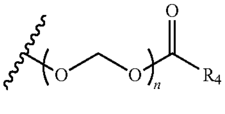

and $R_2$ is selected from: —$OR_3$,
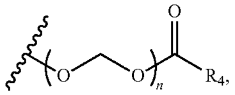
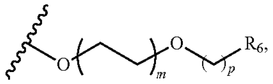
and
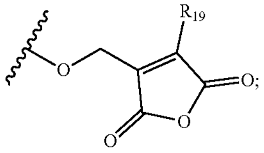
(c) $R_1$ is
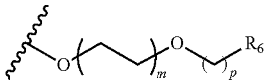
and $R_2$ is —$OR_3$;
(d) $R_1$ is
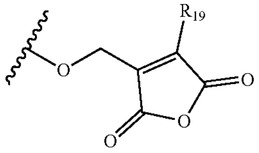
and $R_2$ is selected from: —$OR_3$ and
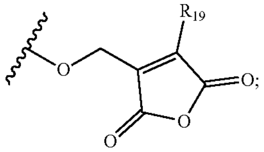
(e) $R_1$ is
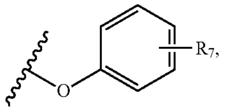
wherein $R_7$ is —C(═O)—O—$R_8$ and $R_2$ is —$OR_3$;
(f) $R_1$ is
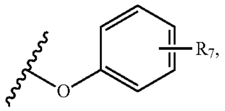
wherein $R_7$ is
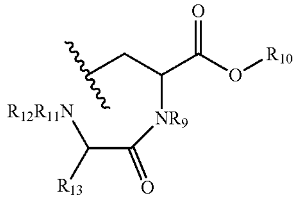
and $R_2$ is —$OR_3$;
(g) $R_1$ is
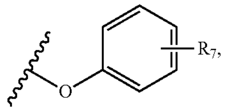
wherein $R_7$ is
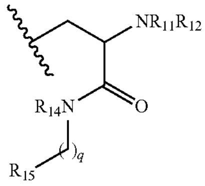
and $R_2$ is —$OR_3$;
(h) $R_1$ is
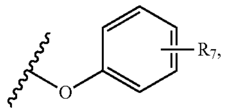
wherein $R_7$ is
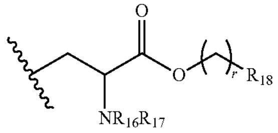
and $R_2$ is —$OR_3$; and
(i) $R_1$ is
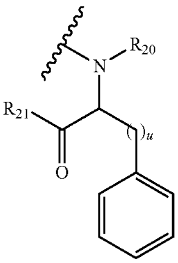
and $R_2$ is —$OR_3$.

In some embodiments of the compound of formula (I), $R_3$, $R_4$, $R_5$, $R_6$, $R_8$, $R_9$, $R_{10}$, $R_{13}$, $R_{15}$, and $R_{22}$ can each independently be a $C_1$, $C_2$, $C_3$, $C_4$, $C_5$, or $C_6$ straight-chain or branched unsubstituted or substituted alkyl selected from methyl, ethyl, n-propyl, isopropyl, n-butyl, sec-butyl, iso-butyl, t-butyl, pentyl, isopentyl, neopentyl, n-hexyl, 2-methylpentane, 3-methylpentane, 2,2-dimethylbutane, and 2,3-dimethylbutane.

In some embodiments of the compound of formula (I), $R_9$, $R_{14}$, $R_{16}$, $R_{17}$, $R_{19}$, $R_{20}$, $R_{23}$, and $R_{24}$ can each independently be a $C_1$. $C_2$, $C_3$, or $C_4$ straight-chain or branched unsubstituted or substituted alkyl selected from methyl, ethyl, n-propyl, isopropyl, n-butyl, sec-butyl, iso-butyl, and t-butyl.

Representative substituent groups include, but are not limited to, alkyl, substituted alkyl, halogen, aryl, substituted aryl, alkoxyl, hydroxyl, nitro, amino, alkylamino, dialkylamino, sulfate, cyano, mercapto, and alkylthio.

In certain embodiments of the compound of formula (I), the protecting group is selected from tert-butoxycarbonyl (boc), carbobenzyloxy (Cbz), p-Methoxybenzyl carbonyl (Moz or MeOZ), 9-fluorenylmethyloxycarbonyl (Fmoc) group, benzyl (Bn), p-methoxybenzyl (PMB), 3,4-dimethoxybenzyl (DMPM), tosyl (Ts), Troc (trichloroethyl chloroformate), (4-nitrophenyl)sulfonyl (Nosyl), and nitrophenylsulfenyl (Nps). In particular embodiments, the protecting group is tert-butoxycarbonyl (boc).

In some embodiments of the compound of formula (I), $R_{18}$ is selected from phenyl.

In certain embodiments of the compound of formula (I):

(a-i) $R_1$ is —OH and $R_2$ is selected from:

(2)

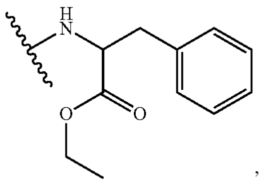

, (8)

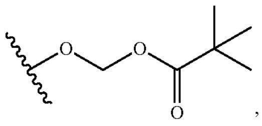

, (22)

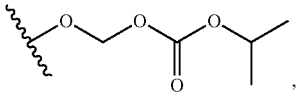

, (30)

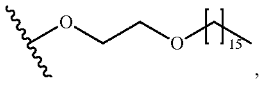

, and (33)

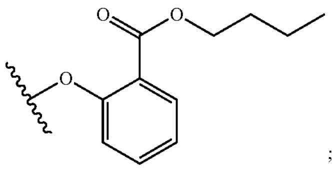

;

(7, 9, 23)

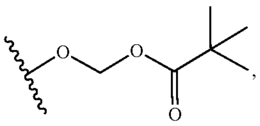

(21)

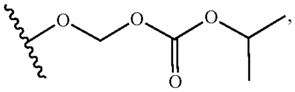

(25)

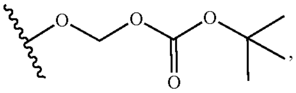

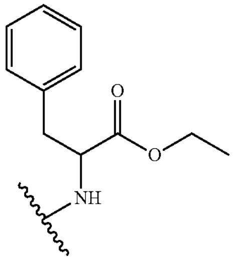

, (26)

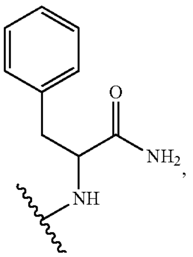

(28)

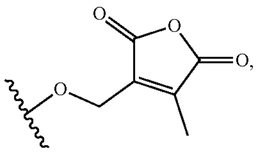

(29)

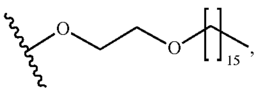

(31)

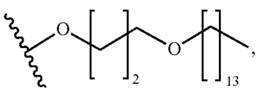

(32)

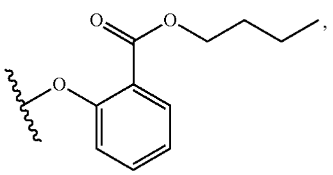

(34)

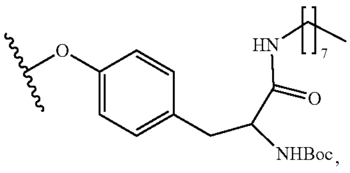

(a-ii) $R_1$ is selected from $—OCH_3$, $—OCH(CH_3)_2$, and $—OC(CH_3)_3$ and $R_2$ is selected from:

-continued
(35)
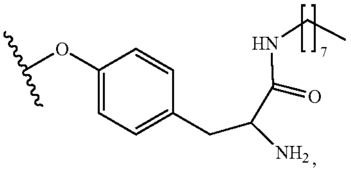
(36)
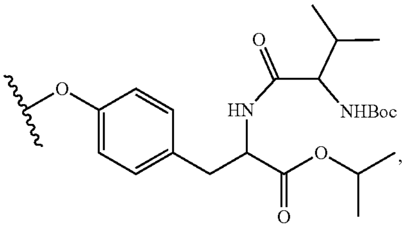
(37)
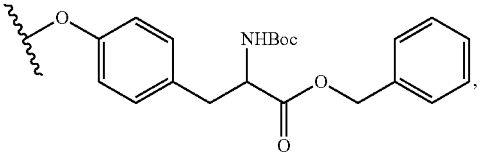
, and
(38)
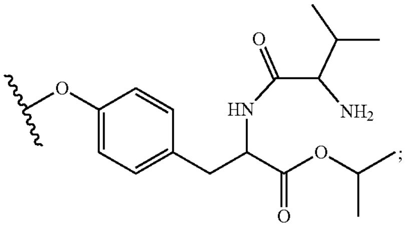
(b) $R_1$ is
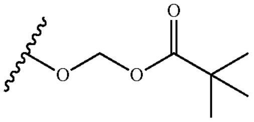
or
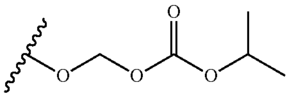
and $R_2$ is —$OCH_3$ (5, 6) or
(10)
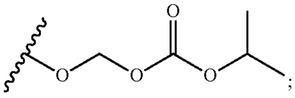
(c) $R_1$ is
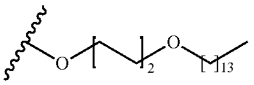
or
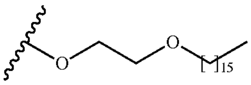
and $R_2$ is —$OCH_3$ (12, 13);
(d) $R_1$ is
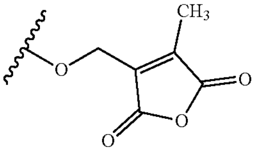 [SMILES: *OCC1=C(C)C(=O)OC1=O]
and $R_2$ is selected from: —$OCH_3$ (11) and
(27)
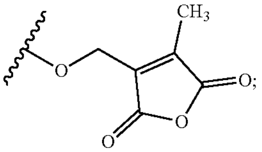
(e) $R_1$ is
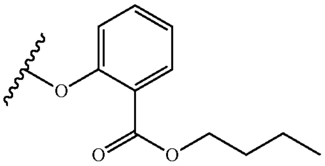 [SMILES: *Oc1ccccc1C(=O)OCCCC]
and $R_2$ is —$OCH_3$ (14);
(f) $R_1$ is
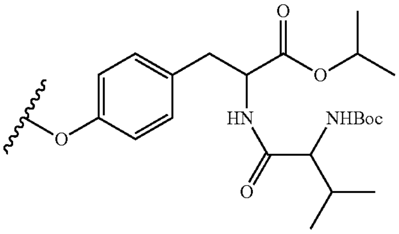
or
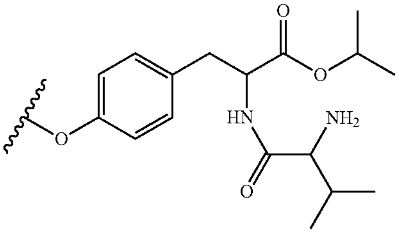
and $R_2$ is —$OCH_3$ (17, 19);
(g) $R_1$ is
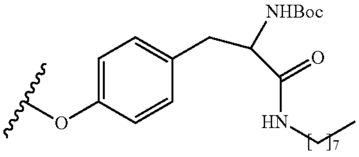
or -continued
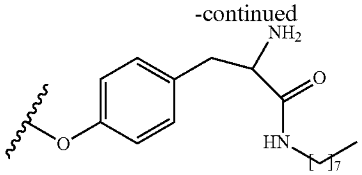
and $R_2$ is —$OCH_3$ (15, 16);
(h) $R_1$ is
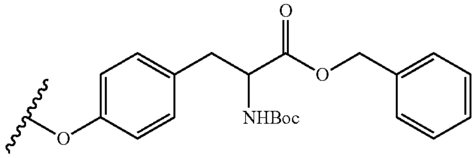
or
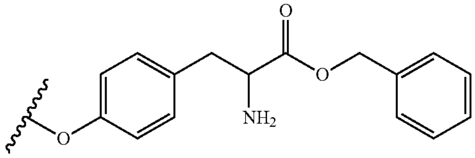
and $R_2$ is $OCH_3$ (18, 20); and
(i) $R_1$ is
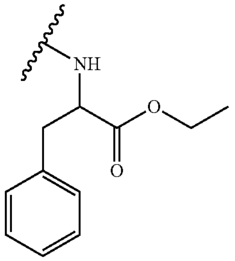
or
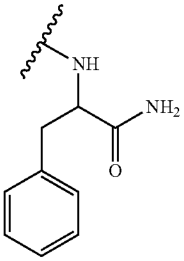
and $R_2$ is —$OCH_3$ (3, 4).
In particular embodiments of the compound of formula (I), the compound is selected from:
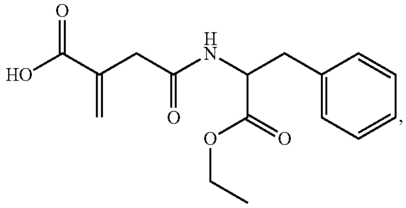
,
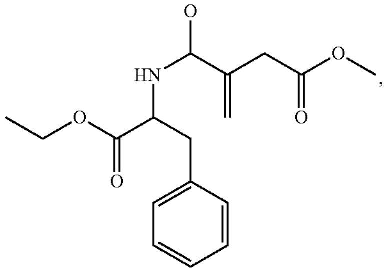
,
-continued
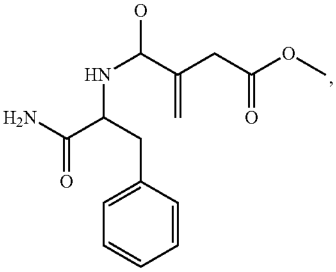
,
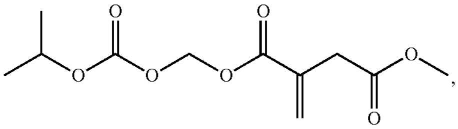
,
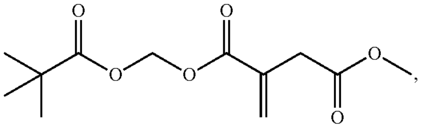
,
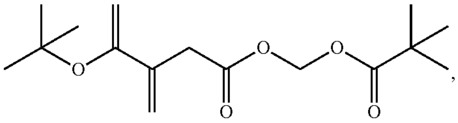
,
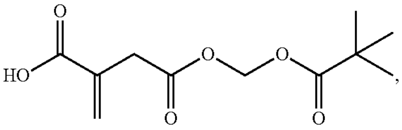
,
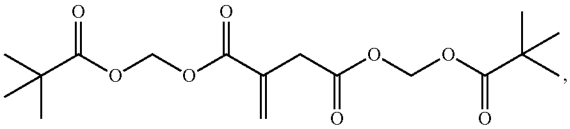
,
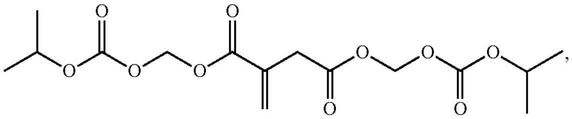
,
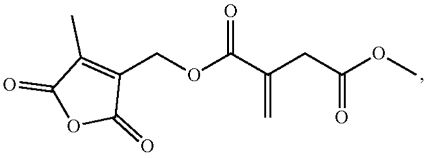
,
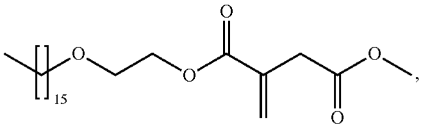
,
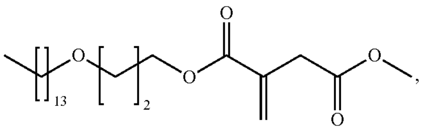
,
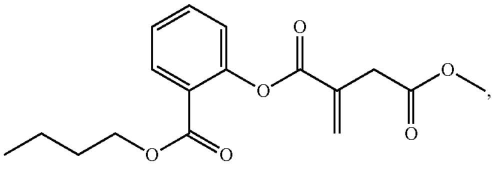
, -continued
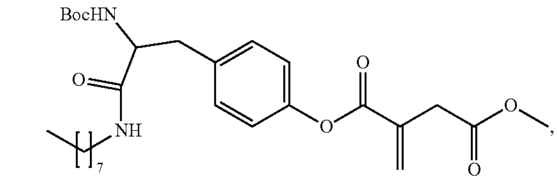
,
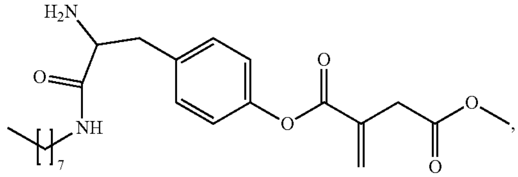
,
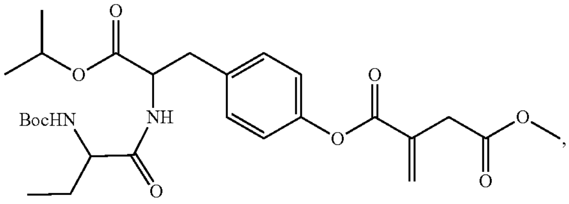
,
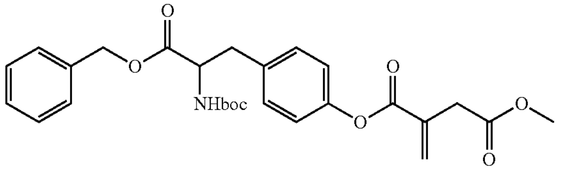
,
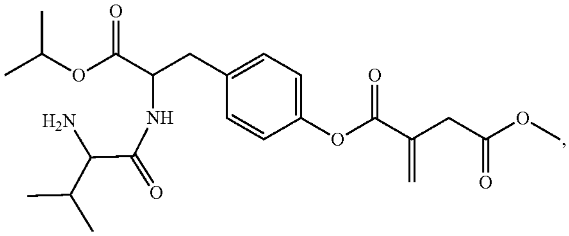
,
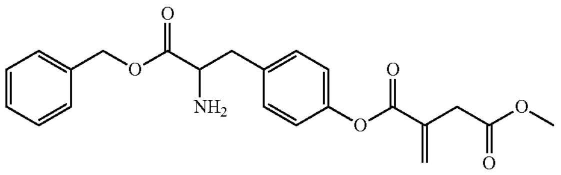
,
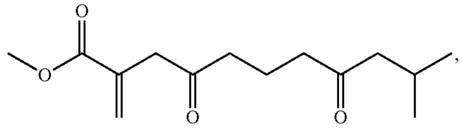
,
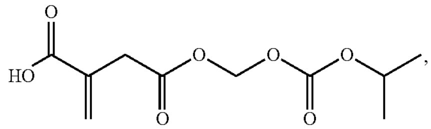
,
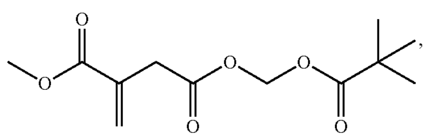
,
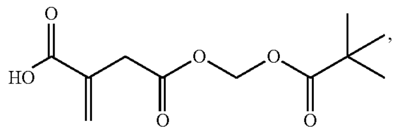
,
-continued
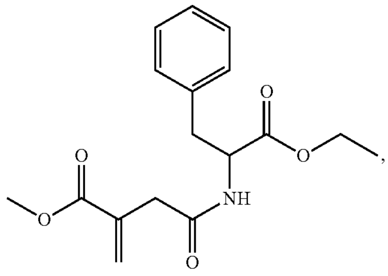
,
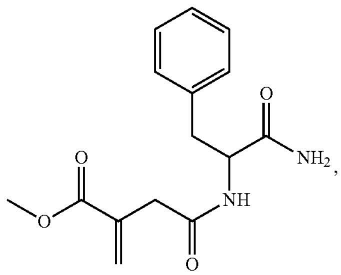
,
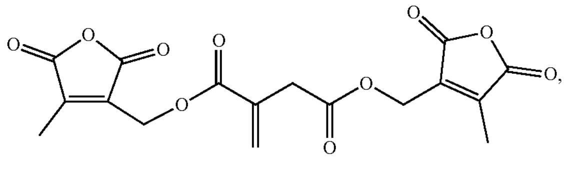
,
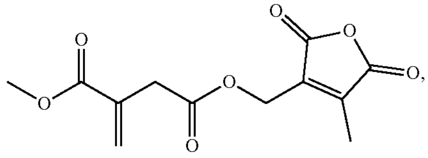
,
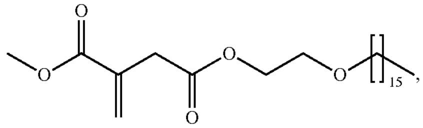
,
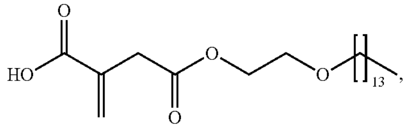
,
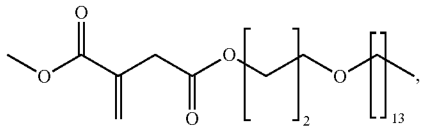
,
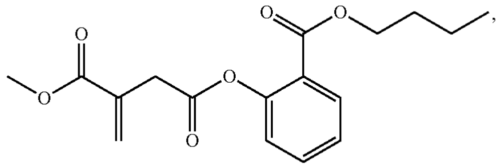
,
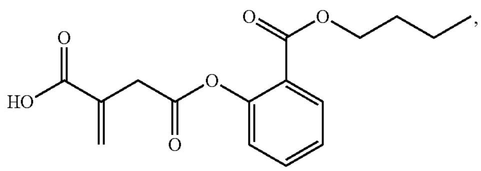
, -continued

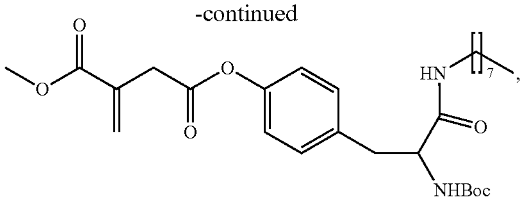

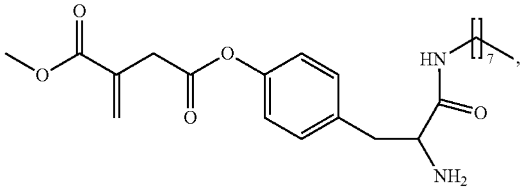

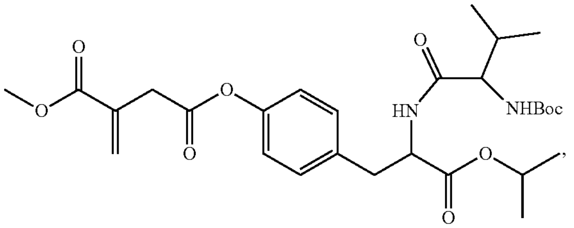

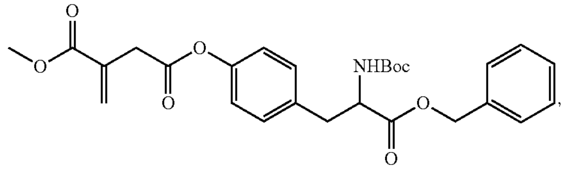

-continued

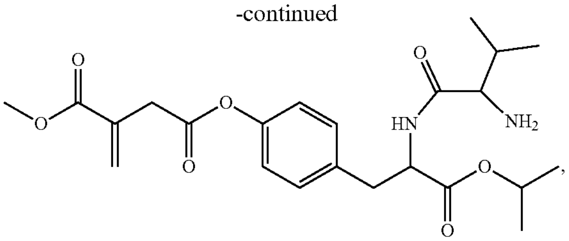

and

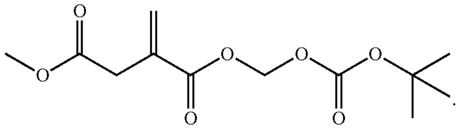

In certain embodiments, the compound of formula (I) is comprises a pharmaceutically acceptable salt. In some embodiments, the pharmaceutically acceptable salt is an acid salt. In particular embodiments, the pharmaceutically acceptable salt is trifluoroacetate (TEA).

Representative compounds of formula (I) and the active agent released by each respective prodrug are provided in Table 1.

TABLE 1
Itaconic Acid and Methyl Itaconate Prodrugs
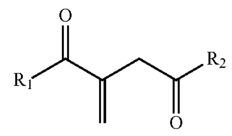
| Cmpd | Structure | Moiety Released | $R_1$ | $R_2$ |
|---|---|---|---|---|
| Itaconic Acid (1) | 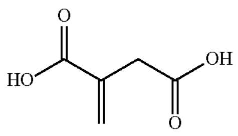 | | HO— | —OH |
| IS-100-127 (2) | 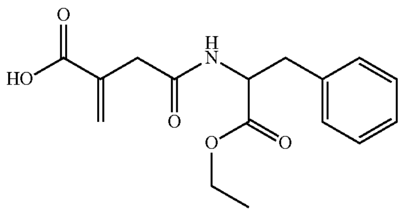 [SMILES: C=C(CC(=O)NC(Cc1ccccc1)C(=O)OCC)C(=O)O] | Itaconate | HO— | 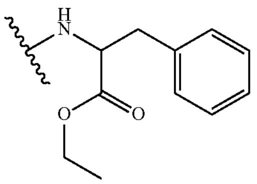 [SMILES: *NC(Cc1ccccc1)C(=O)OCC] |
| 1S0100-128 (3) | 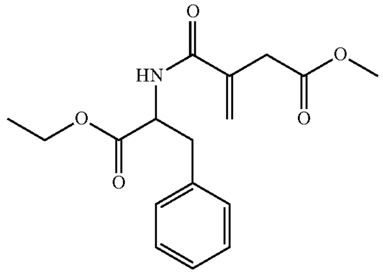 [SMILES: C=C(CC(=O)OC)C(=O)NC(Cc1ccccc1)C(=O)OCC] | 4-MI† | 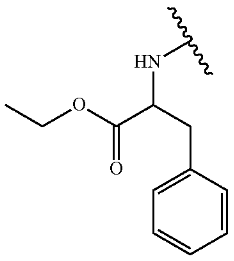 [SMILES: *NC(Cc1ccccc1)C(=O)OCC] | —$OCH_3$ |

TABLE 1-continued
Itaconic Acid and Methyl Itaconate Prodrugs
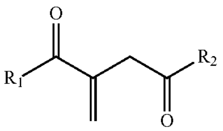
| Cmpd | Structure | Moiety Released | $R_1$ | $R_2$ |
|---|---|---|---|---|
| IS-100-129 (4) | 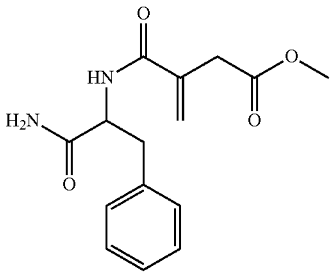 [SMILES: C=C(CC(=O)OC)C(=O)NC(Cc1ccccc1)C(N)=O] | 4-MI | 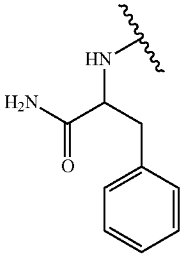 [SMILES: *NC(Cc1ccccc1)C(N)=O] | $—OCH_3$ |
| IS-100-142 (5) | 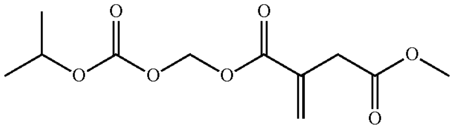 [SMILES: C=C(CC(=O)OC)C(=O)OCOC(=O)OC(C)C] | 4-MI | 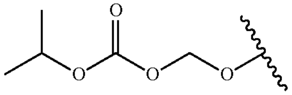 [SMILES: *OCOC(=O)OC(C)C] | $—OCH_3$ |
| IS-100-143 (6) | 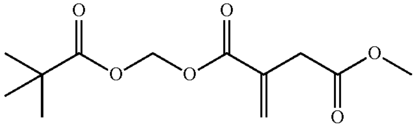 [SMILES: C=C(CC(=O)OC)C(=O)OCOC(=O)C(C)(C)C] | 4-MI | 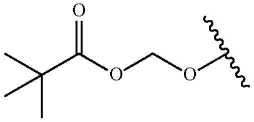 | $—OCH_3$ |
| IS-100-146 (7) | 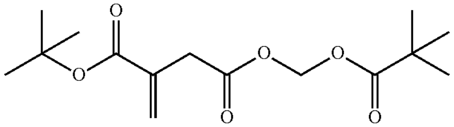 [SMILES: C=C(CC(=O)OCOC(=O)C(C)(C)C)C(=O)OC(C)(C)C] | Itaconate | 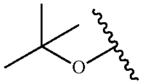 [SMILES: *OC(C)(C)C] | 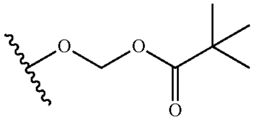 [SMILES: *OCOC(=O)C(C)(C)C] |
| IS-100-147 (8) | 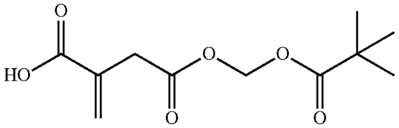 [SMILES: C=C(CC(=O)OCOC(=O)C(C)(C)C)C(=O)O] | Itaconate | HO— | 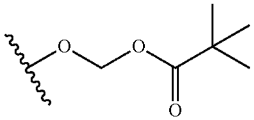 [SMILES: *OCOC(=O)C(C)(C)C] |

TABLE 1-continued
Itaconic Acid and Methyl Itaconate Prodrugs
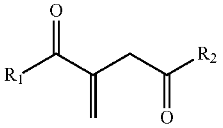
| Cmpd | Structure | Moiety Released | $R_1$ | $R_2$ |
|---|---|---|---|---|
| IS-100-148 (9) | 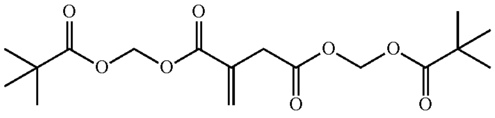 [SMILES: C=C(CC(=O)OCOC(=O)C(C)(C)C)C(=O)OCOC(=O)C(C)(C)C] | Itaconate | 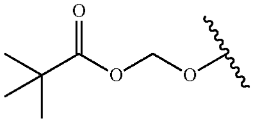 [SMILES: *OCOC(=O)C(C)(C)C] | 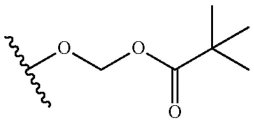 [SMILES: *OCOC(=O)C(C)(C)C] |
| IS-100-149 (10) | 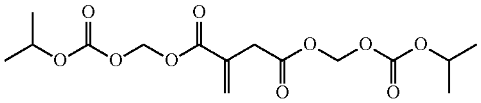 | Itaconate | 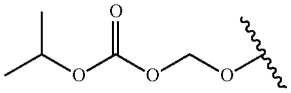 [SMILES: *OCOC(=O)OC(C)C] | 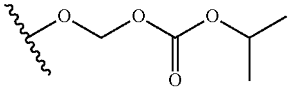 [SMILES: *OCOC(=O)OC(C)C] |
| LTP-1025 (11) | 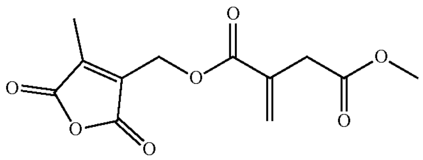 [SMILES: C=C(CC(=O)OC)C(=O)OCC1=C(C)C(=O)OC1=O] | 4-MI | 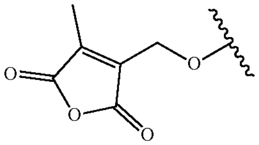 [SMILES: *OCC1=C(C)C(=O)OC1=O] | $—OCH_3$ |
| MK-933 (12) | 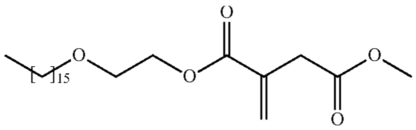 | 4-MI | 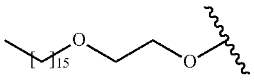 | $—OCH_3$ |
| MK-937 (13) | 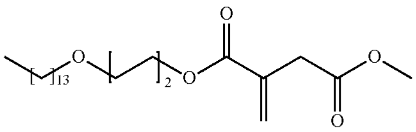 | 4-MI | 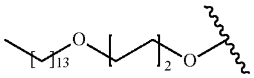 | $—OCH_3$ |

TABLE 1-continued
Itaconic Acid and Methyl Itaconate Prodrugs
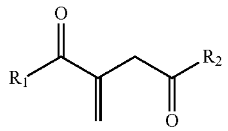
| Cmpd | Structure | Moiety Released | $R_1$ | $R_2$ |
| --- | --- | --- | --- | --- |
| MK-939 (14) | 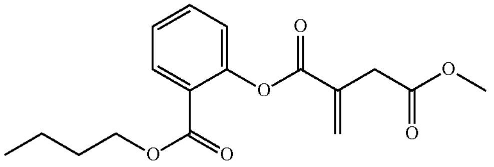 [SMILES: C=C(CC(=O)OC)C(=O)Oc1ccccc1C(=O)OCCCC] | 4-MI | 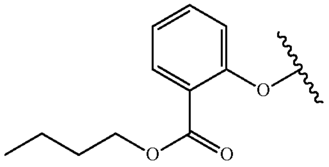 [SMILES: *Oc1ccccc1C(=O)OCCCC] | —$OCH_3$ |
| MK-940 (15) | 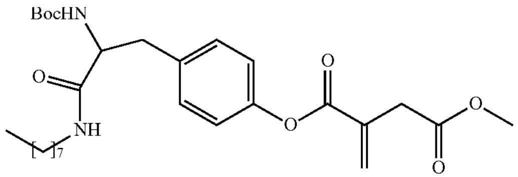 | 4-MI | 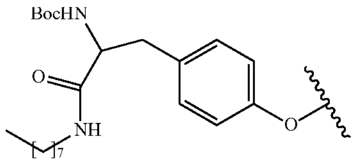 | —$OCH_3$ |
| MK-941 (16) | 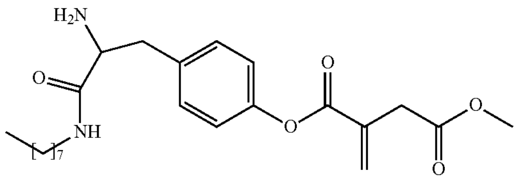 | 4-MI | 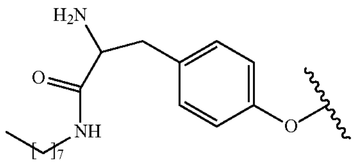 | —$OCH_3$ |
| MK-942 (17) | 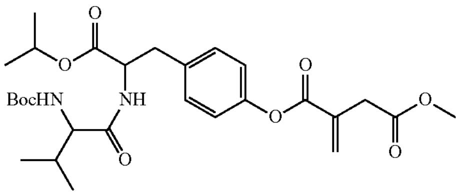 [SMILES: C=C(CC(=O)OC)C(=O)Oc1ccc(CC(NC(=O)C(NC(=O)OC(C)(C)C)C(C)C)C(=O)OC(C)C)cc1] | 4-MI | 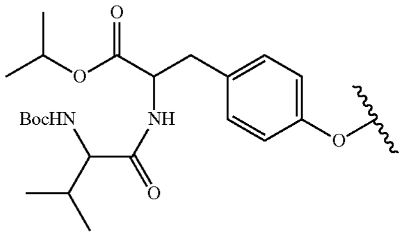 [SMILES: *Oc1ccc(CC(NC(=O)C(NC(=O)OC(C)(C)C)C(C)C)C(=O)OC(C)C)cc1] | —$OCH_3$ |

TABLE 1-continued
Itaconic Acid and Methyl Itaconate Prodrugs
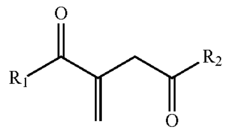
| Cmpd | Structure | Moiety Released | $R_1$ | $R_2$ |
| --- | --- | --- | --- | --- |
| MK-943 (18) | 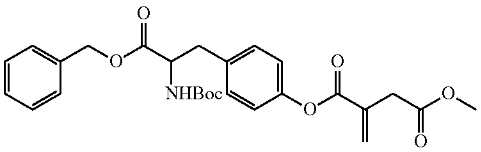 [SMILES: C=C(CC(=O)OC)C(=O)Oc1ccc(CC(NC(=O)OC(C)(C)C)C(=O)OCc2ccccc2)cc1] | 4-MI | 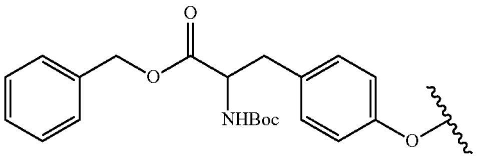 [SMILES: *Oc1ccc(CC(NC(=O)OC(C)(C)C)C(=O)OCc2ccccc2)cc1] | $—OCH_3$ |
| MK-944 (19) | 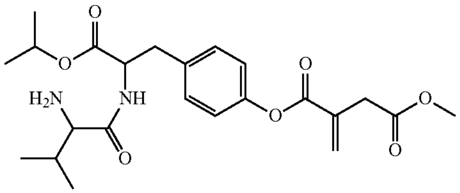 [SMILES: C=C(CC(=O)OC)C(=O)Oc1ccc(CC(NC(=O)C(N)C(C)C)C(=O)OC(C)C)cc1] | 4-MI | 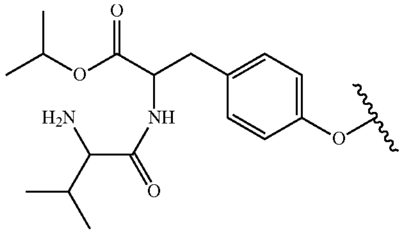 [SMILES: *Oc1ccc(CC(NC(=O)C(N)C(C)C)C(=O)OC(C)C)cc1] | $—OCH_3$ |
| MK-945 (20) | 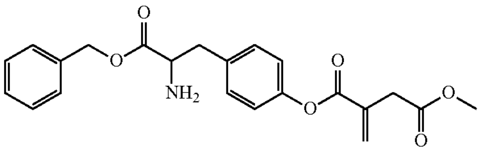 [SMILES: C=C(CC(=O)OC)C(=O)Oc1ccc(CC(N)C(=O)OCc2ccccc2)cc1] | 4-MI | 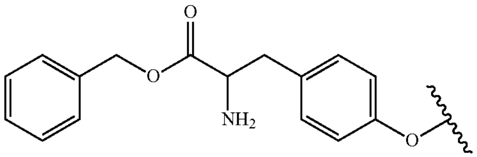 [SMILES: *Oc1ccc(CC(N)C(=O)OCc2ccccc2)cc1] | $—OCH_3$ |
| IS-101-088 (21) | 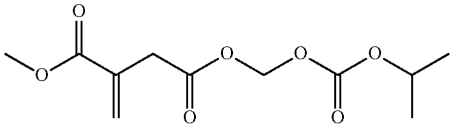 [SMILES: C=C(CC(=O)OCOC(=O)OC(C)C)C(=O)OC] | 1-MI‡ | $CH_3O—$ | 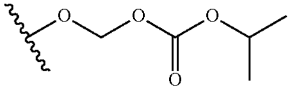 [SMILES: *OCOC(=O)OC(C)C] |
| 22 | 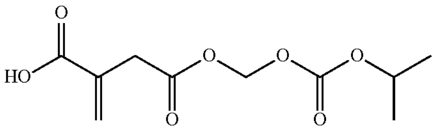 [SMILES: C=C(CC(=O)OCOC(=O)OC(C)C)C(=O)O] | Itaconate | HO— | 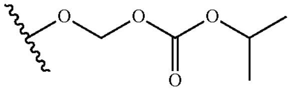 [SMILES: *OCOC(=O)OC(C)C] |

TABLE 1-continued
Itaconic Acid and Methyl Itaconate Prodrugs
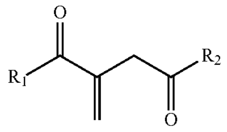
| Cmpd | Structure | Moiety Released | $R_1$ | $R_2$ |
|---|---|---|---|---|
| IS-101-089 (23) | 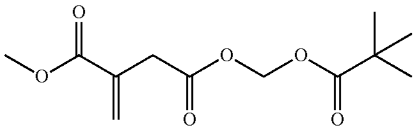 [SMILES: C=C(CC(=O)OCOC(=O)C(C)(C)C)C(=O)OC] | 1-MI | $CH_3O$— | 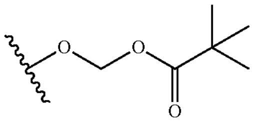 [SMILES: *OCOC(=O)C(C)(C)C] |
| 25 | 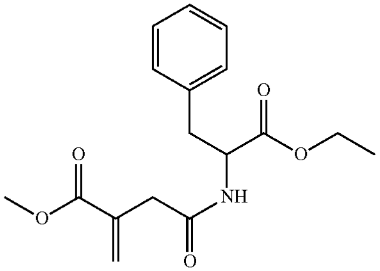 [SMILES: C=C(CC(=O)NC(Cc1ccccc1)C(=O)OCC)C(=O)OC] | 1-MI | $CH_3O$— | 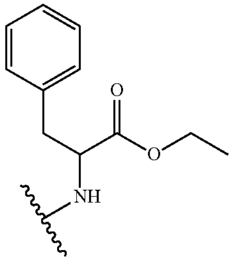 [SMILES: *NC(Cc1ccccc1)C(=O)OCC] |
| 26 | 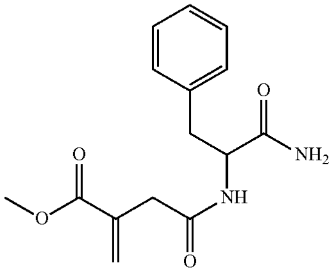 [SMILES: C=C(CC(=O)NC(Cc1ccccc1)C(N)=O)C(=O)OC] | 1-MI | $CH_3O$— | 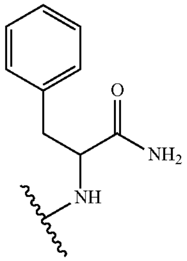 [SMILES: *NC(Cc1ccccc1)C(N)=O] |

TABLE 1-continued
Itaconic Acid and Methyl Itaconate Prodrugs
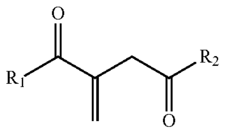
| Cmpd | Structure | Moiety Released | $R_1$ | $R_2$ |
|---|---|---|---|---|
| 27 | 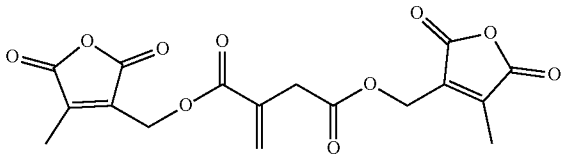 [SMILES: C=C(CC(=O)OCC1=C(C)C(=O)OC1=O)C(=O)OCC1=C(C)C(=O)OC1=O] | Itaconate | 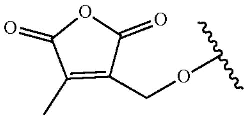 [SMILES: *OCC1=C(C)C(=O)OC1=O] | 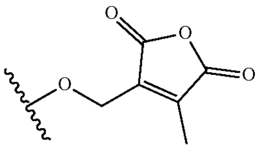 [SMILES: *OCC1=C(C)C(=O)OC1=O] |
| 28 | 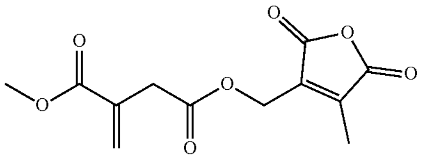 [SMILES: C=C(CC(=O)OCC1=C(C)C(=O)OC1=O)C(=O)OC] | 1-MI | $CH_3O$— | 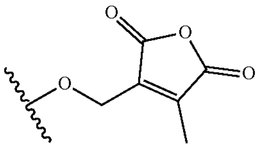 [SMILES: *OCC1=C(C)C(=O)OC1=O] |
| 29 | 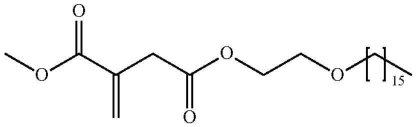 | 1-MI | $CH_3O$— | 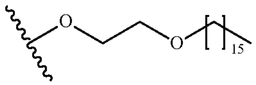 |
| 30 | 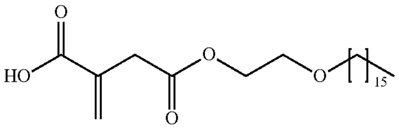 | Itaconate | HO— | 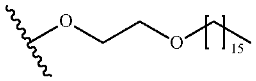 |
| 31 | 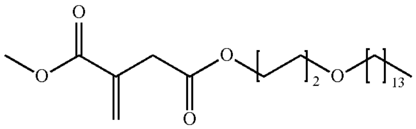 | 1-MI | $CH_3O$— | 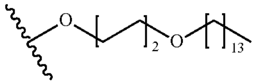 |

TABLE 1-continued
Itaconic Acid and Methyl Itaconate Prodrugs
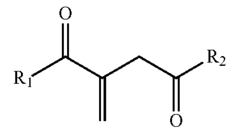
| Cmpd | Structure | Moiety Released | $R_1$ | $R_2$ |
|---|---|---|---|---|
| 32 | 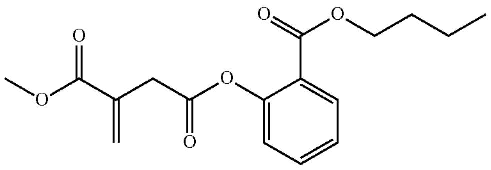 [SMILES: C=C(CC(=O)Oc1ccccc1C(=O)OCCCC)C(=O)OC] | 1-MI | $CH_3O$— | 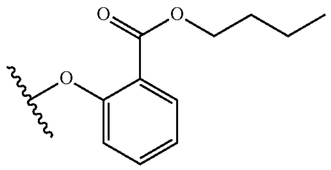 [SMILES: *Oc1ccccc1C(=O)OCCCC] |
| 33 | 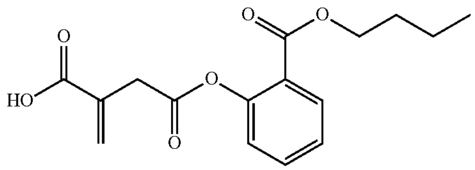 [SMILES: C=C(CC(=O)Oc1ccccc1C(=O)OCCCC)C(=O)O] | Itaconate | HO— | 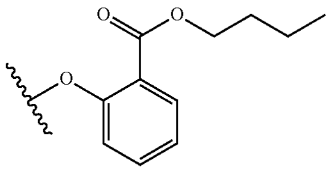 [SMILES: *Oc1ccccc1C(=O)OCCCC] |
| 34 | 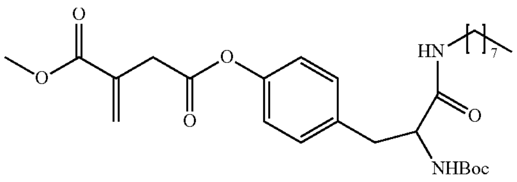 | 1-MI | $CH_3O$— | 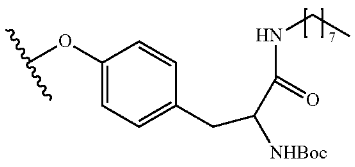 |
| 35 | 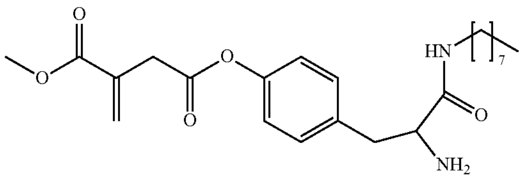 | 1-MI | $CH_3O$— | 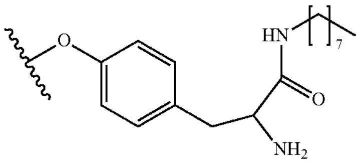 |

TABLE 1-continued
Itaconic Acid and Methyl Itaconate Prodrugs
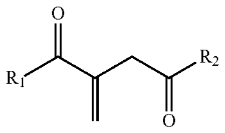
| Cmpd | Structure | Moiety Released | $R_1$ | $R_2$ |
|---|---|---|---|---|
| 36 | 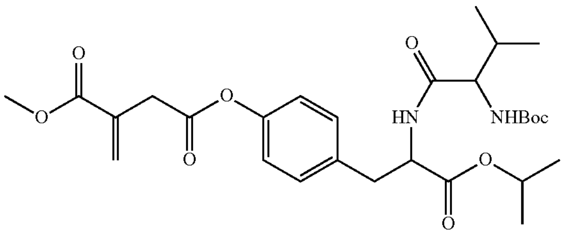 [SMILES: C=C(CC(=O)Oc1ccc(CC(NC(=O)C(NC(=O)OC(C)(C)C)C(C)C)C(=O)OC(C)C)cc1)C(=O)OC] | 1-MI | $CH_3O$— | 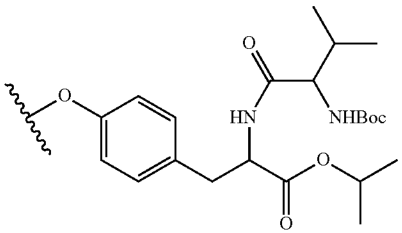 [SMILES: *Oc1ccc(CC(NC(=O)C(NC(=O)OC(C)(C)C)C(C)C)C(=O)OC(C)C)cc1] |
| 37 | 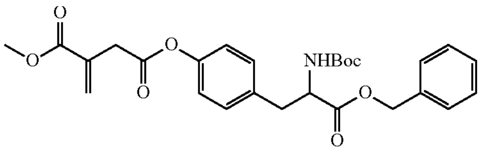 [SMILES: C=C(CC(=O)Oc1ccc(CC(NC(=O)OC(C)(C)C)C(=O)OCc2ccccc2)cc1)C(=O)OC] | 1-MI | $CH_3O$— | 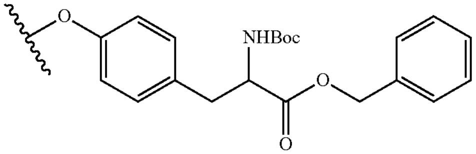 [SMILES: *Oc1ccc(CC(NC(=O)OC(C)(C)C)C(=O)OCc2ccccc2)cc1] |
| 38 | 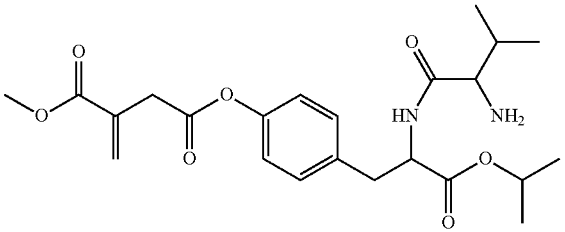 [SMILES: C=C(CC(=O)Oc1ccc(CC(NC(=O)C(N)C(C)C)C(=O)OC(C)C)cc1)C(=O)OC] | 1-MI | $CH_3O$— | 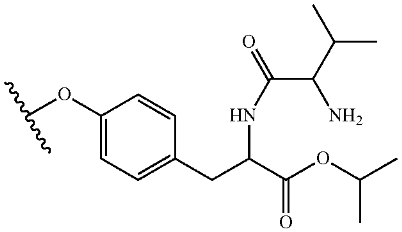 [SMILES: *Oc1ccc(CC(NC(=O)C(N)C(C)C)C(=O)OC(C)C)cc1] |
| IS-102-081 | 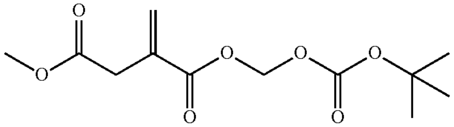 [SMILES: C=C(CC(=O)OC)C(=O)OCOC(=O)OC(C)(C)C] | 1-MI | $CH_3O$— | 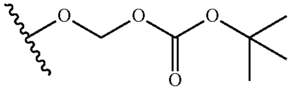 [SMILES: *OCOC(=O)OC(C)(C)C] |
†4-MI refers to 4-methyl itaconate;
‡1-MI refers to 1-methyl itaconate In yet other embodiments, the presently disclosed subject matter provides a method for treating a disease, disorder, or condition associated with inflammation, the method comprising administering to a subject in need of treatment thereof a compound of formula (I) or a pharmaceutical composition thereof.

As used herein, the term "treating" can include reversing, alleviating, inhibiting the progression of, preventing or reducing the likelihood of the disease, disorder, or condition to which such term applies, or one or more symptoms manifestations of such disease, disorder or condition. Preventing refers to causing a disease, disorder, condition, or symptom or manifestation of such, or worsening of the severity of such, not to occur. Accordingly, the presently disclosed compounds can be administered prophylactically to prevent or reduce the incidence or recurrence of the disease, disorder, or condition.

The "subject" treated by the presently disclosed methods in their many embodiments is desirably a human subject, although it is to be understood that the methods described herein are effective with respect to all vertebrate species, which are intended to be included in the term "subject." Accordingly, a "subject" can include a human subject for medical purposes, such as for the treatment of an existing condition or disease or the prophylactic treatment for preventing the onset of a condition or disease, or an animal subject for medical, veterinary purposes, or developmental purposes. Suitable animal subjects include mammals including, but not limited to, primates, e.g., humans, monkeys, apes, and the like; bovines, e.g., cattle, oxen, and the like; ovines, e.g., sheep and the like; caprines, e.g., goats and the like; porcines, e.g., pigs, hogs, and the like; equines, e.g., horses, donkeys, zebras, and the like; felines, including wild and domestic cats; canines, including dogs; lagomorphs, including rabbits, hares, and the like; and rodents, including mice, rats, and the like. An animal may be a transgenic animal. In some embodiments, the subject is a human including, but not limited to, fetal, neonatal, infant, juvenile, and adult subjects. Further, a "subject" can include a patient afflicted with or suspected of being afflicted with a condition or disease. Thus, the terms "subject" and "patient" are used interchangeably herein. The term "subject" also refers to an organism, tissue, cell, or collection of cells from a subject.

In general, the "effective amount" of an active agent or drug delivery device refers to the amount necessary to elicit the desired biological response. As will be appreciated by those of ordinary skill in this art, the effective amount of an agent or device may vary depending on such factors as the desired biological endpoint, the agent to be delivered, the makeup of the pharmaceutical composition, the target tissue, and the like.

The term "combination" is used in its broadest sense and means that a subject is administered at least two agents, more particularly a compound of formula (I) and at least one beta-lactam antibiotic and, optionally, one or more antibacterial agents. More particularly, the term "in combination" refers to the concomitant administration of two (or more) active agents for the treatment of a, e.g., single disease state. As used herein, the active agents may be combined and administered in a single dosage form, may be administered as separate dosage forms at the same time, or may be administered as separate dosage forms that are administered alternately or sequentially on the same or separate days. In one embodiment of the presently disclosed subject matter, the active agents are combined and administered in a single dosage form. In another embodiment, the active agents are administered in separate dosage forms (e.g., wherein it is desirable to vary the amount of one but not the other). The single dosage form may include additional active agents for the treatment of the disease state.

Further, the compounds of formula (I) described herein can be administered alone or in combination with adjuvants that enhance stability of the compounds of formula (I), alone or in combination with one or more antibacterial agents, facilitate administration of pharmaceutical compositions containing them in certain embodiments, provide increased dissolution or dispersion, increase inhibitory activity, provide adjunct therapy, and the like, including other active ingredients. Advantageously, such combination therapies utilize lower dosages of the conventional therapeutics, thus avoiding possible toxicity and adverse side effects incurred when those agents are used as monotherapies.

The timing of administration of a compound of formula (I) and at least one additional therapeutic agent can be varied so long as the beneficial effects of the combination of these agents are achieved. Accordingly, the phrase "in combination with" refers to the administration of a compound of formula (I) and at least one additional therapeutic agent either simultaneously, sequentially, or a combination thereof. Therefore, a subject administered a combination of a compound of formula (I) and at least one additional therapeutic agent can receive compound of formula (I) and at least one additional therapeutic agent at the same time (i.e., simultaneously) or at different times (i.e., sequentially, in either order, on the same day or on different days), so long as the effect of the combination of both agents is achieved in the subject.

When administered sequentially, the agents can be administered within 1, 5, 10, 30, 60, 120, 180, 240 minutes or longer of one another. In other embodiments, agents administered sequentially, can be administered within 1, 5, 10, 15, 20 or more days of one another. Where the compound of formula (I) and at least one additional therapeutic agent are administered simultaneously, they can be administered to the subject as separate pharmaceutical compositions, each comprising either a compound of formula (I) or at least one additional therapeutic agent, or they can be administered to a subject as a single pharmaceutical composition comprising both agents.

When administered in combination, the effective concentration of each of the agents to elicit a particular biological response may be less than the effective concentration of each agent when administered alone, thereby allowing a reduction in the dose of one or more of the agents relative to the dose that would be needed if the agent was administered as a single agent. The effects of multiple agents may, but need not be, additive or synergistic. The agents may be administered multiple times.

In some embodiments, when administered in combination, the two or more agents can have a synergistic effect. As used herein, the terms "synergy," "synergistic," "synergistically" and derivations thereof, such as in a "synergistic effect" or a "synergistic combination" or a "synergistic composition" refer to circumstances under which the biological activity of a combination of a compound of formula (I) and at least one additional therapeutic agent is greater than the sum of the biological activities of the respective agents when administered individually.

Synergy can be expressed in terms of a "Synergy Index (SI)," which generally can be determined by the method described by F. C. Kull et al., Applied Microbiology 9, 538 (1961), from the ratio determined by:

$$Q_a/Q_A+Q_b/Q_B=\text{Synergy Index (SI)}$$

wherein:

- $Q_A$ is the concentration of a component A, acting alone, which produced an end point in relation to component A;
- $Q_a$ is the concentration of component A, in a mixture, which produced an end point;
- $Q_B$ is the concentration of a component B, acting alone, which produced an end point in relation to component B; and
- $Q_b$ is the concentration of component B, in a mixture, which produced an end point.

Generally, when the sum of $Q_a/Q_A$ and $Q_b/Q_B$ is greater than one, antagonism is indicated. When the sum is equal to one, additivity is indicated. When the sum is less than one, synergism is demonstrated. The lower the SI, the greater the synergy shown by that particular mixture. Thus, a "synergistic combination" has an activity higher that what can be expected based on the observed activities of the individual components when used alone. Further, a "synergistically effective amount" of a component refers to the amount of the component necessary to elicit a synergistic effect in, for example, another therapeutic agent present in the composition.

In another embodiment, the presently disclosed subject matter provides a pharmaceutical composition including one compound of formula (I) alone or in combination with one or more additional therapeutic agents in admixture with a pharmaceutically acceptable excipient. One of skill in the art will recognize that the pharmaceutical compositions include the pharmaceutically acceptable salts of the compounds described above. Pharmaceutically acceptable salts are generally well known to those of ordinary skill in the art, and include salts of active compounds which are prepared with relatively nontoxic acids or bases, depending on the particular substituent moieties found on the compounds described herein. When compounds of the present disclosure contain relatively acidic functionalities, base addition salts can be obtained by contacting the neutral form of such compounds with a sufficient amount of the desired base, either neat or in a suitable inert solvent or by ion exchange, whereby one basic counterion (base) in an ionic complex is substituted for another. Examples of pharmaceutically acceptable base addition salts include sodium, potassium, calcium, ammonium, organic amino, or magnesium salt, or a similar salt.

When compounds of the present disclosure contain relatively basic functionalities, acid addition salts can be obtained by contacting the neutral form of such compounds with a sufficient amount of the desired acid, either neat or in a suitable inert solvent or by ion exchange, whereby one acidic counterion (acid) in an ionic complex is substituted for another. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-toluenesulfonic, citric, tartaric, methanesulfonic, and the like. Also included are salts of amino acids such as arginate and the like, and salts of organic acids like glucuronic or galactunoric acids and the like (see, for example, Berge et al, "Pharmaceutical Salts", Journal of Pharmaceutical Science, 1977, 66, 1-19). Certain specific compounds of the present disclosure contain both basic and acidic functionalities that allow the compounds to be converted into either base or acid addition salts.

Accordingly, pharmaceutically acceptable salts suitable for use with the presently disclosed subject matter include, by way of example but not limitation, acetate, benzenesulfonate, benzoate, bicarbonate, bitartrate, bromide, calcium edetate, camsylate, carbonate, citrate, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, mucate, napsylate, nitrate, pamoate (embonate), pantothenate, phosphate/diphosphate, polygalacturonate, salicylate, stearate, subacetate, succinate, sulfate, tannate, tartrate, or teoclate. Other pharmaceutically acceptable salts may be found in, for example, Remington: The Science and Practice of Pharmacy ($20^{th}$ ed.) Lippincott, Williams & Wilkins (2000).

In therapeutic and/or diagnostic applications, the compounds of the disclosure can be formulated for a variety of modes of administration, including systemic and topical or localized administration. Techniques and formulations generally may be found in Remington: The Science and Practice of Pharmacy ($20^{th}$ ed.) Lippincott, Williams & Wilkins (2000).

Depending on the specific conditions being treated, such agents may be formulated into liquid or solid dosage forms and administered systemically or locally.

The agents may be delivered, for example, in a timed- or sustained-slow release form as is known to those skilled in the art. Techniques for formulation and administration may be found in Remington: The Science and Practice of Pharmacy ($20^{th}$ ed.) Lippincott, Williams & Wilkins (2000). Suitable routes may include oral, buccal, by inhalation spray, sublingual, rectal, transdermal, vaginal, transmucosal, nasal or intestinal administration; parenteral delivery, including intramuscular, subcutaneous, intramedullary injections, as well as intrathecal, direct intraventricular, intravenous, intra-articullar, intra-sternal, intra-synovial, intra-hepatic, intralesional, intracranial, intraperitoneal, intranasal, or intraocular injections or other modes of delivery.

For injection, the agents of the disclosure may be formulated and diluted in aqueous solutions, such as in physiologically compatible buffers such as Hank's solution, Ringer's solution, or physiological saline buffer. For such transmucosal administration, penetrants appropriate to the barrier to be permeated are used in the formulation. Such penetrants are generally known in the art.

Use of pharmaceutically acceptable inert carriers to formulate the compounds herein disclosed for the practice of the disclosure into dosages suitable for systemic administration is within the scope of the disclosure. With proper choice of carrier and suitable manufacturing practice, the compositions of the present disclosure, in particular, those formulated as solutions, may be administered parenterally, such as by intravenous injection. The compounds can be formulated readily using pharmaceutically acceptable carriers well known in the art into dosages suitable for oral administration. Such carriers enable the compounds of the disclosure to be formulated as tablets, pills, capsules, liquids, gels, syrups, slurries, suspensions and the like, for oral ingestion by a subject (e.g., patient) to be treated.

For nasal or inhalation delivery, the agents of the disclosure also may be formulated by methods known to those of skill in the art, and may include, for example, but not limited to, examples of solubilizing, diluting, or dispersing substances, such as saline; preservatives, such as benzyl alcohol; absorption promoters; and fluorocarbons.

Pharmaceutical compositions suitable for use in the present disclosure include compositions wherein the active ingredients are contained in an effective amount to achieve its intended purpose. Determination of the effective amounts is well within the capability of those skilled in the art, especially in light of the detailed disclosure provided herein. Generally, the compounds according to the disclosure are effective over a wide dosage range. For example, in the treatment of adult humans, dosages from 0.01 to 1000 mg, from 0.5 to 100 mg, from 1 to 50 mg per day, and from 5 to 40 mg per day are examples of dosages that may be used. A non-limiting dosage is 10 to 30 mg per day. The exact dosage will depend upon the route of administration, the form in which the compound is administered, the subject to be treated, the body weight of the subject to be treated, the bioavailability of the compound(s), the adsorption, distribution, metabolism, and excretion (ADME) toxicity of the compound(s), and the preference and experience of the attending physician.

In addition to the active ingredients, these pharmaceutical compositions may contain suitable pharmaceutically acceptable carriers comprising excipients and auxiliaries which facilitate processing of the active compounds into preparations which can be used pharmaceutically. The preparations formulated for oral administration may be in the form of tablets, dragees, capsules, or solutions.

Pharmaceutical preparations for oral use can be obtained by combining the active compounds with solid excipients, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations, for example, maize starch, wheat starch, rice starch, potato starch, gelatin, gum tragacanth, methyl cellulose, hydroxypropylmethyl-cellulose, sodium carboxymethyl-cellulose (CMC), and/or polyvinylpyrrolidone (PVP: povidone). If desired, disintegrating agents may be added, such as the cross-linked polyvinylpyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinylpyrrolidone, carbopol gel, polyethylene glycol (PEG), and/or titanium dioxide, lacquer solutions, and suitable organic solvents or solvent mixtures. Dye-stuffs or pigments may be added to the tablets or dragee coatings for identification or to characterize different combinations of active compound doses.

Pharmaceutical preparations that can be used orally include push-fit capsules made of gelatin, as well as soft, sealed capsules made of gelatin, and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols (PEGs). In addition, stabilizers may be added.

In yet other embodiments, the presently disclosed compounds of formula (I) can be formulated into a viscous lotion, cream, ointment, suspension, paste, gel, oil, spray, or aerosol and administered topically. Such viscous lotions, creams, or ointments can be water based and can further comprise an oil (water-in-oil or oil-in-water), such as liquid paraffin or vegetable oil, e.g., arachis oil or castor oil, or a solvent, and can include one or more other components, including, but not limited to, penetration enhancers, e.g., ethanol and propylene glycol, moisturizing agents, including, but not limited to, glycerin and/or glycerol, thickening and/or gelling agents, including, but not limited to, soft paraffin, aluminium stearate, cetostearyl alcohol, polyethylene glycols, woolfat, beeswax, carboxypolymethylene and cellulose derivatives, and/or glyceryl monostearate and/or non-ionic emulsifying agents, stabilizing agents, dispersing agents, and suspending agents. By way of example only, a common liquid formulation can comprise between about 10% to about 60% water, about 10% to about 70% ethanol, about 5% to about 10% propylene glycol, and about 2% to about 5% moisturizing agent.

II. Definitions

Although specific terms are employed herein, they are used in a generic and descriptive sense only and not for purposes of limitation. Unless otherwise defined, all technical and scientific terms used herein have the same meaning as commonly understood by one of ordinary skill in the art to which this presently described subject matter belongs.

While the following terms in relation to compounds of formula (I) are believed to be well understood by one of ordinary skill in the art, the following definitions are set forth to facilitate explanation of the presently disclosed subject matter. These definitions are intended to supplement and illustrate, not preclude, the definitions that would be apparent to one of ordinary skill in the art upon review of the present disclosure.

The terms substituted, whether preceded by the term "optionally" or not, and substituent, as used herein, refer to the ability, as appreciated by one skilled in this art, to change one functional group for another functional group on a molecule, provided that the valency of all atoms is maintained. When more than one position in any given structure may be substituted with more than one substituent selected from a specified group, the substituent may be either the same or different at every position.

The substituents also may be further substituted (e.g., an aryl group substituent may have another substituent off it, such as another aryl group, which is further substituted at one or more positions).

Where substituent groups or linking groups are specified by their conventional chemical formulae, written from left to right, they equally encompass the chemically identical substituents that would result from writing the structure from right to left, e.g., $—CH_2O—$ is equivalent to $—OCH_2—$; $—C(=O)O—$ is equivalent to $—OC(=O)—$; $—OC(=O)NR—$ is equivalent to $—NRC(=O)O—$, and the like.

When the term "independently selected" is used, the substituents being referred to (e.g., R groups, such as groups $R_1$, $R_2$, and the like, or variables, such as "m" and "n"), can be identical or different. For example, both $R_1$ and $R_2$ can be substituted alkyls, or $R_1$ can be hydrogen and $R_2$ can be a substituted alkyl, and the like.

The terms "a," "an," or "a(n)," when used in reference to a group of substituents herein, mean at least one. For example, where a compound is substituted with "an" alkyl or aryl, the compound is optionally substituted with at least one alkyl and/or at least one aryl. Moreover, where a moiety is substituted with an R substituent, the group may be referred to as "R-substituted." Where a moiety is R-substituted, the moiety is substituted with at least one R substituent and each R substituent is optionally different.

A named “R” or group will generally have the structure that is recognized in the art as corresponding to a group having that name, unless specified otherwise herein. For the purposes of illustration, certain representative “R” groups as set forth above are defined below.

Descriptions of compounds of the present disclosure are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

Unless otherwise explicitly defined, a “substituent group,” as used herein, includes a functional group selected from one or more of the following moieties, which are defined herein:

The term hydrocarbon, as used herein, refers to any chemical group comprising hydrogen and carbon. The hydrocarbon may be substituted or unsubstituted. As would be known to one skilled in this art, all valencies must be satisfied in making any substitutions. The hydrocarbon may be unsaturated, saturated, branched, unbranched, cyclic, polycyclic, or heterocyclic. Illustrative hydrocarbons are further defined herein below and include, for example, methyl, ethyl, n-propyl, isopropyl, cyclopropyl, allyl, vinyl, n-butyl, tert-butyl, ethynyl, cyclohexyl, and the like.

The term “alkyl,” by itself or as part of another substituent, means, unless otherwise stated, a straight (i.e., unbranched) or branched chain, acyclic or cyclic hydrocarbon group, or combination thereof, which may be fully saturated, mono- or polyunsaturated and can include di- and multivalent groups, having the number of carbon atoms designated (i.e., $C_{1-10}$ means one to ten carbons, including 1, 2, 3, 4, 5, 6, 7, 8, 9, and 10 carbons). In particular embodiments, the term “alkyl” refers to $C_{1-20}$ inclusive, including 1, 2, 3, 4, 5, 6, 7, 8, 9, 10, 11, 12, 13, 14, 15, 16, 17, 18, 19, and 20 carbons, linear (i.e., “straight-chain”), branched, or cyclic, saturated or at least partially and in some cases fully unsaturated (i.e., alkenyl and alkynyl) hydrocarbon radicals derived from a hydrocarbon moiety containing between one and twenty carbon atoms by removal of a single hydrogen atom.

Representative saturated hydrocarbon groups include, but are not limited to, methyl, ethyl, n-propyl, isopropyl, n-butyl, isobutyl, sec-butyl, tert-butyl, n-pentyl, sec-pentyl, isopentyl, neopentyl, n-hexyl, sec-hexyl, n-heptyl, n-octyl, n-decyl, n-undecyl, dodecyl, cyclohexyl, (cyclohexyl)methyl, cyclopropylmethyl, and homologs and isomers thereof.

“Branched” refers to an alkyl group in which a lower alkyl group, such as methyl, ethyl or propyl, is attached to a linear alkyl chain. “Lower alkyl” refers to an alkyl group having 1 to about 8 carbon atoms (i.e., a $C_{1-8}$ alkyl), e.g., 1, 2, 3, 4, 5, 6, 7, or 8 carbon atoms. “Higher alkyl” refers to an alkyl group having about 10 to about 20 carbon atoms, e.g., 10, 11, 12, 13, 14, 15, 16, 17, 18, 19, or 20 carbon atoms. In certain embodiments, “alkyl” refers, in particular, to $C_{1-8}$ straight-chain alkyls. In other embodiments, “alkyl” refers, in particular, to $C_{1-8}$ branched-chain alkyls.

Alkyl groups can optionally be substituted (a “substituted alkyl”) with one or more alkyl group substituents, which can be the same or different. The term “alkyl group substituent” includes but is not limited to alkyl, substituted alkyl, halo, arylamino, acyl, hydroxyl, aryloxyl, alkoxyl, alkylthio, arylthio, aralkyloxyl, aralkylthio, carboxyl, alkoxycarbonyl, oxo, and cycloalkyl. There can be optionally inserted along the alkyl chain one or more oxygen, sulfur or substituted or unsubstituted nitrogen atoms, wherein the nitrogen substituent is hydrogen, lower alkyl (also referred to herein as “alkylaminoalkyl”), or aryl.

Thus, as used herein, the term “substituted alkyl” includes alkyl groups, as defined herein, in which one or more atoms or functional groups of the alkyl group are replaced with another atom or functional group, including for example, alkyl, substituted alkyl, halogen, aryl, substituted aryl, alkoxyl, hydroxyl, nitro, amino, alkylamino, dialkylamino, sulfate, cyano, and mercapto.

The term “heteroalkyl,” by itself or in combination with another term, means, unless otherwise stated, a stable straight or branched chain having from 1 to 20 carbon atoms or heteroatoms or a cyclic hydrocarbon group having from 3 to 10 carbon atoms or heteroatoms, or combinations thereof, consisting of at least one carbon atom and at least one heteroatom selected from the group consisting of O, N, P, Si and S, and wherein the nitrogen, phosphorus, and sulfur atoms may optionally be oxidized and the nitrogen heteroatom may optionally be quaternized. The heteroatom(s) 0, N, P and S and Si may be placed at any interior position of the heteroalkyl group or at the position at which alkyl group is attached to the remainder of the molecule. Examples include, but are not limited to, $—CH_2—CH_2—O—CH_3$, $—CH_2—CH_2—NH—CH_3$, $—CH_2—CH_2—N(CH_3)—CH_3$, $—CH_2—S—CH_2—CH_3$, $—CH_2—CH_2—S(O)—CH_3$, $—CH_2—CH_2—S(O)_2—CH_3$, $—CH=CH—O—CH_3$, $—Si(CH_3)_3$, $—CH_2—CH=N—OCH_3$, $—CH=CH—N(CH_3)— CH_3$, $O—CH_3$, $—O—CH_2—CH_3$, and —CN. Up to two or three heteroatoms may be consecutive, such as, for example, $—CH_2—NH—OCH_3$ and $—CH_2—O—Si(CH_3)_3$.

As described above, heteroalkyl groups, as used herein, include those groups that are attached to the remainder of the molecule through a heteroatom, such as —C(O)NR', —NR'R", —OR', —SR, —S(O)R, and/or $—S(O_2)R'$. Where “heteroalkyl” is recited, followed by recitations of specific heteroalkyl groups, such as —NR'R or the like, it will be understood that the terms heteroalkyl and —NR'R" are not redundant or mutually exclusive. Rather, the specific heteroalkyl groups are recited to add clarity.

Thus, the term “heteroalkyl” should not be interpreted herein as excluding specific heteroalkyl groups, such as —NR'R" or the like.

“Cyclic” and “cycloalkyl” refer to a non-aromatic mono- or multicyclic ring system of about 3 to about 10 carbon atoms, e.g., 3, 4, 5, 6, 7, 8, 9, or 10 carbon atoms. The cycloalkyl group can be optionally partially unsaturated. The cycloalkyl group also can be optionally substituted with an alkyl group substituent as defined herein, oxo, and/or alkylene. There can be optionally inserted along the cyclic alkyl chain one or more oxygen, sulfur or substituted or unsubstituted nitrogen atoms, wherein the nitrogen substituent is hydrogen, unsubstituted alkyl, substituted alkyl, aryl, or substituted aryl, thus providing a heterocyclic group. Representative monocyclic cycloalkyl rings include cyclopentyl, cyclohexyl, and cycloheptyl. Multicyclic cycloalkyl rings include adamantyl, octahydronaphthyl, decalin, camphor, camphane, and noradamantyl, and fused ring systems, such as dihydro- and tetrahydronaphthalene, and the like.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. The terms "cycloalkylene" and "heterocycloalkylene" refer to the divalent derivatives of cycloalkyl and heterocycloalkyl, respectively.

An unsaturated hydrocarbon has one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. Alkyl groups which are limited to hydrocarbon groups are termed "homoalkyl."

More particularly, the term "alkenyl" as used herein refers to a monovalent group derived from a $C_{2-20}$ inclusive straight or branched hydrocarbon moiety having at least one carbon-carbon double bond by the removal of a single hydrogen molecule. Alkenyl groups include, for example, ethenyl (i.e., vinyl), propenyl, butenyl, 1-methyl-2-buten-1-yl, pentenyl, hexenyl, octenyl, allenyl, and butadienyl.

The term "cycloalkenyl" as used herein refers to a cyclic hydrocarbon containing at least one carbon-carbon double bond. Examples of cycloalkenyl groups include cyclopropenyl, cyclobutenyl, cyclopentenyl, cyclopentadiene, cyclohexenyl, 1,3-cyclohexadiene, cycloheptenyl, cycloheptatrienyl, and cyclooctenyl.

The term "alkynyl" as used herein refers to a monovalent group derived from a straight or branched $C_{2-20}$ hydrocarbon of a designed number of carbon atoms containing at least one carbon-carbon triple bond. Examples of "alkynyl" include ethynyl, 2-propynyl (propargyl), 1-propynyl, pentynyl, hexynyl, and heptynyl groups, and the like.

The term "alkylene" by itself or a part of another substituent refers to a straight or branched bivalent aliphatic hydrocarbon group derived from an alkyl group having from 1 to about 20 carbon atoms, e.g., 1, 2, 3, 4, 5, 6, 7, 8, 9, 10, 11, 12, 13, 14, 15, 16, 17, 18, 19, or 20 carbon atoms. The alkylene group can be straight, branched or cyclic. The alkylene group also can be optionally unsaturated and/or substituted with one or more "alkyl group substituents." There can be optionally inserted along the alkylene group one or more oxygen, sulfur or substituted or unsubstituted nitrogen atoms (also referred to herein as "alkylaminoalkyl"), wherein the nitrogen substituent is alkyl as previously described. Exemplary alkylene groups include methylene ($—CH_2—$); ethylene ($—CH_2—CH_2—$); propylene ($—(CH_2)_3—$); cyclohexylene ($—C_6H_{10}—$); —CH=CH—CH=CH—; $—CH=CH—CH_2—$; $—CH_2CH_2CH_2CH_2—$, $—CH_2CH=CHCH_2—$, $—CH_2CsCCH_2—$, $—CH_2CH_2CH(CH_2CH_2CH_3)CH_2—$, $—(CH_2)_q—N(R)—(CH_2)_r—$, wherein each of q and r is independently an integer from 0 to about 20, e.g., 0, 1, 2, 3, 4, 5, 6, 7, 8, 9, 10, 11, 12, 13, 14, 15, 16, 17, 18, 19, or 20, and R is hydrogen or lower alkyl; methylenedioxyl ($—O—CH_2—O—$); and ethylenedioxyl ($—O—(CH_2)_2—O—$). An alkylene group can have about 2 to about 3 carbon atoms and can further have 6-20 carbons. Typically, an alkyl (or alkylene) group will have from 1 to 24 carbon atoms, with those groups having 10 or fewer carbon atoms being some embodiments of the present disclosure. A "lower alkyl" or "lower alkylene" is a shorter chain alkyl or alkylene group, generally having eight or fewer carbon atoms.

The term "heteroalkylene" by itself or as part of another substituent means a divalent group derived from heteroalkyl, as exemplified, but not limited by, $—CH_2—CH_2—S—CH_2—CH_2—$ and $—CH_2—S—CH_2—CH_2—NH—CH_2—$. For heteroalkylene groups, heteroatoms also can occupy either or both of the chain termini (e.g., alkyleneoxo, alkylenedioxo, alkyleneamino, alkylenediamino, and the like). Still further, for alkylene and heteroalkylene linking groups, no orientation of the linking group is implied by the direction in which the formula of the linking group is written. For example, the formula —C(O)OR'— represents both —C(O)OR'— and —R'OC(O)—.

The term "aryl" means, unless otherwise stated, an aromatic hydrocarbon substituent that can be a single ring or multiple rings (such as from 1 to 3 rings), which are fused together or linked covalently. The term "heteroaryl" refers to aryl groups (or rings) that contain from one to four heteroatoms (in each separate ring in the case of multiple rings) selected from N, O, and S, wherein the nitrogen and sulfur atoms are optionally oxidized, and the nitrogen atom(s) are optionally quaternized. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of above noted aryl and heteroaryl ring systems are selected from the group of acceptable substituents described below. The terms "arylene" and "heteroarylene" refer to the divalent forms of aryl and heteroaryl, respectively.

For brevity, the term "aryl" when used in combination with other terms (e.g., aryloxy, arylthioxy, arylalkyl) includes both aryl and heteroaryl rings as defined above. Thus, the terms "arylalkyl" and "heteroarylalkyl" are meant to include those groups in which an aryl or heteroaryl group is attached to an alkyl group (e.g., benzyl, phenethyl, pyridylmethyl, furylmethyl, and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like). However, the term "haloaryl," as used herein is meant to cover only aryls substituted with one or more halogens.

Where a heteroalkyl, heterocycloalkyl, or heteroaryl includes a specific number of members (e.g. "3 to 7 membered"), the term "member" refers to a carbon or heteroatom.

Further, a structure represented generally by the formula:

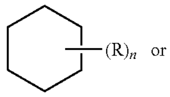 or 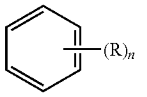

as used herein refers to a ring structure, for example, but not limited to a 3-carbon, a 4-carbon, a 5-carbon, a 6-carbon, a 7-carbon, and the like, aliphatic and/or aromatic cyclic compound, including a saturated ring structure, a partially saturated ring structure, and an unsaturated ring structure, comprising a substituent R group, wherein the R group can be present or absent, and when present, one or more R groups can each be substituted on one or more available carbon atoms of the ring structure. The presence or absence of the R group and number of R groups is determined by the value of the variable "n," which is an integer generally having a value ranging from 0 to the number of carbon atoms on the ring available for substitution. Each R group, if more than one, is substituted on an available carbon of the ring structure rather than on another R group. For example, the structure above where n is 0 to 2 would comprise compound groups including, but not limited to:

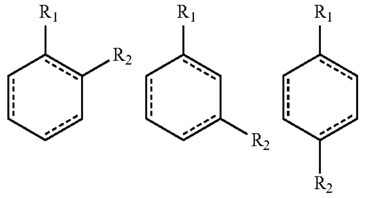

and the like.

A dashed line representing a bond in a cyclic ring structure indicates that the bond can be either present or absent in the ring. That is, a dashed line representing a bond in a cyclic ring structure indicates that the ring structure is selected from the group consisting of a saturated ring structure, a partially saturated ring structure, and an unsaturated ring structure.

The symbol (

) denotes the point of attachment of a moiety to the remainder of the molecule.

When a named atom of an aromatic ring or a heterocyclic aromatic ring is defined as being "absent," the named atom is replaced by a direct bond.

As used herein, the term "acyl" refers to an organic acid group wherein the —OH of the carboxyl group has been replaced with another substituent and has the general formula RC(=O)—, wherein R is an alkyl, alkenyl, alkynyl, aryl, carbocylic, heterocyclic, or aromatic heterocyclic group as defined herein). As such, the term "acyl" specifically includes arylacyl groups, such as a 2-(furan-2-yl) acetyl)- and a 2-phenylacetyl group. Specific examples of acyl groups include acetyl and benzoyl.

Acyl groups also are intended to include amides, —RC(=O)NR', esters, —RC(=O)OR', ketones, —RC(=O)R', and aldehydes, —RC(=O)H.

The terms "alkoxyl" or "alkoxy" are used interchangeably herein and refer to a saturated (i.e., alkyl-O—) or unsaturated (i.e., alkenyl-O— and alkynyl-O—) group attached to the parent molecular moiety through an oxygen atom, wherein the terms "alkyl," "alkenyl," and "alkynyl" are as previously described and can include $C_{1-20}$ inclusive, linear, branched, or cyclic, saturated or unsaturated oxo-hydrocarbon chains, including, for example, methoxyl, ethoxyl, propoxyl, isopropoxyl, n-butoxyl, sec-butoxyl, tert-butoxyl, and n-pentoxyl, neopentoxyl, n-hexoxyl, and the like.

The term "alkoxyalkyl" as used herein refers to an alkyl-O-alkyl ether, for example, a methoxyethyl or an ethoxymethyl group.

"Aryloxyl" refers to an aryl-O— group wherein the aryl group is as previously described, including a substituted aryl. The term "aryloxyl" as used herein can refer to phenyloxyl or hexyloxyl, and alkyl, substituted alkyl, halo, or alkoxyl substituted phenyloxyl or hexyloxyl.

"Aralkyl" refers to an aryl-alkyl-group wherein aryl and alkyl are as previously described, and included substituted aryl and substituted alkyl. Exemplary aralkyl groups include benzyl, phenylethyl, and naphthylmethyl.

"Aralkyloxyl" refers to an aralkyl-O— group wherein the aralkyl group is as previously described. An exemplary aralkyloxyl group is benzyloxyl, i.e., $C_6H_5$—$CH_2$—O—. An aralkyloxyl group can optionally be substituted.

"Alkoxycarbonyl" refers to an alkyl-O—C(=O)— group. Exemplary alkoxycarbonyl groups include methoxycarbonyl, ethoxycarbonyl, butyloxycarbonyl, and tert-butyloxycarbonyl.

"Aryloxycarbonyl" refers to an aryl-O—C(=O)— group. Exemplary aryloxycarbonyl groups include phenoxy- and naphthoxy-carbonyl.

"Aralkoxycarbonyl" refers to an aralkyl-O—C(=O)— group. An exemplary aralkoxycarbonyl group is benzyloxycarbonyl.

"Carbamoyl" refers to an amide group of the formula —C(=O)$NH_2$.

"Alkylcarbamoyl" refers to a R'RN—C(=O)— group wherein one of R and R' is hydrogen and the other of R and R' is alkyl and/or substituted alkyl as previously described.

"Dialkylcarbamoyl" refers to a R'RN—C(=O)— group wherein each of R and R' is independently alkyl and/or substituted alkyl as previously described.

The term carbonyldioxyl, as used herein, refers to a carbonate group of the formula —O—C(=O)—OR.

"Acyloxyl" refers to an acyl-O— group wherein acyl is as previously described.

The term "amino" refers to the —$NH_2$ group and also refers to a nitrogen containing group as is known in the art derived from ammonia by the replacement of one or more hydrogen radicals by organic radicals. For example, the terms "acylamino" and "alkylamino" refer to specific N-substituted organic radicals with acyl and alkyl substituent groups respectively.

An "aminoalkyl" as used herein refers to an amino group covalently bound to an alkylene linker. More particularly, the terms alkylamino, dialkylamino, and trialkylamino as used herein refer to one, two, or three, respectively, alkyl groups, as previously defined, attached to the parent molecular moiety through a nitrogen atom. The term alkylamino refers to a group having the structure —NHR' wherein R' is an alkyl group, as previously defined; whereas the term dialkylamino refers to a group having the structure —NR'R", wherein R' and R" are each independently selected from the group consisting of alkyl groups. The term trialkylamino refers to a group having the structure —NR'R"R"', wherein R', R", and R"' are each independently selected from the group consisting of alkyl groups. Additionally, R', R", and/or R"' taken together may optionally be —$(CH_2)_k$— where k is an integer from 2 to 6. Examples include, but are not limited to, methylamino, dimethylamino, ethylamino, diethylamino, diethylaminocarbonyl, methylethylamino, isopropylamino, piperidino, trimethylamino, and propylamino.

The amino group is —NR'R", wherein R' and R" are typically selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

The terms alkylthioether and thioalkoxyl refer to a saturated (i.e., alkyl-S—) or unsaturated (i.e., alkenyl-S— and alkynyl-S—) group attached to the parent molecular moiety through a sulfur atom. Examples of thioalkoxyl moieties include, but are not limited to, methylthio, ethylthio, propylthio, isopropylthio, n-butylthio, and the like.

"Acylamino" refers to an acyl-NH— group wherein acyl is as previously described. "Aroylamino" refers to an aroyl-NH— group wherein aroyl is as previously described.

The term "carbonyl" refers to the —C(═O)— group, and can include an aldehyde group represented by the general formula R—C(═O)H.

The term "carboxyl" refers to the —COOH group. Such groups also are referred to herein as a "carboxylic acid" moiety.

The term "cyano" refers to the —C≡N group.

The terms "halo," "halide," or "halogen" as used herein refer to fluoro, chloro, bromo, and iodo groups. Additionally, terms such as "haloalkyl," are meant to include monohaloalkyl and polyhaloalkyl. For example, the term "halo($C_{1-4}$)alkyl" is mean to include, but not be limited to, trifluoromethyl, 2,2,2-trifluoroethyl, 4-chlorobutyl, 3-bromopropyl, and the like.

The term "hydroxyl" refers to the —OH group.

The term "hydroxyalkyl" refers to an alkyl group substituted with an —OH group.

The term "mercapto" refers to the —SH group.

The term "oxo" as used herein means an oxygen atom that is double bonded to a carbon atom or to another element.

The term "nitro" refers to the —$NO_2$ group.

The term "thio" refers to a compound described previously herein wherein a carbon or oxygen atom is replaced by a sulfur atom.

The term "sulfate" refers to the —$SO_4$ group.

The term thiohydroxyl or thiol, as used herein, refers to a group of the formula —SH.

More particularly, the term "sulfide" refers to compound having a group of the formula —SR.

The term "sulfone" refers to compound having a sulfonyl group —$S(O_2)R$.

The term "sulfoxide" refers to a compound having a sulfinyl group —S(O)R The term ureido refers to a urea group of the formula —NH—CO—$NH_2$.

Throughout the specification and claims, a given chemical formula or name shall encompass all tautomers, congeners, and optical- and stereoisomers, as well as racemic mixtures where such isomers and mixtures exist.

Certain compounds of the present disclosure may possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as D- or L- for amino acids, and individual isomers are encompassed within the scope of the present disclosure. The present disclosure is meant to include compounds in racemic, scalemic, and optically pure forms. Optically active (R)- and (S)-, or D- and L-isomers may be prepared using chiral synthons or chiral reagents, or resolved using conventional techniques. When the compounds described herein contain olefenic bonds or other centers of geometric asymmetry, and unless specified otherwise, it is intended that the compounds include both E and Z geometric isomers.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the disclosure.

It will be apparent to one skilled in the art that certain compounds of this disclosure may exist in tautomeric forms, all such tautomeric forms of the compounds being within the scope of the disclosure. The term "tautomer," as used herein, refers to one of two or more structural isomers which exist in equilibrium and which are readily converted from one isomeric form to another.

Unless otherwise stated, structures depicted herein are also meant to include compounds which differ only in the presence of one or more isotopically enriched atoms. For example, compounds having the present structures with the replacement of a hydrogen by a deuterium or tritium, or the replacement of a carbon by $^{13}C$- or $^{14}C$-enriched carbon are within the scope of this disclosure.

The compounds of the present disclosure may also contain unnatural proportions of atomic isotopes at one or more of atoms that constitute such compounds. For example, the compounds may be radiolabeled with radioactive isotopes, such as for example tritium ($^{3}H$), iodine-125 ($^{125}I$) or carbon-14 ($^{14}C$). All isotopic variations of the compounds of the present disclosure, whether radioactive or not, are encompassed within the scope of the present disclosure.

Certain compounds of the present disclosure can exist in unsolvated forms as well as solvated forms, including hydrated forms. In general, the solvated forms are equivalent to unsolvated forms and are encompassed within the scope of the present disclosure. Certain compounds of the present disclosure may exist in multiple crystalline or amorphous forms. In general, all physical forms are equivalent for the uses contemplated by the present disclosure and are intended to be within the scope of the present disclosure.

The term "protecting group" refers to chemical moieties that block some or all reactive moieties of a compound and prevent such moieties from participating in chemical reactions until the protective group is removed, for example, those moieties listed and described in T. W. Greene, P. G. M. Wuts, Protective Groups in Organic Synthesis, 3rd ed. John Wiley & Sons (1999). It may be advantageous, where different protecting groups are employed, that each (different) protective group be removable by a different means. Protective groups that are cleaved under totally disparate reaction conditions allow differential removal of such protecting groups. For example, protective groups can be removed by acid, base, and hydrogenolysis. Groups such as trityl, dimethoxytrityl, acetal and tert-butyldimethylsilyl are acid labile and may be used to protect carboxy and hydroxy reactive moieties in the presence of amino groups protected with Cbz groups, which are removable by hydrogenolysis, and Fmoc groups, which are base labile. Carboxylic acid and hydroxy reactive moieties may be blocked with base labile groups such as, without limitation, methyl, ethyl, and acetyl in the presence of amines blocked with acid labile groups such as tert-butyl carbamate or with carbamates that are both acid and base stable but hydrolytically removable.

Carboxylic acid and hydroxy reactive moieties may also be blocked with hydrolytically removable protective groups such as the benzyl group, while amine groups capable of hydrogen bonding with acids may be blocked with base labile groups such as Fmoc. Carboxylic acid reactive moieties may be blocked with oxidatively-removable protective groups such as 2,4-dimethoxybenzyl, while co-existing amino groups may be blocked with fluoride labile silyl carbamates.

Allyl blocking groups are useful in the presence of acid- and base-protecting groups since the former are stable and can be subsequently removed by metal or pi-acid catalysts. For example, an allyl-blocked carboxylic acid can be deprotected with a palladium(O)— catalyzed reaction in the presence of acid labile t-butyl carbamate or base-labile acetate amine protecting groups. Yet another form of protecting group is a resin to which a compound or intermediate may be attached. As long as the residue is attached to the resin, that functional group is blocked and cannot react. Once released from the resin, the functional group is available to react.

Typical blocking/protecting groups include, but are not limited to the following moieties: p-Methoxybenzyl carbonyl (Moz or MeOZ), 3,4-dimethoxybenzyl (DMPM), Troc (trichloroethyl chloroformate), (4-nitrophenyl)sulfonyl (Nosyl), and nitrophenylsulfenyl (Nps), and

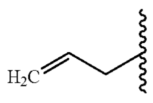

allyl

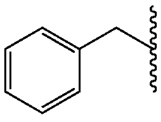

Bn

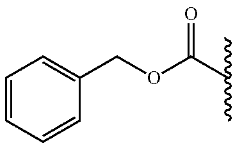

Cbz

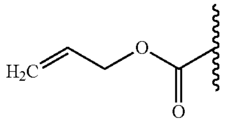

Alloc

Me

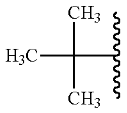

t-butyl

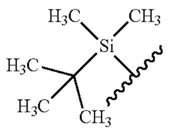

TBDMS

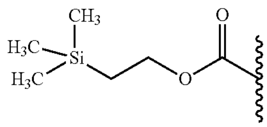

Teoc

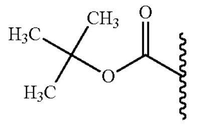

Boc

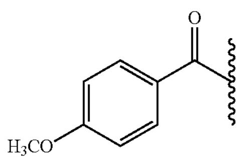

pMB

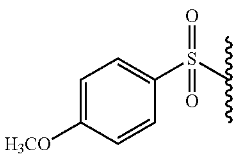

tosyl

-continued

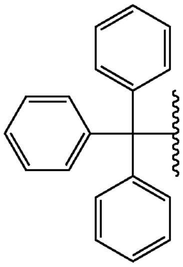

trityl

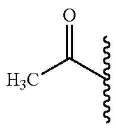

acetyl

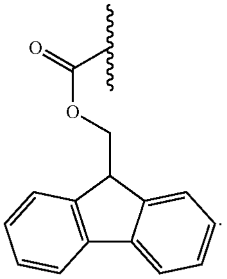

Fmoc

Following long-standing patent law convention, the terms "a," "an," and "the" refer to "one or more" when used in this application, including the claims. Thus, for example, reference to "a subject" includes a plurality of subjects, unless the context clearly is to the contrary (e.g., a plurality of subjects), and so forth.

Throughout this specification and the claims, the terms "comprise," "comprises," and "comprising" are used in a non-exclusive sense, except where the context requires otherwise. Likewise, the term "include" and its grammatical variants are intended to be non-limiting, such that recitation of items in a list is not to the exclusion of other like items that can be substituted or added to the listed items.

For the purposes of this specification and appended claims, unless otherwise indicated, all numbers expressing amounts, sizes, dimensions, proportions, shapes, formulations, parameters, percentages, quantities, characteristics, and other numerical values used in the specification and claims, are to be understood as being modified in all instances by the term "about" even though the term "about" may not expressly appear with the value, amount or range. Accordingly, unless indicated to the contrary, the numerical parameters set forth in the following specification and attached claims are not and need not be exact, but may be approximate and/or larger or smaller as desired, reflecting tolerances, conversion factors, rounding off, measurement error and the like, and other factors known to those of skill in the art depending on the desired properties sought to be obtained by the presently disclosed subject matter. For example, the term "about," when referring to a value can be meant to encompass variations of, in some embodiments, ±100% in some embodiments ±50%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Further, the term "about" when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter. The synthetic descriptions and specific examples that follow are only intended for the purposes of illustration, and are not to be construed as limiting in any manner to make compounds of the disclosure by other methods.

Example 1

Stability of Prodrugs in Mouse Skin Homogenate and Plasma

The mouse skin homogenate stability was performed using washed mouse skin diluted 10-fold in 0.1 M potassium phosphate buffer and homogenized using a tissue homogenizer or CD1 mice plasma. To evaluate the stability of the intact prodrug, 1 mL aliquot of the skin homogenate or plasma was spiked with prodrug to a final assay concentration of 20 μm. Spiked skin homogenate and plasma samples were incubated in an orbital shaker at 37° C. for 1 h, following which reactions were quenched in triplicate with three volumes of acetonitrile containing the internal standard (IS; losartan: 0.5 μm). The samples were vortex-mixed for 30 s and centrifuged at 10000×g for 10 min at 4° C. Fifty microliters of the supernatant was diluted with 50 μL of water and transferred to a 250 μL polypropylene vial sealed with a Teflon cap. Release itaconic acid or methyl itaconate were measured by liquid chromatography with tandem mass spectrometry (LC-MS/MS).

Example 2

Pharmacokinetics in Mice

Male CD1 mice (25-30 g) were obtained from Harlan and maintained on a 12 h light-dark cycle with ad libitum access to food and water. IS-100-142, MK939 and MK941 were administered at 10 mg/kg molar equivalent dose of monomethyl itaconate via oral gavage. Blood samples were collected at 0.25 and 1 h post dose (n=3 per time point). The mice were euthanized with carbon dioxide at specified time points post drug administration, blood samples (~0.8 mL) were collected in heparinized microtubes by cardiac puncture. Blood samples were centrifuged at a temperature of 4° C. at 3000×g for 10 min. Plasma samples (~300 μL) were collected in polypropylene tubes and stored at −80° C. until bioanalysis. Calibration standards were prepared using naïve mouse plasma spiked with monomethyl itaconate. Monomethyl itaconate standards and samples were extracted from plasma by a one-step protein precipitation using methanol (100% v/v) containing internal standard methyl succinate (5 μM). An aliquot of the supernatant (100 μL) was diluted with water (100 μL) and transferred to a 250 μL polypropylene vial sealed with a Teflon cap and analyzed via LC-MS/MS.

Example 3

Treatment of Human Keratinocytes with Itaconate Prodrugs

Neonatal human epidermal keratinocytes (NHEKs) isolates from neonatal foreskin were seeded at a density of 100,000 cells per well and were maintained in KGM supplemented with growth factors (KGM-GOLD Bullet kit, #192060). Prodrugs were reconstituted in DMSO. NHEKs were pre-treated with either vehicle (0.1% DMSO) or prodrug. After 2 days, NHEKs were treated with 50 ug/ul poly(I:C) for 24 hours.

Example 4

RNA Isolation and Quantitative Real-Time PCR

Total RNA was isolated and purified from cultured NHEKs using the RNeasy Mini Kit (Qiagen, Valencia, CA, #74106). After assessing RNA purity and concentrations using a NanoDrop 2000 UV-Vis spectrophotometer, RNA was converted to cDNA using a reverse-transcription kit and random hexamer primers (Applied Biosystems, #4368814). mRNA expression was determined by qRT-PCR using gene-specific, fluorophore-based TaqMan probes and universal master mix (Applied Biosystems, #4366072). The qRT-PCR reactions were multiplexed using target and reference gene (RPLPO) probes. Relative mRNA fold changes were then quantified using the ΔΔCt method.

Example 5

Representative Compounds (S)-4-((1-Ethoxy-1-oxo-3-phenylpropan-2-yl) amino)-2-methylene-4-oxobutanoic acid (IS-100-127)

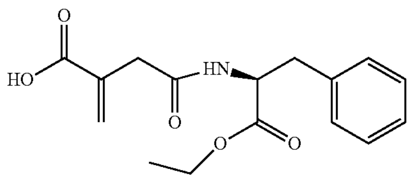 [SMILES: C=C(CC(=O)N[C@@H](Cc1ccccc1)C(=O)OCC)C(=O)O]

Itaconic anhydride (50 mg, 0.45 mmol) was dissolved in anhydrous THE (5 mL) and solid potassium carbonate (0.19 g, 1.34 mmol) followed by L-phenylalanine ethyl ester hydrochloride (0.1 g, 0.45 mmol) were added. Reaction mixture was stirred at room temperature for 16 hours. Volatiles were then evaporated, residue was redissolved in DCM (30 mL) and extracted with 1 M aqueous HCl (10 mL) and brine (10 mL). The organic phase was dried over $Na_2SO_4$, volatiles were evaporated and the residue was subjected to final purification on a reverse phase HPLCto afford 100 mg (73%) of the desired compound as a colorless semi-solid.

$^1$H NMR (401 MHz, DMSO-d$_6$): $\delta_H$ 1.25 (t, J=7.1 Hz, 3H), 3.13 (dd, J=13.9, 5.9 Hz, 2H), 3.28 (s, 2H), 4.18 (q, J=7.2 Hz, 2H), 4.86 (dt, J=7.8, 6.0 Hz, 1H), 5.90 (s, 1H), 6.46 (s, 1H), 6.65 (d, J=8.0 Hz, 1H), 7.06-7.38 (m, 5H), 9.98 (s, 1H).

ESI MS: 304.1 ([M-H]$^+$).

HRMS (ESI): Calcd. for $C_{16}H_{18}O_5N$ 304.11905. Found: 304.11910.

Methyl (S)-3-((1-ethoxy-1-oxo-3-phenylpropan-2-yl)carbamoyl)but-3-enoate (IS-100-128)

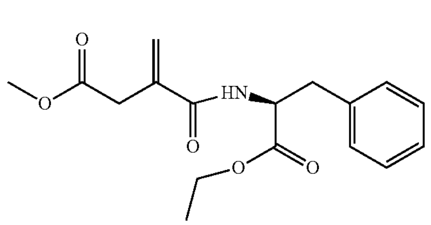 [SMILES: C=C(CC(=O)OC)C(=O)N[C@@H](Cc1ccccc1)C(=O)OCC]

β-Methyl itaconate (50 mg, 0.35 mmol) and HATU (0.13 g, 0.34 mmol) were dissolved in anhydrous DMF (3 mL), N,N-diisopropylethylamine (0.12 mL, 0.69 mmol) was added and the mixture was stirred for 5 minutes at room temperature. L-phenylalanine ethyl ester hydrochloride (80 mg, 0.35 mmol) was added and reaction mixture was stirred at room temperature for 3 hours. Volatiles were then evaporated, residue was redissolved in DCM (30 mL) and extracted with 1 M aqueous HCl (10 mL) and brine (10 mL). The organic phase was dried over $Na_2SO_4$, volatiles were evaporated and the residue was subjected to flash column chromatography (Silicagel 60 mesh 70-230, solvent: cyclohexane/ethyl acetate 2:1) to afford 100 mg (90%) of compound IS-100-128 as colorless semi-solid.

$^1$H NMR (401 MHz, DMSO-$d_6$): $\delta_H$ 1.27 (t, J=7.1 Hz, 3H), 3.19 (dd, J=5.7, 4.6 Hz, 2H), 3.37 (d, J=1.1 Hz, 2H), 3.69 (s, 3H), 4.20 (q, J=7.1 Hz, 2H), 4.90 (dt, J=7.6, 5.7 Hz, 1H), 5.50 (t, J=1.2 Hz, 1H), 5.74 (s, 1H), 6.60 (d, J=7.6 Hz, 1H), 7.09-7.19 (m, 2H), 7.21-7.36 (m, 3H).

$^{13}$C NMR (101 MHz, $CDCl_3$): $\delta_C$ 12.76, 36.46, 36.53, 50.77, 52.04, 60.20, 120.63, 125.72, 127.13, 128.06, 134.53, 136.59, 165.52, 169.86, 170.01.

ESI MS: 342.1 ([M+Na]$^+$).

HRMS (ESI): Calcd. for $C_{17}H_{22}O_5N$ 320.14925. Found: 320.14892.

Methyl (S)-3-((1-amino-1-oxo-3-phenylpropan-2-yl)carbamoyl)but-3-enoate (IS-100-129)

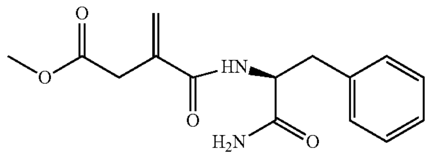 [SMILES: C=C(CC(=O)OC)C(=O)N[C@@H](Cc1ccccc1)C(N)=O]

β-Methyl itaconate (70 mg, 0.49 mmol) and HATU (0.18 g, 0.49 mmol) were dissolved in anhydrous DMF (5 mL), N,N-diisopropylethylamine (0.17 mL, 0.97 mmol) was added and the mixture was stirred for 5 minutes at room temperature. L-phenylalanine amide hydrochloride (97 mg, 0.49 mmol) was added and reaction mixture was stirred at room temperature for 3 hours. Volatiles were then evaporated, residue was redissolved in DCM (30 mL) and extracted with 1 M aqueous HCl (10 mL) and brine (10 mL). The organic phase was dried over $Na_2SO_4$, volatiles were evaporated and the residue was subjected to flash column chromatography (Silicagel 60 mesh 70-230, solvent: dichloromethane/methanol 20:1) to afford 120 mg (85%) of compound IS-100-129 as colorless semi-solid.

$^1$H NMR (401 MHz, DMSO-$d_6$): $\delta_H$ 3.14-3.31 (m, 3H), 3.46-3.56 (m, 1H), 3.68 (s, 3H), 4.77 (dt, J=8.0, 6.8 Hz, 1H), 5.43 (s, 1H), 5.57-5.63 (m, 1H), 5.67 (s, 1H), 6.38 (s, 1H), 6.67 (d, J=8.0 Hz, 1H), 7.21-7.38 (m, 5H). $^{13}$C NMR (101 MHz, $CDCl_3$): $\delta_C$ 37.45, 38.05, 52.24, 54.01, 121.42, 127.11, 128.76, 129.32, 136.60, 138.22, 167.87, 171.74, 173.19.

ESI MS: 313.1 ([M+Na]$^+$).

HRMS (ESI): Calcd. for $C_{15}H_{18}O_4N_2Na$ 313.11588. Found: 313.11545.

1-(((Isopropoxycarbonyl)oxy)methyl) 4-methyl 2-methylenesuccinate (IS-100-142)

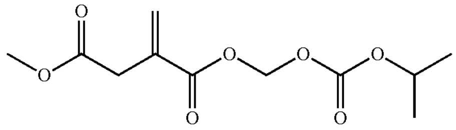 [SMILES: C=C(CC(=O)OC)C(=O)OCOC(=O)OC(C)C]

β-Methyl itaconate (0.2 g, 1.39 mmol), chloromethyl isopropyl carbonate (0.22 mL, 1.66 mmol) and potassium carbonate (0.29 g, 2.08 mmol) were dissolved in anhydrous MeCN (5 mL) and the mixture was stirred for 16 hours at room temperature. EtOAc (60 mL) was added and the mixture was washed with brine (20 mL). The organic phase was dried over $Na_2SO_4$, volatiles were evaporated and the residue was subjected to flash column chromatography (Silicagel 60 mesh 70-230, solvent: cyclohexane/ethyl acetate 5:1) to afford 90 mg (25%) of compound IS-100-142 as colorless oil.

$^1$H NMR (401 MHz, DMSO-$d_6$): $\delta_H$ 1.34 (d, J=6.3 Hz, 6H), 3.38 (s, 2H), 3.72 (s, 3H), 4.86-5.02 (m, 1H), 5.82-5.88 (m, 3H), 6.46 (s, 1H).

$^{13}$C NMR (101 MHz, $CDCl_3$): $\delta_C$ 21.64, 37.20, 52.12, 73.10, 82.20, 130.50, 132.76, 153.29, 164.52, 170.77.

ESI MS: 283.1 ([M+Na]$^+$).

HRMS (ESI): Calcd. for $C_{11}H_{16}O_7Na$ 283.07882. Found: 283.07855.

4-Methyl 1-((pivaloyloxy)methyl) 2-methylenesuccinate (IS-100-143)

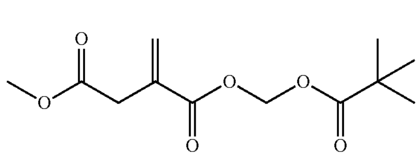 [SMILES: C=C(CC(=O)OC)C(=O)OCOC(=O)C(C)(C)C]

β-Methyl itaconate (0.2 g, 1.39 mmol), chloromethyl pivalate (0.26 mL, 1.8 mmol), sodium iodide (50 mg, 0.33 mmol) and potassium carbonate (0.29 g, 2.08 mmol) were dissolved in anhydrous MeCN (5 mL) and the mixture was stirred for 16 hours at 40° C. EtOAc (60 mL) was added and the mixture was washed with brine (20 mL). The organic phase was dried over $Na_2SO_4$, volatiles were evaporated and the residue was subjected to flash column chromatography (Silicagel 60 mesh 70-230, solvent: cyclohexane/ethyl acetate 5:1) to afford 0.33 g (92%) of compound IS-100-143 as colorless oil.

$^1H$ NMR (401 MHz, DMSO-$d_6$): $\delta_H$ 1.20 (s, 9H), 3.34 (s, 2H), 3.68 (s, 3H), 5.79 (d, J=1.1 Hz, 1H), 5.82 (s, 2H), 6.39 (s, 1H).

$^{13}C$ NMR (101 MHz, $CDCl_3$): $\delta_C$ 26.95, 37.38, 38.90, 52.21, 79.91, 130.30, 133.06, 164.82, 170.90, 177.19.

ESI MS: 281.1 ($[M+Na]^+$).

HRMS (ESI): Calcd. for $C_{12}H_{18}O_6Na$ 281.09956. Found: 281.09921.

1-(tert-Butyl) 4-((pivaloyloxy)methyl) 2-methylene-succinate (IS-100-146)

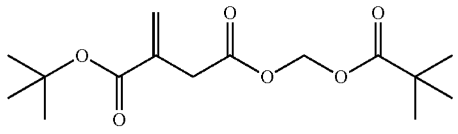 [SMILES: C=C(CC(=O)OCOC(=O)C(C)(C)C)C(=O)OC(C)(C)C]

3-(tert-Butoxycarbonyl)but-3-enoic acid (0.2 g, 1.07 mmol), chloromethyl pivalate (0.2 mL, 1.4 mmol), sodium iodide (30 mg, 0.21 mmol) and potassium carbonate (0.22 g, 1.61 mmol) were dissolved in anhydrous MeCN (4 mL) and the mixture was stirred for 16 hours at 45° C. EtOAc (60 mL) was added and the mixture was washed with brine (20 mL). The organic phase was dried over $Na_2SO_4$, volatiles were evaporated and the residue was subjected to flash column chromatography (Silicagel 60 mesh 70-230, solvent: cyclohexane/ethyl acetate 6:1) to afford 0.23 g (71%) of compound IS-100-143 as colorless oil.

$^1H$ NMR (401 MHz, DMSO-$d_6$): $\delta_H$ 1.21 (s, 9H), 1.48 (s, 9H), 3.33 (d, J=1.2 Hz, 2H), 5.63 (d, J=1.2 Hz, 1H), 5.76 (s, 2H), 6.25 (d, J=1.0 Hz, 1H).

$^{13}C$ NMR (101 MHz, $CDCl_3$): $\delta_C$ 27.00, 28.10, 37.72, 38.90, 79.88, 81.44, 127.92, 134.86, 165.13, 169.79, 177.23.

ESI MS: 323.2 ($[M+Na]^+$).

HR ESI MS: Calcd. for $C_{15}H_{24}O_6Na$ 323.14651. Found: 323.14622.

2-Methylene-4-oxo-4-((pivaloyloxy)methoxy)butanoic acid (IS-100-147)

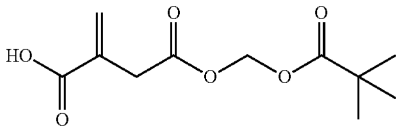 [SMILES: C=C(CC(=O)OCOC(=O)C(C)(C)C)C(=O)O]

1-(tert-Butyl) 4-((pivaloyloxy)methyl) 2-methylenesuccinate (0.14 g, 0.47 mmol) was dissolved in anhydrous DCM (0.5 mL) with trifluoroacetic acid (4 mL) and the mixture was stirred for 2 hours at room temperature. Volatiles were evaporated and the residue was dissolved in DCM (3×15 mL) evaporated three times to afford 0.11 g (97%) of compound IS-100-147 as colorless oil.

$^1H$ NMR (401 MHz, DMSO-$d_6$): $\delta_H$ 1.21 (s, 9H), 3.37 (s, 2H), 5.77 (s, 2H), 5.87 (s, 1H), 6.49 (s, 1H), 11.12 (s, 1H).

$^{13}C$ NMR (101 MHz, $CDCl_3$): $\delta_C$ 26.81, 36.97, 38.76, 79.66, 131.36, 132.54, 169.22, 171.11, 177.13.

ESI MS: 267.1 ($[M+Na]^+$).

HRMS (ESI): Calcd. for $C_{11}H_{16}O_6Na$ 267.08391. Found: 267.08375.

Bis((pivaloyloxy)methyl) 2-methylenesuccinate (IS-100-148)

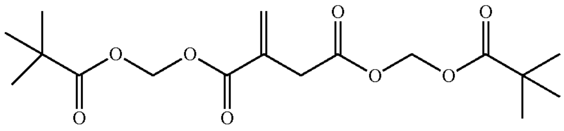 [SMILES: C=C(CC(=O)OCOC(=O)C(C)(C)C)C(=O)OCOC(=O)C(C)(C)C]

Itaconic acid (0.2 g, 1.53 mmol), chloromethyl pivalate (0.55 mL, 3.84 mmol), sodium iodide (50 mg, 0.3 mmol) and potassium carbonate (0.64 g, 4.60 mmol) were dissolved in anhydrous MeCN (5 mL) and the mixture was stirred for 16 hours at 45° C. EtOAc (60 mL) was added and the mixture was washed with brine (20 mL). The organic phase was dried over $Na_2SO_4$, volatiles were evaporated and the residue was subjected to flash column chromatography (Silicagel 60 mesh 70-230, solvent: cyclohexane/ethyl acetate 5:1) to afford 0.20 g (36%) of compound IS-100-148 as colorless oil.

$^1H$ NMR (401 MHz, DMSO-$d_6$): $\delta_H$ 1.20 (s, 18H), 3.38 (d, J=1.0 Hz, 2H), 5.74 (s, 2H), 5.82 (s, 3H), 6.41 (s, 1H).

$^{13}C$ NMR (101 MHz, $CDCl_3$): $\delta_C$ 26.83, 26.84, 37.12, 38.75, 38.78, 79.70, 79.82, 130.52, 132.33, 164.45, 169.12, 177.07.

ESI MS: 381.2 ($[M+Na]^+$).

HRMS (ESI): Calcd. for $C_{17}H_{26}O_8Na$ 381.15199. Found: 381.15158.

Bis(((isopropoxycarbonyl)oxy)methyl) 2-methylene-succinate (IS-100-149)

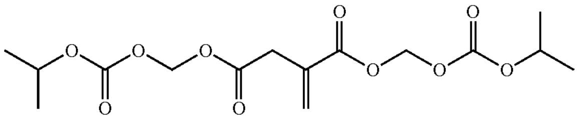 [SMILES: C=C(CC(=O)OCOC(=O)OC(C)C)C(=O)OCOC(=O)OC(C)C]

Itaconic acid (0.2 g, 1.53 mmol), chloromethyl isopropyl carbonate (0.51 mL, 3.84 mmol), sodium iodide (50 mg, 0.3 mmol) and potassium carbonate (0.64 g, 4.60 mmol) were dissolved in anhydrous MeCN (5 mL) and the mixture was stirred for 16 hours at 45° C. EtOAc (60 mL) was added and the mixture was washed with brine (20 mL). The organic phase was dried over $Na_2SO_4$, volatiles were evaporated and the residue was subjected to flash column chromatography (Silicagel 60 mesh 70-230, solvent: cyclohexane/ethyl acetate 5:1) to afford 80 mg (14%) of compound IS-100-149 as colorless oil.

$^1H$ NMR (401 MHz, DMSO-$d_6$): $\delta_H$ 1.31 (d, J=6.3 Hz, 12H), 3.41 (s, 2H), 4.82-4.98 (m, 2H), 5.75 (s, 2H), 5.82 (s, 2H), 5.85 (s, 1H), 6.46 (s, 1H).

$^{13}C$ NMR (101 MHz, $CDCl_3$): $\delta_C$ 21.63, 36.95, 73.13, 82.00, 82.22, 131.05, 131.99, 153.26, 153.29, 164.28, 168.95.

ESI MS: 385.1 ($[M+Na]^+$).

HRMS (ESI): Calcd. for $C_{15}H_{22}O_{10}Na$ 385.11052. Found: 385.11069.

4-Methyl 1-((5-methyl-2-oxo-1,3-dioxol-4-yl) methyl 2-methylenesuccinate (LTP1025)

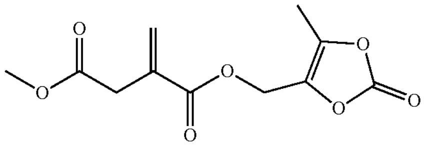 [SMILES: C=C(CC(=O)OC)C(=O)OCc1oc(=O)oc1C]

β-Methyl itaconate (200 mg, 1.39 mmol) was dissolved in anhydrous MeCN (5 mL), $K_2CO_3$ (384 mg, 2.78 mmol, 2 equiv.) and NaI (416 mg, 2.78 mmol, 2 equiv.) were added and the resulting mixture was heated to 40° C. for 10 minutes under inert. Finally (4-chloromethyl)-5-methyl-1,3-dioxol-2-one (412 mg, 303 μL, 2.78 mmol, 2 equiv.) was added and the mixture was heated to 40° C. for 48 h. MeCN was evaporated, EtOAc (50 mL) was added and the organic phase was washed with 10% $Na_2S_2O_5$ (50 mL), distilled $H_2O$ (50 mL) and sat. NaCl (2×50 mL). The organic phase was dried over $MgSO_4$, volatiles were evaporated and the residue was subjected to flash column chromatography (Silicagel 60 mesh 70-230, solvent: cyclohexane/EtOAc, 2:1) to afford 320 mg (90%) of compound LTP1025 as a light yellow oil.

$^1H$ NMR (401 MHz, $CDCl_3$): $\delta_H$ 2.15 (s, 3H), 3.31 (s, 2H), 3.65 (s, 3H), 4.89 (s, 2H), 5.75 (s, 1H), 6.33 (s, 1H).

$^{13}C$ NMR (101 MHz, $CDCl_3$): $\delta_C$ 9.36, 37.36, 52.12, 54.28, 129.98, 132.99, 133.36, 140.30, 152.11, 165.51, 170.91.

ESI MS: 279.1 ([M+Na]+).

HRMS (ESI): Calcd. for $C_{11}H_{12}O_7Na$ 279.04752. Found: 279.04757.

Alkyl β-Methyl Itaconates

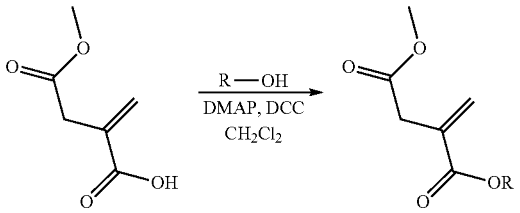

R=alkyl, aryl, alkyl salicylyl, Boc-tyrosyl alkylamide, Boc-tyrosyl ester, (di)peptide with terminal tyrosyl ester, (di)peptide with terminal tyrosyl alkylamide

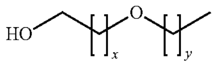

x= 1-3
y= 13-17

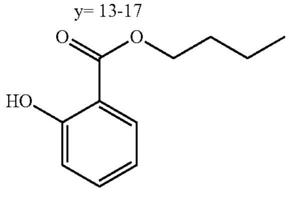

-continued

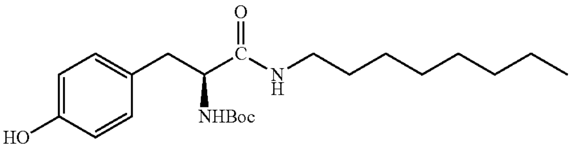

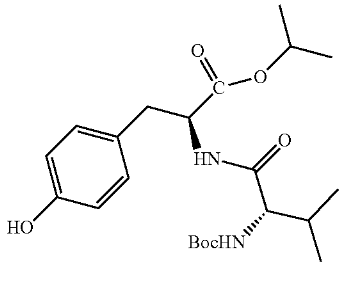

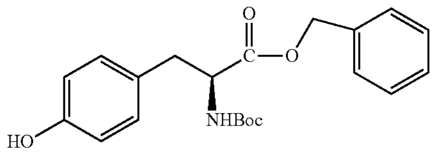

Examples of R—OH for the Alkyl β-Methyl Itaconates Include, but are not Limited to:

General procedure was performed according to the modified process described in Boschert, D.; Schneider-Chaabane, A.; Himmelsbach, A.; Eickenscheidt, A.; Lienkamp, K. Synthesis and Bioactivity of Polymer-Based Synthetic Mimics of Antimicrobial Peptides (SMAMPs) Made from Asymmetrically Disubstituted Itaconates. *Chem. Eur. J.* 2018, 24, 8217-8227.

L-tyrosyl alkylamides were synthesized according to McKenna, C. E.; Kashemirov, B. A; Krylov, I. S.; Zakharova, V. M. Method to improve antiviral activity of nucleotide analogue drugs. U.S. Pat. No. 9,550,803 B2, Jan. 24, 2017; and Hidaka, K.; Gohda, K.; Teno, N.; Wanaka, K.; Tsuda, Y. Active site-directed plasmin inhibitors: Extension on the P2 residue. *Bioorg. Med. Chem.* 2016, 24, 545-553.

β-Methyl itaconate (1 mmol) was dissolved in dry dichloromethane (3 mL). Appropriate hydroxy derivative (1.2 mmol) and DMAP (1.5 mmol) were added and the solution cooled to 0° C. A solution of DCC (1.5 mmol) in dichloromethane (2 mL) was added dropwise under nitrogen and the whole mixture stirred for 1 h at 0° C. and then overnight at room temperature. The mixture was filtered, the solution extracted with 10% aqueous $KHSO_4$ (3×5 mL) and saturated $NaHCO_3$ (5 mL). The organic phase was dried over sodium sulfate, evaporated and the residue chromatographed on a column of silica gel in system described below.

1-(2-(Hexadecyloxy)ethyl) 4-methyl 2-methylene-succinate (MK-933)

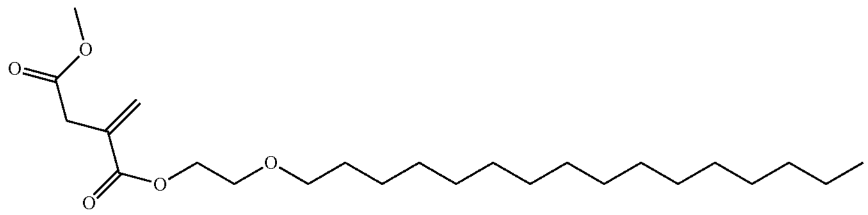 [SMILES: C=C(CC(=O)OC)C(=O)OCCOCCCCCCCCCCCCCCCC]

Chromatography in system cyclohexane—ethyl acetate (80:15). Yield: 253 mg (61%) of a colorless liquid.

$^1$H NMR ($CDCl_3$, ppm) δ: 0.88 (t, 3H, $J_{CH3,CH2}$=7.1, $CH_3$ (18')), 1.38-1.20 (m, 26H, 13×$CH_2$ (5'-17')), 1.57 (m, 2H, $CH_2$ (4')), 3.35 (d, 2H, $J_{2,=CH}$=1.1, $CH_2$ (2)), 3.46 (t, 2H, $J_{3',4'}$=6.7, $OCH_2$ (3')), 3.65 (m, 2H, $OCH_2$ (2')), 3.69 (s, 3H, $OCH_3$), 4.30 (m, 2H, $OCH_2$ (1')), 5.73 (q, 1H, $J_{gem}$=$J_{H,2}$=1.1, =$CH_a$), 6.37 (m, 1H, =$CH_b$).

$^{13}$C NMR ($CDCl_3$, ppm) δ: 14.11 (C-18'), 22.68 (C-17'), 26.05 (C-5'), 29.35, 29.46, 29.61 and 29.68 (C-4', C-6'-C-15'), 31.91 (C-16'), 37.48 (C-2), 52.03 ($OCH_3$), 64.29 (C-1'), 68.39 (C-2'), 71.46 (C-3'), 128.74 (=$CH_2$), 133.64 (C-3), 166.08 (C-4), 171.11 (C-1).

CI MS: 413.3 $(MH)^+$ (60).

HRMS (CI): For $C_{24}H_{45}O_5(MH)^+$ calculated: 413.3267; found: 413.3264.

4-Methyl 1-(4-(tetradecyloxy)butyl) 2-methylene-succinate (MK-937)

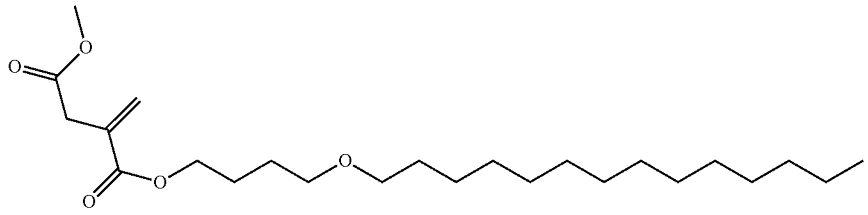 [SMILES: C=C(CC(=O)OC)C(=O)OCCCCOCCCCCCCCCCCCCC]

Chromatography in system cyclohexane—ethyl acetate (7:1). Yield: 259 mg (63%) of a colorless liquid.

$^1$H NMR ($CDCl_3$, ppm) δ: 0.87 (t, 3H, $J_{CH3,CH2}$=7.1, $CH_3$ (18')), 1.37-1.20 (m, 22H, 11×$CH_2$ (7'-17')), 1.55 (m, 2H, $CH_2$ (6')), 1.64 (m, 2H, $CH_2$ (3')), 1.74 (m, 2H, $CH_2$ (2')), 3.33 (d, 2H, $J_{2,=CH}$=1.1, $CH_2$ (2)), 3.38 (t, 2H, $J_{5',6'}$=6.7, $OCH_2$ (5')), 3.42 (t, 2H, $J_{4',3'}$=6.4, $OCH_2$ (4')), 3.69 (s, 3H, $OCH_3$), 4.18 (t, 2H, $J_{1',2'}$=6.6, $OCH_2$ (1')), 5.70 (q, 1H, $J_{gem}$=$J_{Ha,2}$=1.1, =$CH_a$), 6.32 (m, 1H, =$CH_b$).

$^{13}$C NMR ($CDCl_3$, ppm) δ: 14.10 (C-18'), 22.67 (C-17'), 25.46 (C-2'), 26.17 and 26.21 (C-3', C-7'), 29.34, 29.49, 29.60, 29.65 and 29.73 (C-6' and C-8'-C-15'), 31.90 (C-16'), 37.53 (C-2), 52.01 ($OCH_3$), 64.93 (C-1'), 70.10 (C-4'), 71.05 (C-5'), 128.36 (=$CH_2$), 133.89 (C-3), 166.11 (C-4), 171.15 (C-1).

CI MS: 412.3 $(M)^+$ (6).

HRMS (CI): For $C_{24}H_{44}O_5$ $(M)^+$ calculated: 412.3189; found: 412.3187.

1-(2-(Butoxycarbonyl)phenyl) 4-methyl 2-methyl-enesuccinate (MK-939)

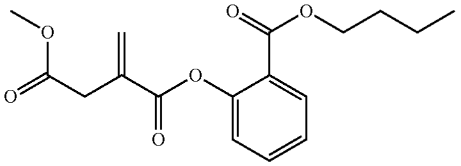 [SMILES: C=C(CC(=O)OC)C(=O)Oc1ccccc1C(=O)OCCCC]

Chromatography in system cyclohexane—ethyl acetate (6:1). Yield: 230 mg (72%) of a colorless liquid.

$^1$H NMR ($CDCl_3$, ppm) δ: 0.94 (t, 3H, $CH_3$ (4')), 1.42 (m, 2H, $CH_2$ (3')), 1.67 (m, 2H, $CH_2$ (2')), 3.48 (d, 2H, $J_{CH2,H}$=1.1, $CH_2$—C=O), 3.73 (s, 3H, $OCH_3$), 4.25 (t, 2H, $J_{1',2'}$=6.7, $OCH_2$ (1')), 5.94 (q, 1H, $J_{gem}$=$J_{Ha,CH2}$=1.1, =$CH_a$), 6.62 (m, 1H, =$CH_b$), 7.14 (ddd, 1H, $J_{3,4}$=8.1, $J_{3,5}$=1.2, $J_{3,6}$=0.6, H-3), 7.32 (ddd, 1H, $J_{5,6}$=7.9, $J_{5,4}$=7.4, $J_{5,3}$=1.2, H-5), 7.56 (ddd, 1H, $J_{4,3}$=8.1, $J_{4,5}$=7.4, $J_{4,6}$=1.7, H-4), 8.02 (ddd, 1H, $J_{6,5}$=7.9, $J_{6,4}$=1.7, $J_{6,3}$=0.3, H-6).

$^{13}$C NMR ($CDCl_3$, ppm) δ: 13.70 (C-4'), 19.16 (C-3'), 30.60 (C-2'), 37.43 $CH_2$C=O), 52.09 ($OCH_3$), 65.05 (C-1'), 123.70 (C-1), 123.80 (C-3), 126.06 (C-5), 130.41 (=$CH_2$), 131.74 (C-6), 133.18 (C=$CH_2$), 133.64 (C-4), 150.43 (C-2), 164.52 (COOBu), 164.70 (COOPh), 170.95 (COOMe).

ESI MS: 343.1 $(M+Na)^+$ (100).

HRMS (ESI): For $C_{17}H_{20}O_6Na$ $(M+Na)^+$ calculated: 343.11521; found: 343.11487.

(S)-1-(4-(2-((tert-Butoxycarbonyl)amino)-3-(octylamino)-3-oxopropyl)phenyl) 4-methyl 2-methylenesuccinate (MK-940)

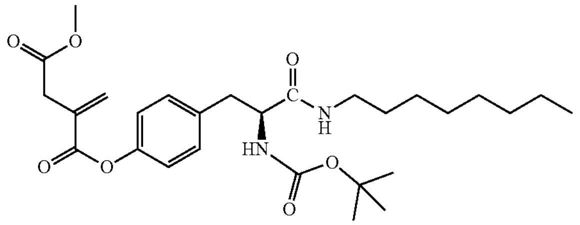 [SMILES: C=C(CC(=O)OC)C(=O)Oc1ccc(C[C@H](NC(=O)OC(C)(C)C)C(=O)NCCCCCCCC)cc1]

Chromatography in system cyclohexane—ethyl acetate (2:1), followed by additional chromatography in system 1.5% MeOH in $CHCl_3$. Yield: 325 mg (63%) of a white amorphous solid.

$^1$H NMR ($CDCl_3$, ppm) δ: 0.86 (t, 3H, $J_{CH3,CH2}$=7.1, $CH_3$ (11')), 1,14-1.31 (m, 10H, 5×$CH_2$ (6'-10')), 1.36 (m, 2H, $CH_2$ (5')), 1.41 (s, 9H, $CH_3$ (t-Bu)), 3.02 and 3.06 (m, 2H, $CH_2$ (tyrosine)), 3.14 (m, 2H, $CH_2$ (4')), 3.44 (s, 2H, $CH_2$—C═O), 3.71 (s, 3H, $OCH_3$), 4.25 (m, 1H, CH—NH (2')), 5.09 (bs, 1H, 2'-NH), 5.83 (bs, 1H, 3'-NH), 5.88 (m, 1H, ═$CH_a$), 6.53 (s, 1H, ═$CH_b$), 7.04 (d, 2H, $J_{2,3}$=8.4, H-2 (arom.), 7.21 (d, 2H, $J_{3,2}$=8.4, H-3 (arom.)).

$^{13}$C NMR ($CDCl_3$, ppm) δ: 14.04 (C-11'), 22.58 (C-10'), 26.75 (C-6'), 28.24 ($CH_3$ (t-Bu)), 29.10, 29.13 and 29.32 (C-5', C-7', C-8'), 31.74 (C-9'), 37.48 ($CH_2$C═O), 37.91 (C-1'), 39.49 (C-4'), 52.11 ($OCH_3$), 55.90 (C-2'), 80.16 ($C(CH_3)_3$), 121.59 (C-2), 130.08 (═$CH_2$), 130.29 (C-3), 133.36 (C═$CH_2$), 134.51 (C-4), 149.61 (C-1), 155.38 (NH—COO), 164.60 (COOPh), 170.75 and 170.91 (C-3', $CH_3$O—C═O).

ESI MS: 1059.6 (2M+Na)+(10), 541.3 $(M+Na)^+$ (100).

HRMS (ESI): For $C_{28}H_{42}O_7N_2Na$ $(M+Na)^+$ calculated: 541.28842; found: 541.28735.

1-(4-((S)-2-((S)-2-((tert-butoxycarbonyl)amino)-3-methylbutanamido)-3-isopropoxy-3-oxopropyl)phenyl) 4-methyl 2-methylenesuccinate (MK-942)

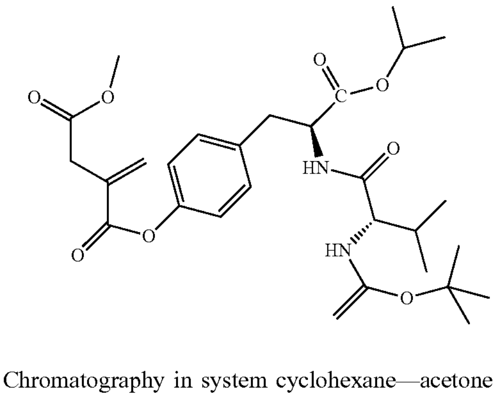

Chromatography in system cyclohexane—acetone (4:1). Yield: 420 mg (77%) of a white solid.

$^1$H NMR (DMSO-$d_6$, ppm) δ: 0.77-0.80 (m, 6H, $CH(CH_3)_2$), 1.05 and 1.13 (2× d, 6H, $J_{CH3,CH}$=6.3, OCH$(CH_3)_2$), 1.37 (s, 9H, $C(CH_3)_3$), 1.85 (m, 1H, $CH(CH_3)_2$), 2.94 (dd, 1H, $J_{3'a,2'}$=8.5, $J_{gem}$=13.9, H-3'a), 3.00 (dd, 1H, $J_{3'b,2'}$=6.4, $J_{gem}$=13.9, H-3'b), 3.50 (s, 2H, $CH_2$—COOMe), 3.62 (s, 3H, $OCH_3$), 3.80 (dd, 1H, $J_{2'',NH}$=9.2, $J_{2'',3''}$=7.1, H-2"), 4.42 (m, 1H, H-2'), 4.81 (sept, 1H, $J_{CH,CH3}$=6.3, $OCH(CH_3)_2$), 6.02 and 6.42 (2× d, 2H, $J_{gem}$=1.1, ═$CH_2$), 6.60 (d, 1H, $J_{NH,2''}$=9.2, NH-2"), 7.00 (m, 2H, H-arom. (2)), 7.28 (m, 2H, H-arom. (3)), 8.29 (d, $J_{NH,2'}$=7.5, NH-2').

$^{13}$C NMR (DMSO-$d_6$, ppm) δ: 18.39 and 19.35 (C-4"), 21.54 and 21.69 (O—$CH(CH_3)_2$), 28.38 ($C(CH_3)_3$), 30.73 (C-3"), 36.24 (C-3'), 37.16 ($CH_2$—COOMe), 52.01 ($OCH_3$), 53.70 (C-2'), 59.61 (C-2"), 68.23 (O—$CH(CH_3)_2$), 78.16 ($C(CH_3)_3$), 121.43 (C-2), 130.47 (C-3), 130.88 (═$CH_2$), 133.59 (C═$CH_2$), 135.00 (C-4), 149.24 (C-1), 155.50 (NH—COO), 164.61 (COO-Ph), 170.96 and 171.02 (C-1', COOMe), 171.63 (C-1").

ESI MS: 571.3 $(M+Na)^+$ (100), 549.3 $(MH)^+$ (2).

HRMS (ESI): For $C_{28}H_{40}O_9N_2Na$ $(M+Na)^+$ calculated: 571.26260; found: 571.26247.

(S)-1-(4-(3-(Benzyloxy)-2-((tert-butoxycarbonyl)amino)-3-oxopropyl)phenyl) 4-methyl 2-methylenesuccinate (MK-943)

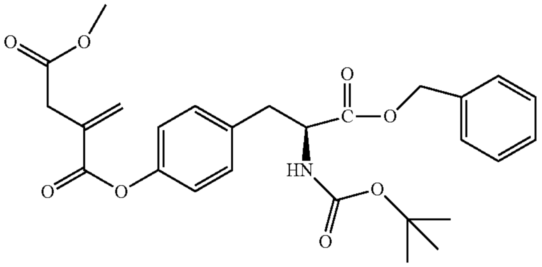 [SMILES: C=C(CC(=O)OC)C(=O)Oc1ccc(C[C@H](NC(=O)OC(C)(C)C)C(=O)OCc2ccccc2)cc1]

Chromatography in system cyclohexane—acetone (4:1). Yield: 439 mg (88%) of a colorless syrup.

$^1$H NMR (DMSO-$d_6$, ppm) δ: 1.32 (s, 9H, $C(CH_3)_3$), 2.90 (dd, 1H, $J_{3'a,2'}$=10.0, $J_{gem}$=13.8, H-3'a), 3.02 (dd, 1H, $J_{3'b,2'}$=5.4, $J_{gem}$=13.8, H-3'b), 3.51 (s, 2H, $CH_2$—COOMe), 3.63 (s, 3H, $OCH_3$), 4.21 (ddd, 1H, $J_{2',3'}$=10.0 and 5.4, $J_{2',NH}$=8.0, (H-2'), 5.10 (s, 2H, O—$CH_2$Ph), 6.04 and 6.43 (2× d, 2H, $J_{gem}$=1.1, ═$CH_2$), 7.02 (m, 2H, H-2 (arom.)), 7.27-7.37 (m, 7H, H-3, H-2", H-3", H-4"(arom.)), 7.41 (bd, 1H, $J_{NH,CH}$=8.0, NH).

$^{13}$C NMR (DMSO-$d_6$, ppm) δ: 28.33 ($C(CH_3)_3$), 35.85 (C-3'), 37.18 ($CH_2$—COOMe), 52.04 ($OCH_3$), 55.60 (C-2'), 66.17 (O—$CH_2$Ph), 78.60 ($C(CH_3)_3$), 121.51 (C-2), 128.05 (C-2"), 128.24 (C-4"), 128.59 (C-3"), 130.46 (C-3), 130.95 (═$CH_2$), 133.59 (C═$CH_2$), 135.48 (C-4), 136.06 (C-1"), 149.21 (C-1), 155.68 (NH—CO), 164.68 (COO—C(1)), 171.04 (COO-Me), 172.19 (C-1').

ESI MS: 1017.5 $(2M+Na)^+$ (15), 520.2 $(M+Na)^+$ (100).

HRMS (ESI): For $C_{27}H_{31}O_8NNa$ $(M+Na)^+$ calculated: 520.19419; found: 520.19394.

Deprotection of Tert-Butoxycarbonyl (Boc) Group. General Procedure.

A mixture of dichloromethane and trifluoroacetic acid (1:1, 16 mL) was added to appropriate Boc derivative (0.8 mmol). The solution was stirred at room temperature for 20 min and evaporated. The residue was crystallized (MK-944), or chromatographed on a silica gel column (100 mL) in system described below, followed by purification on a reverse phase HPLC and lyophilization (compounds MK-941, MK-945).

The following compounds were synthesized:

(S)-1-(4-(2-amino-3-(octylamino)-3-oxopropyl)phenyl) 4-methyl 2-methylenesuccinate, trifluoroacetate salt (MK-941)

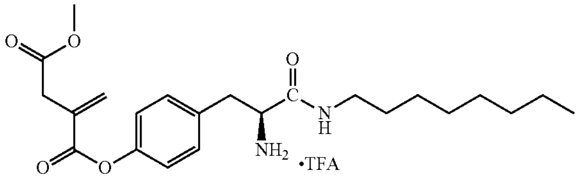 [SMILES: C=C(CC(=O)OC)C(=O)Oc1ccc(C[C@H](N)C(=O)NCCCCCCCC)cc1]

Chromatography in system ethyl acetate—methanol (15:2) gave 183 mg (43%) of yellowish foam which was subjected to final purification on a reverse phase HPLC (gradient 20 to 60% $CH_3CN$ in 0.1% TFA/$H_2O$ during 40 min, retention time 36.8 min). Yield: 124 mg (29%) of a white solid.

$^1H$ NMR (DMSO-$d_6$, ppm) δ: 0.85 (t, 3H, $J_{CH3,CH2}$=7.0, $CH_3$), 1.11-1.32 (m, 12H, 6×$CH_2$ (2"-7")), 2.94 (m, 1H, NH—$CH_a$), 3.00 (m, 2H, Ph-$CH_2$), 3.11 (m, 1H, NH—$CH_b$), 3.51 (s, 2H, $CH_2$COOMe), 3.63 (s, 3H, $OCH_3$), 3.91 (m, 1H, CH—$NH_3^+$), 6.05 and 6.42 (2×d, $J_{gem}$=1.1, =$CH_2$), 7.08 (m, 2H, H-2 (arom.)), 7.26 (m, 2H, H-3 (arom.)), 8.22 (bs, 3H, $NH_3^+$), 8.31 (bt, 1H, $J_{NH,1''}$=5.6, NH).

$^{13}C$ NMR (DMSO-$d_6$, ppm) δ: 14.44 ($CH_3$ (8")), 22.57 ($CH_2$ (7")), 26.76 ($CH_2$ (3")), 29.07, 29.13 and 29.15 ($CH_2$ (2",4",5")), 31.73 ($CH_2$ (6")), 36.93 (Ph-$CH_2$), 37.37 ($CH_2$COOMe), 39.12 (NH—$CH_2$), 52.26 ($OCH_3$), 53.96 (CH—$NH_3^+$), 122.04 (C-2 (arom.)), 131.05 (C-3 (arom.)), 131.21 (=$CH_2$), 133.12 (C-4 (arom.)), 133.80 (C=$CH_2$), 149.98 (C-1 (arom.)), 164.80 (COO), 167.89 (NH—C=O), 171.26 (COOMe).

ESI MS: 441.2 $(M+Na)^+$ (100), 419.3 $(MH)^+$ (35).

HRMS (ESI): For $C_{23}H_{34}O_5N_2Na$ $(M+Na)^+$ calculated: 441.23599; found: 441.23569. For $C_{23}H_{35}O_5N_2$ $(MH)^+$ calculated: 419.25405; found: 419.25385.

1-(4-((S)-2-((S)-2-amino-3-methylbutanamido)-3-isopropoxy-3-oxopropyl)phenyl) 4-methyl 2-methylenesuccinate, trifluoroacetate salt (MK-944)

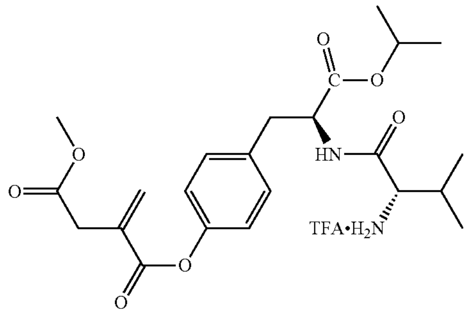

Crystallization from ethyl—acetate with addition of diethyl ether. Yield: 324 mg (72%) of white crystals.

$^1H$ NMR (DMSO-$d_6$, ppm) δ: 0.93 and 0.97 (2×d, 6H, $J_{CH3,CH}$=6.9, $CH(CH_3)_2$), 1.07 and 1.15 (2× d, 6H, $J_{CH3,CH}$=6.2, O—$CH(CH_3)_2$), 2.13 (m, 1H, $CH(CH_3)_2$), 2.99 (dd, 1H, $J_{3'a,2'}$=8.3, $J_{gem}$=14.1, H-3'a), 3.04 (dd, 1H, $J_{3'b,2'}$=6.3, $J_{gem}$=14.1, H-3'b), 3.51 (s, 2H, CH—COOMe), 3.63 (s, 3H, $OCH_3$), 3.65 (d, 1H, $J_{2'',3''}$=5.1, H-2"), 4.50 (m, 1H, H-2'), 4.85 (sept, 1H, $J_{CH,CH3}$=6.2, O—$CH(CH_3)_2$), 6.04 and 6.43 (2× m, 2H, =$CH_2$), 7.05 (m, 2H, H-2), 7.32 (m, 2H, H-3), 8.09 (bs, 3H, $NH_3^+$), 8.90 (d, 1H, $J_{NH,2'}$=7.0, NH).

$^{13}C$ NMR (DMSO-$d_6$, ppm) δ: 17.44 and 18.56 (C-4"), 21.52 and 21.69 (O—$CH(CH_3)_2$), 30.10 (C-3"), 36.03 (C-3'), 37.16 ($CH_2$—COOMe), 52.03 ($OCH_3$), 54.27 (C-2'), 57.24 (C-2"), 68.66 (O—$CH(CH_3)_2$), 121.66 (C-2), 130.53 (C-3), 131.04 (=$CH_2$), 133.54 (C=$CH_2$), 134.68 (C-4), 149.41 (C-1), 164.71 (COO-Ph), 168.41 (NH—CO), 170.56 (COO-iPr), 171.07 (COOMe).

ESI MS: 471.2 $(M+Na)^+$ (58), 449.2 $(MH)^+$ (100).

HRMS (ESI): For $C_{23}H_{32}O_7N_2Na$ $(M+Na)^+$ calculated: 471.21017; found: 471.20999. For $C_{23}H_{33}O_7N_2$ $(MH)^+$ calculated: 449.22823; found: 449.22815.

(S)-1-(4-(2-amino-3-(benzyloxy)-3-oxopropyl)phenyl) 4-methyl 2-methylenesuccinate, trifluoroacetate salt (MK-945)

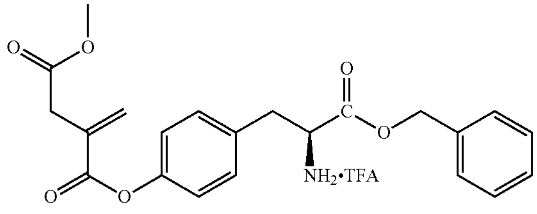

Chromatography in system dichloromethane—methanol (50:2) gave 270 mg (68%) of a yellowish syrup which was subjected to final purification on a reverse phase HPLC (gradient 15 to 50% $CH_3CN$ in 0.1% TFA/$H_2O$ during 40 min, retention time 37.1 min). Yield: 85 mg (21%) of a gummy semi-solid.

$^1H$ NMR (DMSO-$d_6$, ppm) δ: 3.08 (dd, 1H, $J_{3'a,2'}$=7.7, $J_{gem}$=14.1, H-3'a), 3.16 (dd, 1H, $J_{3'b,2'}$=6.0, $J_{gem}$=14.1, H-3'b), 3.53 (s, 2H, $CH_2$—COOMe), 3.63 (s, 3H, $OCH_3$), 4.40 (dd, 1H, $J_{2',3'}$=7.6 and 6.1, H-2'), 5.13 and 5.17 (2× d, 2H, $J_{gem}$=12.3, O—$C_2$Ph), 6.06 and 6.45 (2× d, 2H, $J_{gem}$=1.1, =$CH_2$), 7.05 (m, 2H, H-2 (arom.)), 7.24 (m, 2H, H-3 (arom.)), 7.26 (m, 2H, H-2"), 7.34-7.38 (m, 3H, H-3", H-4"(arom.)), 8.58 (bs, 3H, $NH_3^+$).

$^{13}C$ NMR (DMSO-$d_6$, ppm) δ: 35.68 (C-3'), 37.21 ($CH_2$—COOMe), 52.07 ($OCH_3$), 53.35 (C-2'), 67.44 (O—$CH_2$Ph), 121.97 (C-2), 128.05 (C-2"), 128.67-128.69 (C-2", C-3", C-4"), 130.87 (C-3), 131.13 (=$CH_2$), 132.48 (C-4), 133.56 (C=$CH_2$), 135.02 (C-1"), 149.86 (C-1), 164.62 ($CH_2$—COO), 169.20 (COO-Bn), 171.11 (COO-Me), ESI MS: 420.1 $(M+Na)^+$ (38), 398.2 $(MH)^+$ (100).

HRMS (ESI): For $C_{22}H_{23}O_6NNa$ $(M+Na)^+$ calculated: 420.14176; found: 420.14120. For $C_{22}H_{24}O_6N$ $(MH)^+$ calculated: 398.15981; found: 398.15939.

Alkyl α-Methyl Itaconates

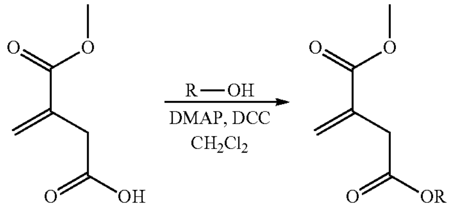

R=alkyl, aryl, alkyl salicylyl, Boc-tyrosyl alkylamide, Boc-tyrosyl ester, (di)peptide with terminal tyrosyl ester, (di)peptide with terminal tyrosyl alkylamide Examples of R—OH for Alkyl α-Methyl Itaconates Include, but are not Limited to:

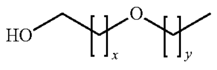

x= 1-3
y= 13-17

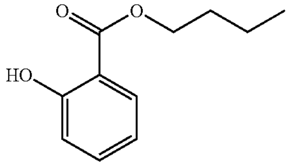

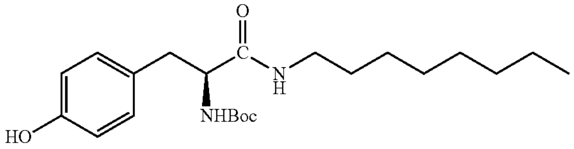

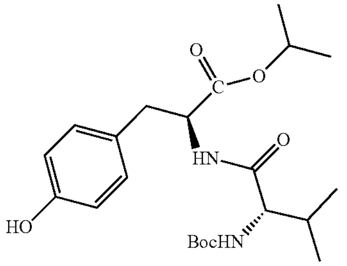

-continued

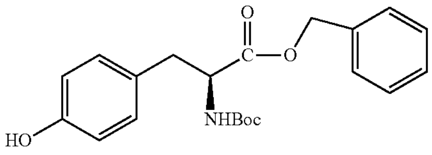

α-Methyl itaconate (1 mmol) was dissolved in dry dichloromethane (3 mL). Appropriate hydroxy derivative (1.2 mmol) and DMAP (1.5 mmol) were added and the solution cooled to 0° C. A solution of DCC (1.5 mmol) in dichloromethane (2 mL) was added dropwise under nitrogen and the whole mixture stirred for 1 h at 0° C. and then overnight at room temperature. The mixture was filtered, the solution extracted with 10% aqueous $KHSO_4$ (3×5 mL) and saturated $NaHCO_3$ (5 mL). The organic phase was dried over sodium sulfate, evaporated and the residue chromatographed on a column of silica gel in system escribed below.

1-Methyl 4-(4-(tetradecyloxy)butyl) 2-methylene-succinate (MK-956)

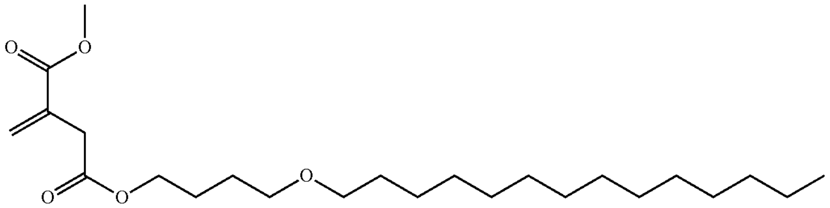 [SMILES: C=C(CC(=O)OCCCCOCCCCCCCCCCCCCC)C(=O)OC]

Chromatography in system cyclohexane—ethyl acetate (10:1). Yield: 244 mg (59%) of a colorless liquid.

$^1H$ NMR ($CDCl_3$, ppm) δ: 0.87 (t, 3H, $J_{CH3,CH2}$=7.0, $CH_3$ (14)), 1.24-1.33 (m, 22H, 11×$CH_2$ (3-13)), 1.54 (m, 2H, $CH_2$ (2)), 1.62 (m, 2H, $COO(CH_2)_2CH_2CH_2O$), 1.69 (m, 2H, COO—$CH_2CH_2$), 3.33 (d, 2H, $J_{CH2,C{=}CH2}$=1.2, $CH_2$—COO), 3.38 (t, 2H, $J_{1,2}$=6.7, $CH_2$ (1)), 3.41 (t, 2H, $J_{CH2,CH2}$=6.4, COO—$(CH_2)_3CH_2O$), 3.76 (s, 3H, $OCH_3$), 4.12 (t, 2H, $J_{CH2,CH2}$=6.5, COO—$CH_2$), 5.70 (q, 1H, $J_{Ha,CH2}$=$J_{gem}$ 1.1, =$CH_a$), 6.32 (d, 1H, $J_{gem}$ 1.1, =$CH_b$).

$^{13}C$ NMR ($CDCl_3$, ppm) δ: 14.11 (C-14), 22.67 (C-13), 25.42 (COO—$CH_2$—$CH_2$), 26.14 and 26.17 (C-3, COO $(CH_2)_2CH_2CH_2O$), 29.34-29.73 (m, C-2, C-4-C-11), 31.91 (C-12), 37.75 ($CH_2COO$), 52.10 ($OCH_3$), 64.81 (COO—$CH_2$), 70.10 (COO—$(CH_2)_3CH_2O$), 71.05 (C-1), 128.44 (C=$CH_2$), 133.75 (C=$CH_2$), 166.65 (COO—$CH_3$), 170.72 ($CH_2$—COO).

ESI MS: 847.6 $(2M+Na)^+$ (10), 435.3 $(M+Na)^+$ (100).

HRMS (ESI): For $C_{24}H_{44}O_5Na$ $(M+Na)^+$ calculated: 435.30810; found: 435.30841.

4-(3-(Hexadecyloxy)propyl) 1-methyl 2-methylene-succinate (MK-957)

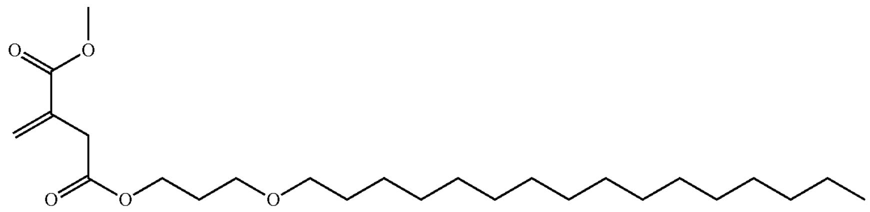 [SMILES: C=C(CC(=O)OCCCOCCCCCCCCCCCCCCCC)C(=O)OC]

Chromatography in system cyclohexane—ethyl acetate (80:15). Yield: 120 mg (28%) of a colorless liquid.

$^{1}$H NMR ($CDCl_3$, ppm) δ: 0.87 (t, 3H, $J_{CH3,CH2}$=7.0, $CH_3$ (16)), 1.23-1.33 (m, 26H, 13×$CH_2$ (3-15)), 1.54 (m, 2H, $CH_2$ (2)), 1.88 (p, 2H, $OCH_2$—$CH_2$—$CH_2O$), 3.33 (d, 2H, $J_{CH2,C{=}CH2}$=1.2, $CH_2$—COO), 3.38 (t, 2H, $J_{1,2}$=6.7, $OCH_2$ (1)), 3.45 (t, 2H, $J_{CH2,CH2}$=6.3, COO—$(CH_2)_2CH_2O$), 3.76 (s, 3H, $OCH_3$), 4.19 (t, 2H, $J_{CH2,CH2}$=6.5, COO—$CH_2$), 5.70 (q, 1H, $J_{Ha,CH2}$=$J_{gem}$ 1.1, =$CH_a$), 6.32 (d, 1H, $J_{gem}$ 1.1, =$CH_b$).

$^{13}$C NMR ($CDCl_3$, ppm) δ: 14.10 (C-16), 22.67 (C-15), 26.14 (C-3), 28.98 ($OCH_2$—$CH_2$—$CH_2O$), 29.34-29.69 (m, C-2, C-4-C-13), 31.91 (C-14), 37.72 ($CH_2COO$), 52.10 ($OCH_3$), 62.27 (COO—$CH_2$), 66.99 (COO—$(CH_2)_2CH_2O$), 71.16 (C-1), 128.44 (C=$CH_2$), 133.73 (C=$CH_2$), 166.63 (COO—$CH_3$), 170.64 ($CH_2$—COO).

ESI MS: 875.7 (2M+Na)+(5), 449.3 (M+Na)+(100).

HRMS (ESI): For $C_{25}H_{46}O_5Na$ $(M+Na)^+$ calculated: 449.32375; found: 449.32382.

4-(2-(Butoxycarbonyl)phenyl) 1-methyl 2-methyl-enesuccinate (MK-961)

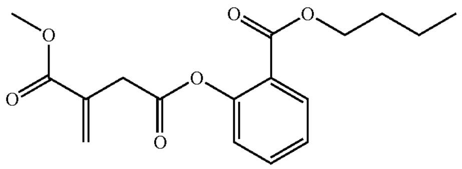 [SMILES: C=C(CC(=O)Oc1ccccc1C(=O)OCCCC)C(=O)OC]

Chromatography in system cyclohexane—ethyl acetate (6:1). Yield: 63 mg (20%) of a colorless liquid.

$^{1}$H NMR ($CDCl_3$, ppm) δ: 0.97 (t, 3H, $J_{CH3,CH2}$=7.4, $CH_3$ (4')), 1.45 (m, 2H, $CH_2$ (3')), 1.72 (m, 2H, $CH_2$ (2')), 3.67 (d, 2H, $J_{CH2,C{=}CH2}$=1.1, $CH_2$—C=O), 3.81 (s, 3H, $OCH_3$), 4.27 (t, 2H, $J_{1',2'}$=6.7, $OCH_2$ (1')), 5.89 (q, 1H, $J_{gem}$=$J_{Ha,CH2}$=1.1, =$CH_a$), 6.42 (d, 1H, $J_{gem}$=1.1, =$CH_b$), 7.11 (dddd, 1H, $J_{3,4}$=8.1, $J_{3,5}$=1.1, H-3), 7.30 (m, 1H, H-5), 7.54 (ddd, 1H, $J_{4,3}$=8.2, $J_{4,5}$=7.4, $J_{4,6}$=1.7, H-4), 8.00 (dd, 1H, $J_{6,5}$=7.9, $J_{6,4}$=1.7, H-6).

$^{13}$C NMR ($CDCl_3$, ppm) δ: 13.74 (C-4'), 19.20 (C-3'), 30.68 (C-2'), 37.50 $CH_2C$=O), 52.20 ($OCH_3$), 64.97 (C-1'), 123.43 (C-1), 123.79 (C-3), 126.04 (C-5), 129.30 (=$CH_2$), 131.59 (C-6), 133.19 (C=$CH_2$), 133.67 (C-4), 150.56 (C-2), 164.38 (COOBu), 166.59 ($COOCH_3$), 169.37 ($CH_2$—COO).

ESI MS: 343.1 $(M+Na)^+$ (100).

HRMS (ESI): For $C_{17}H_{20}O_6Na$ $(M+Na)^+$ calculated: 343.11521; found: 343.11532.

4-(4-((S)-2-((S)-2-((tert-butoxycarbonyl)amino)-3-methylbutanamido)-3-isopropoxy-3-oxopropyl)phenyl) 1-methyl 2-methylenesuccinate (MK-962)

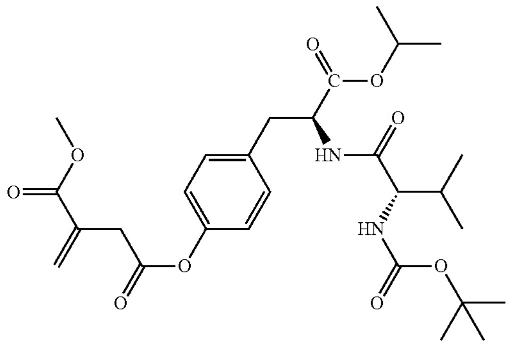 [SMILES: C=C(CC(=O)Oc1ccc(C[C@H](NC(=O)[C@@H](NC(=O)OC(C)(C)C)C(C)C)C(=O)OC(C)C)cc1)C(=O)OC]

Chromatography in system cyclohexane—acetone (4:1). Yield: 255 mg (47%) of a white solid.

$^{1}$H NMR (DMSO-$d_6$, ppm) δ: 0.77-0.79 (m, 6H, $CH(CH_3)_2$), 1.04 and 1.12 (2× d, 6H, $J_{CH3,CH}$=6.2, OCH$(CH_3)_2$), 1.37 (s, 9H, $C(CH_3)_3$), 1.85 (m, 1H, $CH(CH_3)_2$), 2.93 (dd, 1H, $J_{3'a,2'}$=8.5, $J_{gem}$=14.0, H-3'a), 2.99 (dd, 1H, $J_{3'b,2'}$=6.6, $J_{gem}$=14.0, H-3'b), 3.62 (s, 2H, $CH_2$—COOMe), 3.72 (s, 3H, $OCH_3$), 3.80 (m, 1H, H-2'), 4.42 (q, 1H, $J_{2'3'}$=$J_{2',NH}$=7.4, H-2'), 4.81 (sept, 1H, $J_{CH,CH3}$=6.2, OCH$(CH_3)_2$), 5.96 and 6.28 (2× s, 2H, =$CH_2$), 6.57 (d, 1H, $J_{NH,2''}$=9.2, NH-2"), 6.97 (m, 2H, H-arom. (2)), 7.26 (m, 2H, H-arom. (3)), 8.26 (d, $J_{NH,2'}$=7.4, NH-2').

$^{13}$C NMR (DMSO-$d_6$, ppm) δ: 18.35 and 19.31 (C-4"), 21.50 and 21.65 (O—$CH(CH_3)_2$), 28.36 ($C(CH_3)_3$), 30.71 (C-3"), 36.24 (C-3'), 37.38 ($CH_2$—COOMe), 52.29 ($OCH_3$), 53.66 (C-2'), 59.61 (C-2"), 68.19 (O—$CH(CH_3)_2$), 78.16 ($C(CH_3)_3$), 121.42 (C-2), 129.66 (=$CH_2$), 130.41 (C-3), 133.62 (C=$CH_2$), 134.89 (C-4), 149.24 (C-1), 155.48 (NH—COO), 166.27 (COO-Me), 169.38 (COO-Ph), 170.94 (C-1'), 171.59 (C-1").

ESI MS: 571.3 $(M+Na)^+$ (100).

HRMS (ESI): For $C_{28}H_{40}O_9N_2Na$ $(M+Na)^+$ calculated: 571.26260; found: 571.26280.

(S)-4-(4-(3-(Benzyloxy)-2-((tert-butoxycarbonyl) amino)-3-oxopropyl)phenyl) 1-methyl 2-methylene-succinate (MK-963)

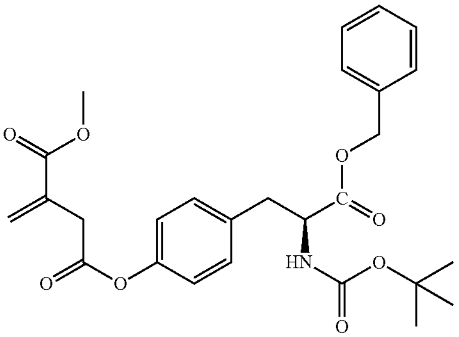 [SMILES: C=C(CC(=O)Oc1ccc(C[C@H](NC(=O)OC(C)(C)C)C(=O)OCc2ccccc2)cc1)C(=O)OC]

Chromatography in system cyclohexane—acetone (4:1). Yield: 223 mg (45%) of an amorphous solid.

$^1$H NMR ($CDCl_3$, ppm) δ: 1.41 (s, 9H, $C(CH_3)_3$), 3.04 (dd, 1H, $J_{3'a,2'}$=6.0, $J_{gem}$=14.0, H-3'a), 3.09 (dd, 1H, $J_{3'b,2'}$=6.0, $J_{gem}$=13.9, H-3'b), 3.56 (d, 2H, $J_{CH2,C=CH2}$=1.1, $CH_2$—COOMe), 3.80 (s, 3H, $OCH_3$), 4.60 (m, 1H, CH—NH), 4.99 (d, $J_{NH,CH}$=8.3, NH), 5.09 and 5.17 (2× d, 2H, $J_{gem}$=12.2, O—$CH_2$Ph), 5.82 (q, 1H, $J_{CH2,=CHa}$=$J_{gem}$=1.1, =$CH_a$), 6.40 (d, 1H, $J_{gem}$=0.8, =$CH_b$), 6.95 (m, 2H, H-2 (arom.)), 7.02 (m, 2H, H-3 (arom.)), 7.28-7.38 (m, 5H, H-2", H-3", H-4"(arom.)).

$^{13}$C NMR ($CDCl_3$, ppm) δ: 28.25 ($C(CH_3)_3$), 37.51 (C-3'), 37.86 ($CH_2$—COOMe), 52.23 ($OCH_3$), 54.31 (C-2'), 67.15 (O—$CH_2$Ph), 79.97 ($C(CH_3)_3$), 121.40 (C-2), 128.48 (C-4"), 128.58 and 128.60 (C-2", C-3"), 129.00 (=$CH_2$), 130.28 (C-3), 133.29 (C=$CH_2$), 133.50 (C-4), 135.06 (C-1"), 149.61 (C-1), 155.02 (NH—CO), 166.47 (COO-Me), 169.07 ($CH_2$—COO), 171.51 (C-1').

ESI MS: 1017.7 (2M+Na)+(3), 520.3 (M+Na)+(100).

HRMS (ESI): For $C_{27}H_{31}O_8NNa$ $(M+Na)^+$ calculated: 520.19419; found: 520.19324. For $C_{27}H_{32}O_8N$ $(MH)^+$ calculated: 498.21224; found: 498.21161.

Deprotection of Tert-Butoxycarbonyl (Boc) Group. General Procedure.

A mixture of dichloromethane and trifluoroacetic acid (1:1, 16 mL) was added to appropriate Boc derivative (0.8 mmol). The solution was stirred at room temperature for 20 min and evaporated. The residue was worked-up as decribed below.

4-(4-((S)-2-((S)-2-amino-3-methylbutanamido)-3-isopropoxy-3-oxopropyl)phenyl) 1-methyl 2-methylenesuccinate, trifluoroacetate salt (MK-964)

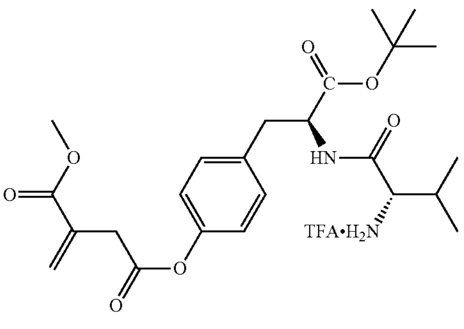

The residue was crystallized from a mixture ethyl—acetate and diethyl ether. Yield: 340 mg (75%) of white crystals.

$^1$H NMR (DMSO-$d_6$, ppm) δ: 0.93 and 0.97 (2× d, 6H, $CH(CH_3)_2$), 1.06 and 1.14 (2× d, 6H, $J_{CH3,CH}$=6.2, O—CH$(CH_3)_2$), 2.12 (sept d, 1H, $J_{3'',4''}$=6.9, $J_{3'',2''}$=5.0, H-3"), 2.98 (dd, 1H, $J_{3'a,2'}$=8.2, $J_{gem}$=14.2, H-3'a), 3.03 (dd, 1H, $J_{3'b,2'}$=6.6, $J_{gem}$=14.2, H-3'b), 3.64 (m, 2H, $CH_2$—COOMe), 3.65 (d, 1H, $J_{2'',3''}$=5.1, H-2"), 3.73 (s, 3H, $OCH_3$), 4.49 (m, 1H, H-2'), 4.84 (sept, 1H, $J_{CH,CH3}$=6.2, O—$CH(CH_3)_2$), 5.96 (q, 1H, $J_{CH2,=CHa}$=$J_{gem}$=1.2, =$CH_a$), 6.28 (d, 1H, $J_{gem}$=1.2, =$CH_b$), 7.02 (m, 2H, H-2), 7.31 (m, 2H, H-3), 8.09 (bs, 3H, $NH_3$+), 8.89 (d, 1H, $J_{NH,2'}$=7.0, NH).

$^{13}$C NMR (DMSO-$d_6$, ppm) δ: 17.43 and 18.51 (C-4"), 21.47 and 21.65 (O—$CH(CH_3)_2$), 30.07 (C-3"), 36.03 (C-3'), 37.40 ($CH_2$—COOMe), 52.32 ($OCH_3$), 54.23 (C-2'), 57.23 (C-2"), 68.60 (0-$CH(CH_3)_2$), 121.62 (C-2), 129.72 (=$CH_2$), 130.47 (C-3), 133.60 (C=$CH_2$), 134.56 (C-4), 149.40 (C-1), 166.30 (COO-Me), 168.37 (NH—CO), 169.51 ($CH_2$—COO), 170.53 (COO-iPr).

ESI MS: 471.2 $(M+Na)^+$ (20), 449.2 $(MH)^+$ (100).

HRMS (ESI): For $C_{23}H_{33}O_7N_2$ $(MH)^+$ calculated: 449.22823; found: 449.22745.

(S)-4-(4-(2-Amino-3-(benzyloxy)-3-oxopropyl)phenyl) 1-methyl 2-methylenesuccinate, trifluoroacetate salt (MK-965)

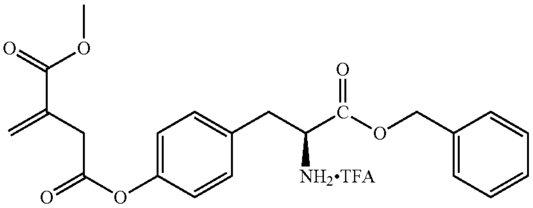

The residue was chromatographed on silica gel column (60 mL) in a gradient cyclohexane—acetone (1:1 to 1:4), followed by the system chloroform—methanol (1:1) to give 380 mg (93%) of a white sticky foam.

$^1$H NMR (DMSO-$d_6$, ppm) δ: 3.07 (dd, 1H, $J_{3'a,2'}$=7.5, $J_{gem}$=14.1, H-3'a), 3.15 (dd, 1H, $J_{3'b,2'}$=6.1, $J_{gem}$=14.1, H-3'b), 3.66 (d, 2H, $J_{CH2,C=CH2}$=1.2, $CH_2$—COOMe), 3.73 (s, 3H, $OCH_3$), 4.37 (dd, 1H, $J_{2',3'}$=7.6 and 6.1, H-2'), 5.13 and 5.17 (2× d, 2H, $J_{gem}$=12.3, O—$CH_2$Ph), 5.98 (q, 1H, $J_{gem}$=$J_{CH2,=CHa}$=1.2, =$CH_a$), 6.30 (d, 1H, $J_{gem}$=1.2, =$CH_b$), 7.02 (m, 2H, H-2 (arom.)), 7.22 (m, 2H, H-3 (arom.)), 7.26 (m, 2H, H-2"(arom.)), 7.34-7.37 (m, 3H, H-3", H-4"(arom.)), 8.48 (bs, 3H, $NH_3^+$).

$^{13}$C NMR (DMSO-$d_6$, ppm) δ: 35.71 (C-3'), 34.73 ($CH_2$—COOMe), 52.33 ($OCH_3$), 53.35 (C-2'), 67.35 (O—$CH_2$Ph), 121.88 (C-2), 128.60 (C-2", C-3"), 128.63 (C-4"), 129.72 ((=$CH_2$), 130.80 (C-3'), 132.42 (C-4), 133.62 (C=$CH_2$), 135.01 (C-1"), 149.82 (C-1), 166.32 (COO-Me), 169.25 (COO-Bn), 169.40 ($CH_2$—COO).

ESI MS: 420.1 $(M+Na)^+$ (15), 398.2 $(MH)^+$ (100).

HRMS (ESI): For $C_{22}H_{23}O_6NNa$ $(M+Na)^+$ calculated: 420.14176; found: 420.14105. For $C_{22}H_{24}O_6N$ $(MH)^+$ calculated: 398.15981; found: 398.15930.

4-(((Isopropoxycarbonyl)oxy)methyl) 1-methyl 2-methylenesuccinate (IS-101-088) (21)

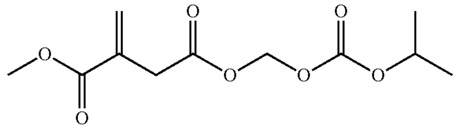 [SMILES: C=C(CC(=O)OCOC(=O)OC(C)C)C(=O)OC]

α-Methyl itaconate (0.2 g, 1.39 mmol), chloromethyl isopropyl carbonate (0.22 mL, 1.66 mmol), sodium iodide (50 mg, 0.33 mmol) and potassium carbonate (0.29 g, 2.08 mmol) were dissolved in anhydrous MeCN (5 mL) and the mixture was stirred for 16 hours at 50° C. EtOAc (60 mL) was added and the mixture was washed with brine (20 mL). The organic phase was dried over $Na_2SO_4$, volatiles were evaporated and the residue was subjected to flash column chromatography (Silicagel 60 mesh 70-230, solvent: cyclohexane/ethyl acetate 5:1) to afford 0.34 g (93%) of compound IS-101-088 (21) as colorless oil.

$^1H$ NMR (401 MHz, $CDCl_3$): $\delta_H$ 1.31 (d, J=6.2 Hz, 6H), 3.37-3.43 (m, 2H), 3.76 (d, J=0.6 Hz, 3H), 4.85-4.97 (m, 1H), 5.72-5.78 (m, 3H), 6.36 (d, J=0.8 Hz, 1H).

$^{13}C$ NMR (101 MHz, $CDCl_3$): $\delta_C$ 21.6, 21.7, 37.3, 52.2, 73.1, 81.9, 129.2, 132.9, 153.3, 166.3, 169.2.

ESI MS: 283.1 ($[M+Na]^+$).

HRMS (ESI): Calcd. for $C_{11}H_{16}O_7Na$ 283.07882. Found: 283.07925.

1-Methyl 4-((pivaloyloxy)methyl) 2-methylenesuccinate (IS-101-089) (23)

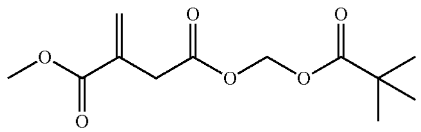 [SMILES: C=C(CC(=O)OCOC(=O)C(C)(C)C)C(=O)OC]

α-Methyl itaconate (0.2 g, 1.39 mmol), chloromethyl pivalate (0.26 mL, 1.8 mmol), sodium iodide (50 mg, 0.33 mmol) and potassium carbonate (0.29 g, 2.08 mmol) were dissolved in anhydrous MeCN (5 mL) and the mixture was stirred for 16 hours at 40° C. EtOAc (60 mL) was added and the mixture was washed with brine (20 mL). The organic phase was dried over $Na_2SO_4$, volatiles were evaporated and the residue was subjected to flash column chromatography (Silicagel 60 mesh 70-230, solvent: cyclohexane/ethyl acetate 5:1) to afford 0.33 g (92%) of compound IS-101-089 (23) as colorless oil.

$^1H$ NMR (401 MHz, $CDCl_3$): $\delta_H$ 1.21 (s, 9H), 3.38 (d, J=1.2 Hz, 2H), 3.76 (s, 3H), 5.74 (d, J=1.1 Hz, 1H), 5.76 (s, 2H), 6.35 (d, J=0.8 Hz, 1H).

$^{13}C$ NMR (101 MHz, $CDCl_3$): $\delta_C$ 26.9, 37.4, 38.8, 52.2, 79.7, 129.0, 133.0, 166.3, 169.4, 177.1.

ESI MS: 281.1 ($[M+Na]^+$).

HRMS (ESI): Calcd. for $C_{12}H_{18}O_6Na$ 281.09956. Found: 281.09993.

1-(((tert-Butoxycarbonyl)oxy)methyl) 4-methyl 2-methylenesuccinate (IS-102-081)

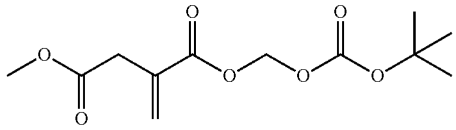 [SMILES: C=C(CC(=O)OC)C(=O)OCOC(=O)OC(C)(C)C]

β-Methyl itaconate (1.00 g, 6.94 mmol), tert-butyl (chloromethyl) carbonate (1.27 g, 7.60 mmol), sodium iodide (0.20 g, 1.33 mmol) and potassium carbonate (1.44 g, 10.4 mmol) were dissolved in anhydrous MeCN (20 mL) and the mixture was stirred for 16 hours at 50° C. Volatiles were then evaporated, the residue was redissolved in EtOAc (60 mL) and the mixture was washed with saturated solution of sodium thiosulfate (20 mL) and brine (70 mL). The organic phase was dried over $Na_2SO_4$, volatiles were evaporated and the residue was subjected to flash column chromatography (Silicagel 60 mesh 70-230, solvent: cyclohexane/ethyl acetate 5:1) to afford 1.65 g (87%) of compound IS-102-081 as colorless oil.

$^1H$ NMR (401 MHz, $CDCl_3$): $\delta_H$ 1.49 (s, 9H), 3.34 (s, 2H), 3.68 (s, 3H), 5.78 (s, 2H), 5.81 (s, 1H), 6.42 (s, 1H).

$^{13}C$ NMR (101 MHz, $CDCl_3$): $\delta_C$ 27.7, 37.3, 52.2, 82.0, 83.7, 130.5, 133.0, 152.0, 164.7, 170.9.

ESI MS: 297.1 ($[M+Na]^+$).

HRMS (ESI): Calcd. for $C_{12}H_{18}O_7Na$ 297.09447. Found: 297.09465.

Scheme 1. Structure numbering for NMR assignment (alkyl β-methyl itaconates)

MK-933

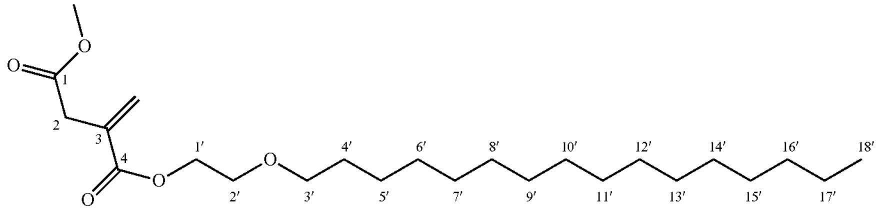

-continued
MK-939
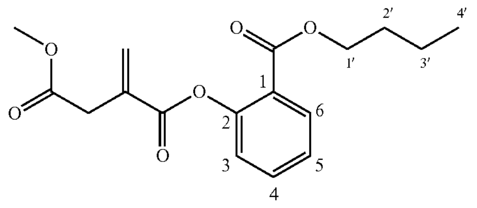
MK-937
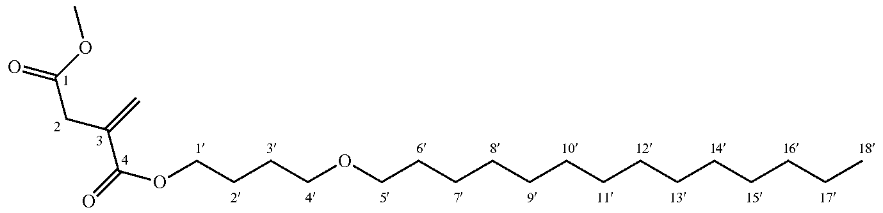
MK-942, MK-944
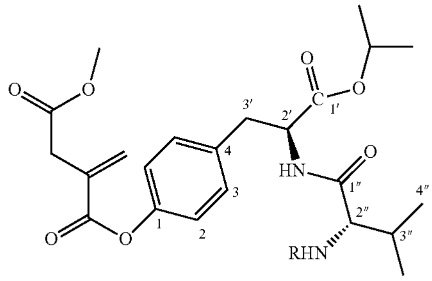
R = H, BOC
MK-940
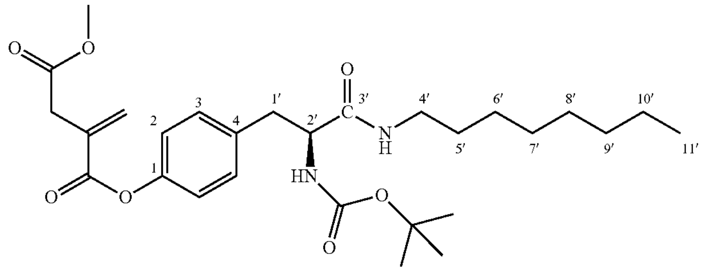
MK-941
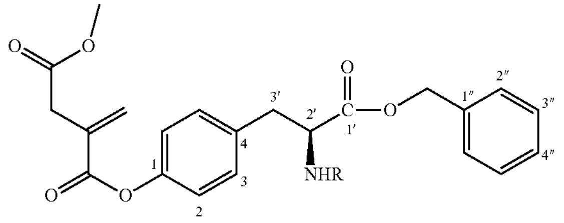
R = H, BOC
MK-943, MK-945
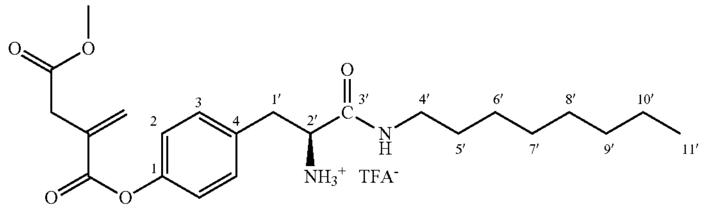

Scheme 2. Structure numbering for NMR assignment (alkyl α-methyl itaconates)

MK-957

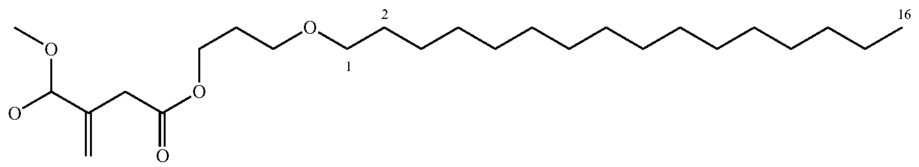

MK-961

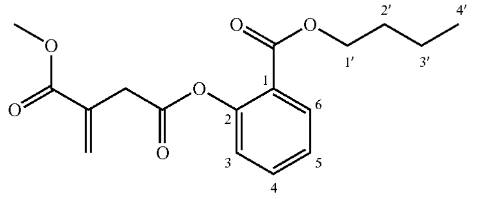

MK-956

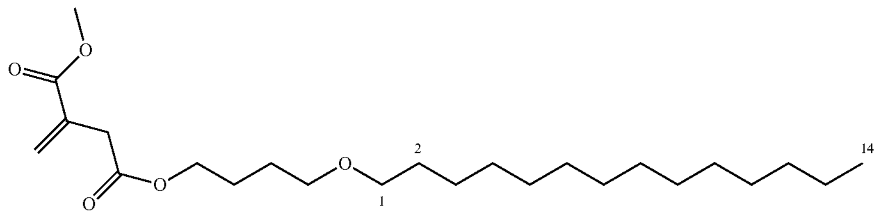

MK-962, MK-964

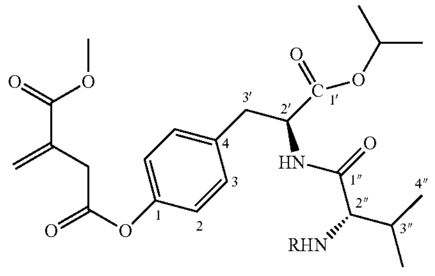

R = H, BOC

MK-963, MK-965

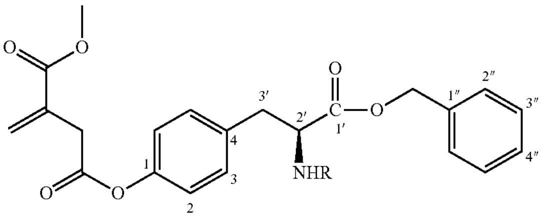

R = H, BOC

Example 6

In Vitro Data—Mouse Plasma Stability

To evaluate the mouse plasma stability of the intact prodrug over time, the prodrug was spiked into mouse plasma to a final assay concentration of 10 μM. Spiked samples were incubated in an orbital shaker at 37° C. for 1 h, following which reactions were quenched with three volumes of acetonitrile containing the internal standard (IS; losartan: 0.5 μM). The samples were vortex-mixed and centrifuged at 16 000 g for 5 min at 4° C. Fifty microliters of the supernatant was diluted with 50 μL of water and transferred to a 250 μL polypropylene vial sealed with a Teflon cap. Prodrug disappearance was monitored over time using liquid chromatography mass spectrometry (LC-MS). The results for representative presently disclosed prodrugs are shown in FIG. 1. The release of active monomethyl itaconate (in plasma) from representative prodrugs in shown in FIG. 2. The release of active itaconic acid (in plasma) from representative prodrugs in shown in FIG. 3.

REFERENCES

All publications, patent applications, patents, and other references mentioned in the specification are indicative of the level of those skilled in the art to which the presently disclosed subject matter pertains. All publications, patent applications, patents, and other references are herein incorporated by reference to the same extent as if each individual publication, patent application, patent, and other reference was specifically and individually indicated to be incorporated by reference. It will be understood that, although a number of patent applications, patents, and other references are referred to herein, such reference does not constitute an admission that any of these documents forms part of the common general knowledge in the art.

International PCT patent application publication no. WO2017142855 to Artyomov et al., for Immunomodulatory Agents and Methods of Use Thereof, published Aug. 24, 2017;

International PCT patent application publication no. WO2019036509 to Artyomov et al., for Methods and Compositions for the Treatment of Diseases Associated with Cancer, Inflammation, or Immune Response, published Feb. 21, 2019;

O'Neill, L. A. J. and Artyomov, M. N., Itaconate: the poster child of metabolic reprogramming in macrophage function, Nature Reviews: Immunology, 19, 273-281 (2019).

Boschert, D.; Schneider-Chaabane, A.; Himmelsbach, A.; Eickenscheidt, A.; Lienkamp, K. Synthesis and Bioactivity of Polymer-Based Synthetic Mimics of Antimicrobial Peptides (SMAMPs) Made from Asymmetrically Disubstituted Itaconates. *Chem. Eur. J.* 2018, 24, 8217-8227.

McKenna, C. E.; Kashemirov, B. A; Krylov, I. S.; Zakharova, V. M. Method to improve antiviral activity of nucleotide analogue drugs. U.S. Pat. No. 9,550,803 B2, Jan. 24, 2017.

Hidaka, K.; Gohda, K.; Teno, N.; Wanaka, K.; Tsuda, Y. Active site-directed plasmin inhibitors: Extension on the P2 residue. *Bioorg. Med. Chem.* 2016, 24, 545-553.

Although the foregoing subject matter has been described in some detail by way of illustration and example for purposes of clarity of understanding, it will be understood by those skilled in the art that certain changes and modifications can be practiced within the scope of the appended claims.

What is claimed is:

1. A compound of formula (I):

(I)

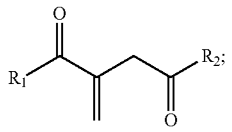

or a pharmaceutically acceptable salt thereof, wherein $R_1$ and $R_2$ are selected from one of the following combinations:

(a) $R_1$ is —OH and $R_2$ is

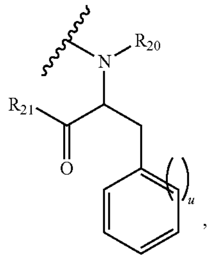

wherein u is an integer selected from 1, 2, 3 and 4, $R_{20}$ is H, $R_{21}$ is O—$C_{1-6}$ alkyl;

(b) $R_1$ is O—$C_{1-6}$ alkyl, and $R_2$ is

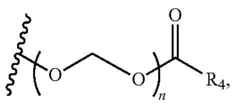

$R_4$ is O—$C_{1-6}$ alkyl, wherein n is an integer selected from 1, 2, 3 and 4;

(c) $R_1$ is

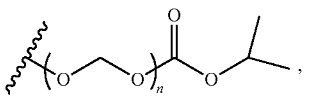

wherein n is an integer selected from 1, 2, 3 and 4, and $R_2$ is O—$C_{1-6}$ alkyl;

(d) $R_1$ is

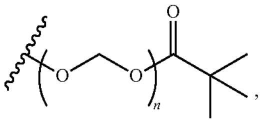

wherein n is an integer selected from 1, 2, 3 and 4, and $R_2$ is O—$C_{1-6}$ alkyl;

(e) $R_1$ and $R_2$ are

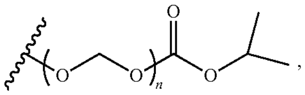

wherein n is an integer selected from 1, 2, 3 and 4;

(f) $R_1$ is

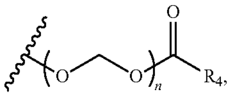

$R_4$ is O—$C_{1-6}$ alkyl, wherein n is an integer selected from 1, 2, 3 and 4, and $R_2$ is O—$C_{1-6}$ alkyl; and (g) $R_1$ is

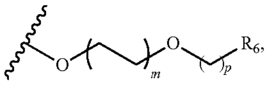

wherein m is an integer selected from 1, 2, 3 and 4, $R_6$ is $CH_3$, p is an integer selected from 1, 2, 3, 4, 5, 6, 7, 8, 9, 10, 11, 12, 13, 14, 15, 16, 17, 18, 19, and 20, and $R_2$ is O—$C_{1-6}$ unsubstituted alkyl.

2. The compound or pharmaceutically acceptable salt thereof of claim 1, wherein:

(i) $R_1$ is OH, and $R_2$ is

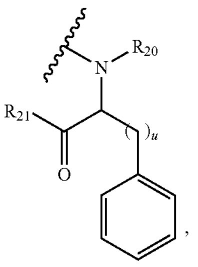

wherein u is 1, $R_{20}$ is H, $R_{21}$ is O—$C_{1-6}$ alkyl;

(ii) $R_1$ is

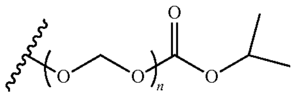, wherein n is 1, and $R_2$ is O—$C_{1-6}$ alkyl;

(iii) $R_1$ is

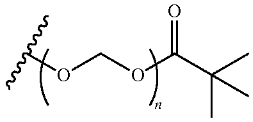, wherein n is 1, and $R_2$ is O—$C_{1-6}$ alkyl;

(iv) $R_1$ and $R_2$ are

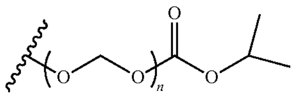, wherein n is 1;

(v) $R_1$ is

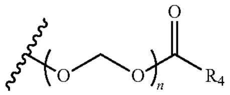

$R_4$ is O—$C_{1-6}$ alkyl, wherein n is 1, and $R_2$ is O—$C_{1-6}$ alkyl;

(vi) $R_1$ is O—$C_{1-6}$ alkyl, and $R_2$ is

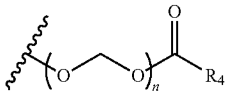

$R_4$ is O—$C_{1-6}$ alkyl, wherein n is 1; and (vii) $R_1$ is

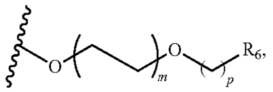

wherein m is an integer selected from 1, 2, 3 and 4, $R_6$ is $CH_3$, p is an integer selected from 7, 8, 9, 10, 11, 12, 13, 14, 15, 16, 17, 18, 19, and 20, and $R_2$ is O—$C_{1-6}$ unsubstituted alkyl.

3. The compound of claim 1, wherein the compound of formula (I) is selected from:

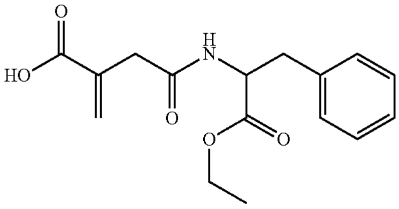,

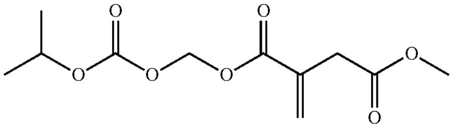,

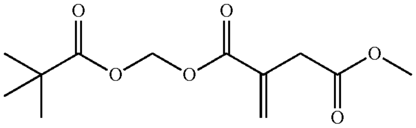,

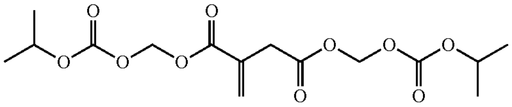,

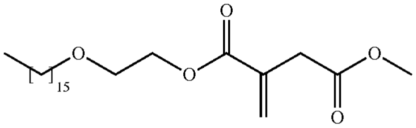,

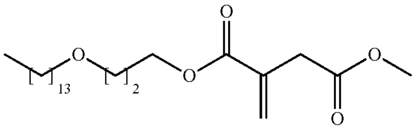,

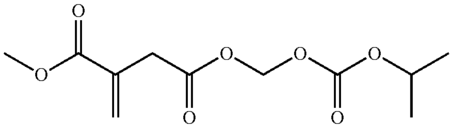, and

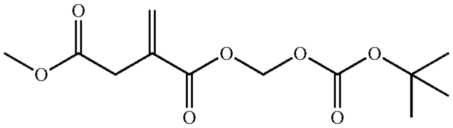;

and a pharmaceutically acceptable salt thereof.

4. A pharmaceutical composition comprising the compound of claim 1 and a pharmaceutically acceptable excipient.

* * * * *